(12) United States Patent
Gabriel et al.

(10) Patent No.: US 7,538,122 B2
(45) Date of Patent: May 26, 2009

(54) HETEROCYCLIC ANTIVIRAL COMPOUNDS

(75) Inventors: Stephen Deems Gabriel, San Mateo, CA (US); David Mark Rotstein, Sunnyvale, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 0 days.

(21) Appl. No.: 12/008,452

(22) Filed: Jan. 11, 2008

(65) Prior Publication Data

US 2008/0139544 A1  Jun. 12, 2008

Related U.S. Application Data

(62) Division of application No. 11/055,642, filed on Feb. 10, 2005, now Pat. No. 7,332,500.

(60) Provisional application No. 60/543,408, filed on Feb. 10, 2004.

(51) Int. Cl.
A61K 31/445 (2006.01)
C07D 221/00 (2006.01)

(52) U.S. Cl. .................. 514/318; 514/326; 546/15
(58) Field of Classification Search ............... 514/318, 514/326; 546/15
See application file for complete search history.

(56) References Cited

U.S. PATENT DOCUMENTS

| 3,399,192 | A | 8/1968 | Regnier et al. |
|---|---|---|---|
| 6,391,865 | B1 | 5/2002 | Baroudy et al. |
| 6,689,765 | B2 | 2/2004 | Baroudy et al. |
| 6,911,452 | B2 * | 6/2005 | Schlienger ............ 514/278 |
| 2003/0069252 | A1 | 4/2003 | Baroudy et al. |
| 2003/0166928 | A1 | 9/2003 | Schlienger |

FOREIGN PATENT DOCUMENTS

| EP | 414422 B1 | 4/1994 |
|---|---|---|
| EP | 1236726 A1 | 4/2002 |
| WO | WO 97/11940 A1 | 4/1997 |
| WO | WO 00/66558 A1 | 11/2000 |
| WO | WO 00/66559 A1 | 11/2000 |
| WO | WO 01/57044 A1 | 8/2001 |
| WO | WO 02/092604 A1 | 11/2002 |
| WO | WO 03/057698 A2 | 7/2003 |

OTHER PUBLICATIONS

Caroon, Joan, et al.; "Synthesis and Antihypertensive Activity of a Series of 8-Substituted 1-Oxa-3,8-diazaspiro [4.5]decan-2-ones[1]" J. Med. Chem. (1981) pp. 1320-1328, vol. 24.

Clark, Robin, et al.; "Antihypertensive 9-Substituted 1-Oxa-4,9-diazaspiro[5.5]undecan-3- ones[1]" J. Med. Chem. (1983) pp. 855-861, vol. 26.

Kazmierski, W., et al.; "Recent Progress in Discovery of Small-Molecule CCR5 Chemokine Receptor Ligands as HIV-1 Inhibitors," Bioorganic & Medicinal Chemistry (2003) pp. 2663-2676, vol. 11.

Palani, Anandan, et al.; "An Orally Bioavailable Human CCR5 Antagonist for the Treatment of HIV Infection," Journal of Medicinal Chemistry (Oct. 11, 2001), pp. 3339-3342, vol. 44:21.

Smith, Paul W. et al., "New Spiropiperdines as Potent and Selective Non-Peptide Tachykinin $NK_2$" J. Med. Chem. (1995) pp. 3772-3779, vol. 38.

Tagat, Jayaram, et al.; "Piperazine-Based CCR5 Antagonists as HIV-1 Inhibitors," J. Med. Chem. (2001) pp. 3343-3346, vol. 44.

* cited by examiner

*Primary Examiner*—James O Wilson
*Assistant Examiner*—Erich A Leeser
(74) *Attorney, Agent, or Firm*—Brian L. Buckwalter

(57) ABSTRACT

This invention relates to piperidine derivatives of formulae Ia and Ib with substituents as defined herein useful in the treatment of a variety of disorders, including those in which the modulation of CCR5 receptors is implicated. More particularly, the present invention relates to 1-oxa-3,8-diaza-spiro [4.5]decan-2-one and 1-oxa-3,9-diaza-spiro[5.5]undecan-2-one compounds and related derivatives, to compositions containing and to uses of such derivatives. Disorders that may be treated or prevented by the present derivatives include HIV and genetically related retroviral infections (and the resulting acquired immune deficiency syndrome, AIDS), diseases of the immune system and inflammatory diseases.

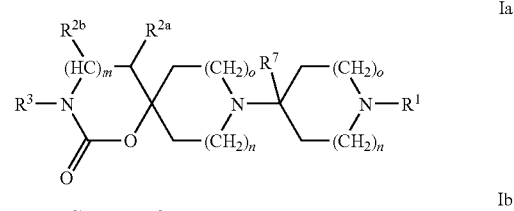

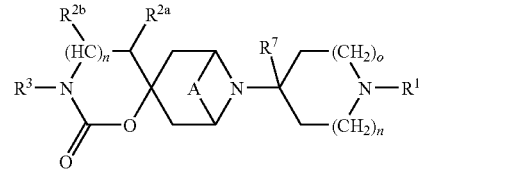

9 Claims, No Drawings

HETEROCYCLIC ANTIVIRAL COMPOUNDS

CROSS REFERENCE TO RELATED APPLICATIONS

This application is a divisional application of U.S. Ser. No. 11/055,642 filed Feb. 10, 2005 now U.S. Pat. No. 7,332,500 which claims the benefit of priority to U.S. Ser. No. 60/543,408 filed Feb. 10, 2004, both of which is hereby incorporated by reference in their entirety.

FIELD OF THE INVENTION

This invention relates to piperidine derivatives useful in the treatment of a variety of disorders in which modulation of the CCR5 receptor ligand binding is beneficial. More particularly, the present invention relates to 1-oxa-3,8-diaza-spiro[4.5]decan-2-one and 1-oxa-3,9-diaza-spiro[5.5]undecan-2-one compounds and related derivatives, to compositions containing said compounds and to uses of such derivatives. Disorders that may be treated or prevented by the present compounds include HIV and genetically related retroviral infections (and the resulting acquired immune deficiency syndrome, AIDS), diseases of the immune system and inflammatory diseases.

BACKGROUND OF THE INVENTION

Compounds of the present invention modulate the activity of the chemokine CCR5 receptors. The chemokines are a large family of pro-inflammatory peptides that exert their pharmacological effect through G-protein-coupled receptors. The name "chemokine", is a contraction of "chemotactic cytokines". The chemokines are a family of leukocyte chemotactic proteins capable of attracting leukocytes to various tissues, which is an essential response to inflammation and infection. Human chemokines include approximately 50 small proteins of 50-120 amino acids that are structurally homologous. (M. Baggiolini et al., *Ann. Rev. Immunol.* 1997 15:675-705)

Modulators of the CCR5 receptor may be useful in the treatment of various inflammatory diseases and conditions, and in the treatment of infection by HIV-1 and genetically related retroviruses. As leukocyte chemotactic factors, chemokines play an indispensable role in the attraction of leukocytes to various tissues of the body, a process which is essential for both inflammation and the body's response to infection. Because chemokines and their receptors are central to the pathophysiology of inflammatory and infectious diseases, agents which modulate CCR5 activity, preferably antagonizing interactions of chemokines and their receptors, are useful in the therapeutic treatment of such inflammatory and infectious diseases. The chemokine receptor CCR5 is of particular importance in the context of treating inflammatory and infectious diseases. CCR5 is a receptor for chemokines, especially for the macrophage inflammatory proteins (MIP) designated MIP-1a and MIP-1b, and for a protein which is regulated upon activation and is normal T-cell expressed and secreted (RANTES).

HIV-1 infects cells of the monocyte-macrophage lineage and helper T-cell lymphocytes by exploiting a high affinity interaction of the viral enveloped glycoprotein (Env) with the CD-4 antigen. The CD-4 antigen, however, appeared to be a necessary, but not sufficient requirement for cell entry and at least one other surface protein was required to infect the cells (E. A. Berger et al., *Ann. Rev. Immunol.* 1999 17:657-700). Two chemokine receptors, either the CCR5 or the CXCR4 receptor were subsequently found to be co-receptors along with CD4 which are required for infection of cells by the human immunodeficiency virus (HIV). The central role of CCR5 in the pathogenesis of HIV was inferred by epidemiological identification of powerful disease modifying effects of the naturally occurring null allele CCR5 Δ32. The Δ32 mutation has a 32-basepair deletion in the CCR5 gene resulting in a truncated protein designated Δ32. Relative to the general population, Δ32/Δ32 homozygotes are significantly common in exposed/uninfected individuals suggesting the role of CCR5 in HIV cell entry (R. Liu et al., *Cell* 1996 86(3):367-377; M. Samson et al., *Nature* 1996 382(6593):722-725). The CD4 binding site on the gp120 of HIV appears to interact with the CD4 molecule on the cell surface, and undergoes conformational changes which allow it to bind to another cell-surface receptor, such as CCR5 and/or CXCR-4. This brings the viral envelope closer to the cell surface and allows interaction between gp41 on the viral envelope and a fusion domain on the cell surface, fusion with the cell membrane, and entry of the viral core into the cell. Accordingly, an agent which could block chemokine receptors in humans who possess normal chemokine receptors should prevent infection in healthy individuals and slow or halt viral progression in infected patients.

RANTES, a natural ligand for the CCR5 receptor, and an analog chemically modified on the N-terminus, aminooxypentane RANTES, were found to block HIV entry into the cells. (G. Simmons et al., Science 1997 276:276-279). Other compounds have been demonstrated to inhibit the replication of HIV, including soluble CD4 protein and synthetic derivatives (Smith, et al., Science 1987 238:1704-1707), dextran sulfate, the dyes Direct Yellow 50, Evans Blue, and certain azo dyes (U.S. Pat. No. 5,468,469). Some of these antiviral agents have been shown to act by blocking the binding of gp120, the coat protein of HIV, to its target, the CD4 glycoprotein of the cell.

A-M. Vandamme et al. (*Antiviral Chemistry & Chemotherapy*, 1998 9:187-203) disclose current HAART clinical treatments of HIV-1 infections in man including at least triple drug combinations. Highly active anti-retroviral therapy (HAART) has traditionally consisted of combination therapy with nucleoside reverse transcriptase inhibitors (NRTI), non-nucleoside reverse transcriptase inhibitors (NNRTI) and protease inhibitors (PI). These compounds inhibit biochemical processes required for viral replication. In compliant drug-naive patients, HAART is effective in reducing mortality and progression of HIV-1 to AIDS. While HAART has dramatically altered the prognosis for HIV infected persons, there remain many drawbacks to the current therapy including highly complex dosing regimes and side effects which can be very severe (A. Carr and D. A. Cooper, *Lancet* 2000 356 (9239):1423-1430). Moreover, these multidrug therapies do not eliminate HIV-1 and long-term treatment usually results in multidrug resistance, thus limiting their utility in long term therapy. Development of new drug therapies to provide better HIV-1 treatment remains a priority. Investigation of different classes of modulators of chemokine receptor activity, especially that of the CCR5 chemokine receptor, suggest inhibition of CCR5 as a new treatment modality.

Typical suitable NRTIs include zidovudine (AZT) available as RETROVIR® from Glaxo-Wellcome Inc.; didanosine (dd1) available as VIDEX® from Bristol-Myers Squibb Co.; zalcitabine (ddC) available as HIVID® from Roche Pharmaceuticals; stavudine (d4T) available as ZERIT® from Bristol-Myers Squibb Co.; lamivudine (3TC) available as EPIVR® from Glaxo-Wellcome; abacavir (1592U89) disclosed in WO96/30025 and available ZIAGEN® from Glaxo- Wellcome; adefovir dipivoxil [bis(POM)-PMEA] available as PREVON® from Gilead Sciences; lobucavir (BMS-180194), a nucleoside reverse transcriptase inhibitor disclosed in EP-0358154 and EP-0736533 and under development by Bristol-Myers Squibb; BCH-10652, a reverse transcriptase inhibitor (in the form of a racemic mixture of BCH-10618 and BCH-10619) under development by Biochem Pharma; emitricitabine [(−)-FTC] licensed from Emory University under U.S. Pat. No. 5,814,639 and under development by Triangle Pharmaceuticals; beta-L-FD4 (also called beta-L-D4C and named beta-L-2',3'-dicleoxy-5-fluorocytidene) licensed by Yale University to Vion Pharmaceuticals; DAPD, the purine nucleoside, (−)-b-D-2,6-diamino-purine dioxolane disclosed in EP-0656778 and licensed by Emory University and the University of Georgia to Triangle Pharmaceuticals; and lodenosine (FddA), 9-(2,3-dideoxy-2-fluoro-b-D-threo-pentofuranosyl)adenine, an acid stable purine-based reverse transcriptase inhibitor discovered by the NIH and under development by U.S. Bioscience Inc.

Typical suitable NNRTIs include nevirapine (BI-RG-587) available as VIRAMUNE® from Roxane Laboratories; delaviradine (BHAP, U-90152) available as RESCRIPTOR® from Pfizer; efavirenz (DMP-266) a benzoxazin-2-one disclosed in WO94/03440 and available as SUSTIVA® from Bristol-Myers Squibb Co.; PNU-142721, a furopyridine-thio-pyrimidine under development by Pfizer 08807; AG-1549 (formerly Shionogi #S-1153); 5-(3,5-dichlorophe-nyl)-thio-4-isopropyl-1-(4-pyridyl) methyl-1H-imidazol-2-ylmethyl carbonate disclosed in WO 96/10019 and under development by Agouron Pharmaceuticals, Inc.; MKC-442 (1-(ethoxy-methyl)-5-(1-methylethyl)-6-(phenylmethyl)-(2, 4(1H,3H) -pyrimidinedione) discovered by Mitsubishi Chemical Co. and under development by Triangle Pharmaceuticals; and (+)-calanolide A (NSC-675451) and B, coumarin derivatives disclosed in NIH U.S. Pat. No. 5,489,697, licensed to Med Chem Research, which is co-developing (+) calanolide A with Vita-invest as an orally administrable product.

Typical suitable PIs include saquinavir (Ro 31-8959) available in hard gel capsules as IVIRASE® and as soft gel capsules as FORTOVASE® from Roche Pharmaceuticals, Nutley, N.J. 07110-1199; ritonavir (ABT-538) available as NORVIR® from Abbott Laboratories; indinavir (MK-639) available as CRIXIVAN® from Merck & Co., Inc.; nelfiavir (AG-1343) available VIRACEPT® from Agouron Pharmaceuticals, Inc.; amprenavir (141W94), AGENERASE®, a non-peptide protease inhibitor under development by Vertex Pharmaceuticals, Inc. and available from Glaxo-Wellcome, under an expanded access program; lasinavir (BMS-234475) available from Bristol-Myers Squibb; DMP-450, a cyclic urea discovered by Dupont and under development by Triangle Pharmaceuticals; BMS-2322623, an azapeptide under development by Bristol-Myers Squibb as a 2nd-generation HIV-1 PI; ABT-378 under development by Abbott; and AG-1549 an orally active imidazole carbamate discovered by Shionogi and under development by Agouron Pharmaceuticals, Inc.

Other antiviral agents include hydroxyurea, ribavirin, IL-2, IL-12, pentafuside. Hydroxyurea (Droxia), a ribonucleoside triphosphate reductase inhibitor, the enzyme involved in the activation of T-cells, was discovered at the NCI and is in preclinical studies, it was shown to have a synergistic effect on the activity of didanosine and has been studied with stavudine. IL-2 is disclosed in Ajinomoto EP-0142268, Takeda EP-0176299, and Chiron U.S. Pat. Nos. RE 33,653, 4,530,787, 4,569,790, 4,604,377, 4,748,234, 4,752,585, and 4,949,314, and is available under the PROLEUKIN® (aldesleukin) as a lyophilized powder for IV infusion or sc administration upon reconstitution and dilution with water; a dose of about 1 to about 20 million 1 U/day, sc is preferred; a dose of about 15 million 1 U/day, sc is more preferred. IL-12 is disclosed in WO96/25171 and is administered in a dose of about 0.5 microgram/kg/day to about 10 microgram/kg/day, sc is preferred. Pentafuside (FUZEON®) a 36-amino acid synthetic peptide, disclosed in U.S. Pat. No. 5,464,933 that acts by inhibiting fusion of HIV-1 to target membranes. Pentafuside (3-100 mg/day) is given as a continuous sc infusion or injection together with efavirenz and 2 PI's to HIV-1 positive patients refractory to a triple combination therapy; use of 100 mg/day is preferred. Ribavirin, 1-.beta.-D-ribofuranosyl-1H-1,2,4-triazole-3-carboxamide, is available from ICN Pharmaceuticals, Inc., Costa Mesa, Calif.; its manufacture and formulation are described in U.S. Pat. No. 4,211,771.

In addition to the potential for CCR5 modulators in the management of HIV infections, the CCR5 receptor is an important regulator of immune function and compounds of the present invention may prove valuable in the treatment of disorders of the immune system. Treatment of solid organ transplant rejection, graft v. host disease, arthritis, rheumatoid arthritis, inflammatory bowel disease, atopic dermatitis, psoriasis, asthma, allergies or multiple sclerosis by administering to a human in need of such treatment an effective amount of a CCR5 antagonist compound of the present invention is also possible.

The pharmacokinetic challenges associated with large molecules, proteins and peptides resulted in the establishment of programs to identify low molecular weight antagonists of CCR5. The efforts to identify chemokine modulators have been reviewed (W. Kazmierski et al. *Biorg Med. Chem.* 2003 11:2663-76; L. Agrawal and G. Alkhatib, *Expert Opin. Ther. Targets* 2001 5(3):303-326; *Chemokine CCR5 antagonists incorporating* 4-*aminopiperidine scaffold, Expert Opin. Ther. Patents* 2003 13(9):1469-1473; M. A. Cascieri and M. S. Springer, *Curr. Opin. Chem. Biol.* 2000 4:420-426, and references cited therein)

Takeda's program was the first to lead to fruition with the identification of TAK-779 (M. Shiraishi et al., *J. Med. Chem.* 2000 43(10):2049-2063). Schering has advanced Sch-351125 into Phase I/II clinical studies and reported the advance of a more potent follow up compound, Sch417690 into Phase I studies. (S. W. McCrombie et al., WO00066559; B. M. Baroudy et al. WO00066558; A. Palani et al., *J Med. Chem.* 2001 44(21):3339-3342; J. R. Tagat et al., *J. Med. Chem.* 2001 44(21):3343-3346; J. A. Esté, *Cur. Opin. Invest. Drugs* 2002 3(3):379-383).

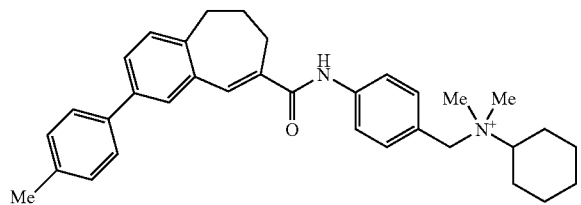

TAK-779

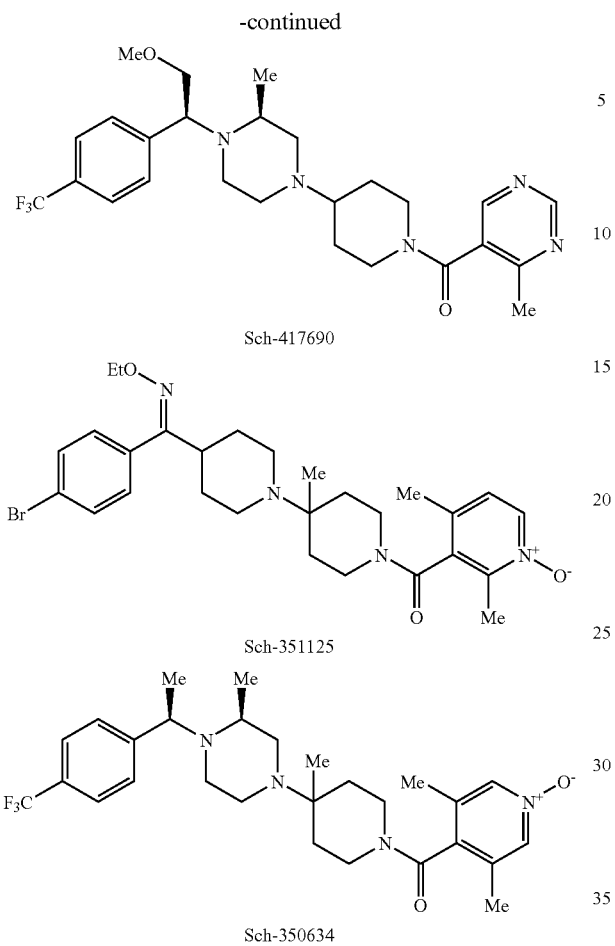

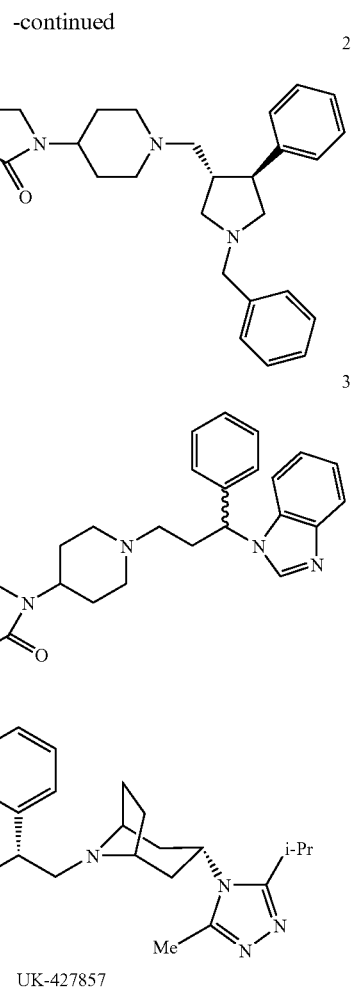

Merck has disclosed the preparation of (2S)-2-(3-chlorophenyl)-1-N-(methyl)-N-(phenylsulfonyl)amino]-4-[spiro(2,3-dihydrobenzothiophene-3,4'-piperidin-1'-yl)butane S-oxide (1) and related derivatives, trisubstituted pyrrolidines 2 and substituted piperidines 3 with good affinity for the CCR5 receptor and potent-HIV activity. (P. E. Finke et al., *Bioorg. Med. Chem. Lett.,* 2001 11:265-270; P. E. Finke et al., *Bioorg. Med. Chem. Lett.,* 2001 11:2469-2475; P. E. Finke et al., *Bioorg. Med. Chem. Lett.,* 2001 11:2475-2479; J. J. Hale et al., *Bioorg. Med. Chem. Lett.,* 2001 11:2741-22745; D. Kim et al., *Bioorg. Med. Chem. Lett.,* 2001 11:3099-3102)

WO0039125 (D. R. Armour et al.) and WO0190106 (M. Perros et al.) disclose heterocyclic compounds that are potent and selective CCR5 antagonists. UK-427857 has advanced to clinical trials and show activity against HIV-1 isolates and laboratory strains (M. J. Macartney et al., 43rd Intersci. Conf. Antimicrob. Agents Chemother. Sep. 14-17, 2003, Abstract H-875).

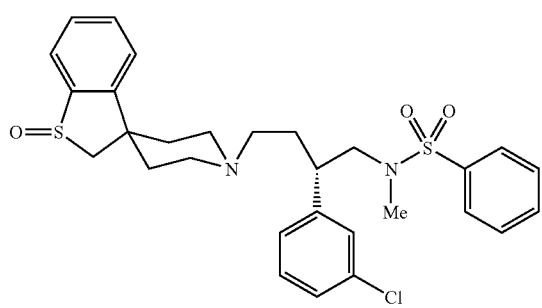

EP1236726 (H. Habashita et al.) discloses triazaspiro[5.5] undecane derivatives exemplified by AK602 which modulate the cytokine receptors. The compounds fall outside the scope of the current invention. (H. Nakata et al. Poster 546a, 11th Conference on Retroviruses and Opportunistic Infections, San Francisco, Calif., Feb. 8-11, 2004; other analogs have also been disclosed, see, e.g. K. Maeda et al., *J. Biol. Chem.* 2001 276(37): 35194-35200)

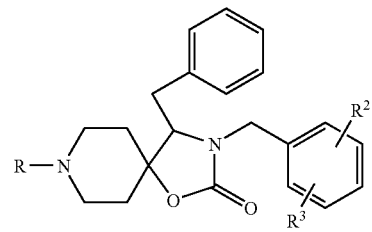

4

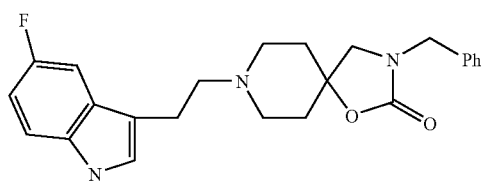

5

WO03/057698 (N. Schlienger) describe 1-oxa-3,8-diaza-spiro[4.5]decan-2-one compounds. More specifically identified are 3,4-di(optionally substituted)benzyl-1-oxa-3,8-diaza-spiro[4.5]decan-2-one compounds 4 where R is alkyl optionally substituted by a cycloalkyl, heterocyclic, heteroaryl or aryl ring. The compounds of the invention modulate monoamine receptors with selectively for the 5HT2A receptor. The reference further teaches, but does not exemplify bicyclic compounds wherein $R^2$ and $R^3$ together are an alkylene chain. These 1-oxa-3,8-diaza-spiro[4.5]decan-2-ones compounds and methods do not fall within the scope of the present invention. 1-Oxa-3,8-diazaspiro[4.5]decan-2-ones 5, and 1,3,8-triazaspiro[4.5]decan-2-ones have been disclosed that are tachykinin $NK_a$ receptor antagonists (P. W. Smith et al., *J. Med. Chem.* 1995 38(19):3772-79). Other 1-oxa-3,8-diaza-spiro[4.5]decan-2-ones compounds have been disclosed with α-adrenergic blocking activity (J. M. Caroon et al., *J. Med. Chem.* 1981 24(11):1320; R. M. Clark et al., *J. Med. Chem.* 1983 26(6):855-861). U.S. Pat. No. 3,399,192 (G. Regnier et al.) discloses 1-oxa-3,8-diaza-spiro[4.5]decan-2-ones compounds with analgesic, anti-inflammatory CNS depressant and bronchodilator activity. EP414422 (E. Toth et al.) discloses 1-oxa-3,8-diaza-spiro[4.5]decan-2-one compounds useful as antiallergic and psychotropic agents.

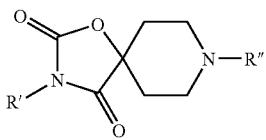

6

JP 63208590 (Yamanouchi Pharmaceuticals KK) disclose 1-oxa-3,8-diaza-spiro[4.5]decane-2,4-dione compounds 6 useful for treating CNS disorders. WO 2002102313 (J. Guo discloses pyrimidine compounds containing the 1-oxa-3,8-diaza-spiro[4.5]decane-2,4-dione radical useful for inhibiting phosphodiesterase. These compounds fall outside the scope of the present invention.

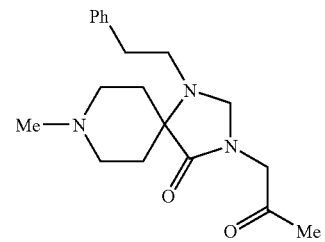

7

1,3,8-Triaza-spiro[4.5]decan-4-one compounds 7 have be disclosed block binding at the bradykinin B2 receptor and antagonize bradykinin mediated actions in vivo (B. J. Mavunkel et al. *J. Med. Chem.* 1996 39(16):3169-73). Other related 1-oxa-3,8-diaza-spiro[4.5]decan-2-ones have been disclosed: GB 1478932 (G. Regnier et al.) as anti-anaphylactic and bronchodilating compounds; J. Maillard, *Eur. J. Med. Chem.* 1974 9(2):128-132 as adrenolytic compounds; J. Maillard, *Chim. Ther.* 1972 7(6):458-466; J. Maillard, *J. Med. Chem.* 1972 15(11):1123-1128 as analgetic and adrenolytic compounds; U.S. Pat. No. 3,721,675 (J. Maillard). 1-oxa-3,9-diazaspiro[5.5]undecan-2-ones also were disclosed to have neuroleptic activity (J. Maillard, *Eur. J. Med. Chem.* 1974 9(4):416-423). WO200130780 (R. M. Scarborough et al.) and WO9711940 (J. M. Fisher) disclose compounds which generically encompass the 1-oxa-3,8-diaza-spiro[4.5]decan-2-one ring system as inhibitors of thrombosis and platelet aggregation. WO9965494 (M. W. Embry et al.) disclose oxadiaza- and triazaspiro[4.5]decylmethylimidazoles and analogs as inhibitors of prenyl-protein transferase.

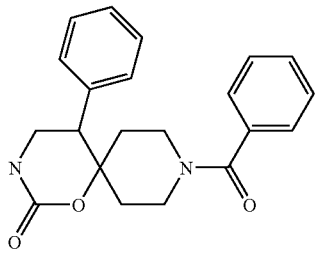

8

WO200292604 (H. Cai et al.) disclose compounds related to 9-benzoyl-5-phenyl-1-oxa-3,9-diaza-spiro[5.5]undecan-2-ones 8 which are useful for the treatment of diseases associated with the neurokinin 1 receptor. WO9711940 (M. J. Fisher et al.) disclose 1-oxa-3,9-diaza-spiro[5.5]undecan-2-one compounds as inhibitors of fibrinogen-mediated platelet aggregation. WO200157044 (H. Horino et al.) discloses fused 1-oxa-3,9-diazaispiro[5.5]undecan-2-ones which are monocyte chemotactic protein-1 (MCP-1 antagonists) 4-Substituted-1-oxa-3,9-diazaispiro[5.5]undecan-2-ones compounds have been disclosed which are claimed to have neuroleptic properties (J. Bassus et al. *Eur. J. Med. Chem.* 1974 9(4):416-423) These compounds fall outside the scope of the present invention.

SUMMARY OF THE INVENTION

The present invention relates to a compounds according to formulae Ia or Ib, methods for treating diseases alleviated by administration of a compound according to formulae Ia or Ib that is a CCR5 antagonists and pharmaceutical compositions for treating diseases containing a compound according to formulae Ia or Ib admixed with at least one carrier, diluent or excipient,

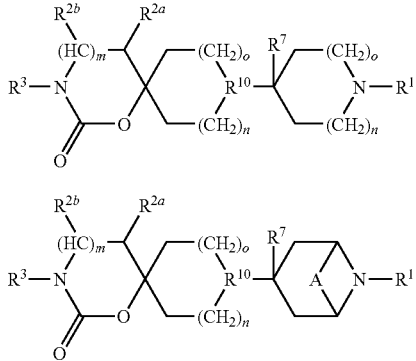

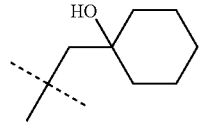

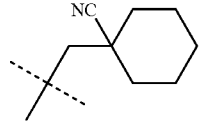

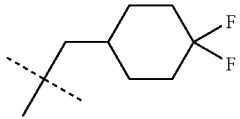

wherein:
A is $(CH_2)_q$;
$R^1$ is $C(=O)R^4$, $C(=O)X$, or $S(O)_p$;
X is $NR^5R^6$ or $OR^{11}$;
$R^{2a}$ and $R^{2b}$ are (A), independently
  (i) hydrogen,
  (ii) $C_{1-10}$ alkyl,
  (iii) $C_{2-10}$ alkenyl
  (iv) $C_{1-10}$ haloalkyl,
  (v) $C_{3-7}$ cycloalkyl,
  (vi) $C_{3-7}$ cycloalkyl-$C_{1-3}$ alkyl,
  (vii) $C_{1-10}$ heteroalkyl,
  (viii) $C_{1-10}$ alkylidene,
  (ix) $C_{1-10}$ heteroalkylidene,
  (x) aryl,
  (xi) aryl-$C_{1-3}$ alkyl,
  (xii) heteroaryl,
  (xiii) heteroaryl-$C_{1-3}$ alkyl,
  (xiv) $C_{1-10}$ alkyl wherein 2 or 3 nonadjacent carbon atoms are independently replaced with —O—, —S(O)$_p$—, —NH— or NR,
  (xv) —$(CH_2)_wR^8$ wherein w is an integer form 2 to 6, and the $C_2$-$C_6$ alkylene chain optionally contains a double bond;
  (xvi) —$(CH_2)_wCH=NR^9$ wherein w is an integer from 2 to 6; or
(B), together with the carbon atoms to which they are attached, are o-phenylene optionally substituted with 1 to 3 substituents independently selected from the group consisting of $C_{1-6}$ alkyl, $C_{1-6}$ haloalkyl, $C_{1-6}$ alkoxy, $C_{1-6}$ thioalkyl, $C_{1-6}$ alkylsulfonyl, hydroxyl, halogen, $NR^{5a}R^{6a}$, cyano and nitro with the proviso that if $R^{2a}$, $R^{2b}$, together with the carbon atoms to which they are optionally substituted o-phenylene, m is 1;
$R^3$ is (i) $C_{1-10}$ alkyl,
  (ii) $C_{2-10}$ alkenyl
  (iii) $C_{1-10}$ heteroalkyl,
  (iv) $C_{3-7}$ cycloalkyl,
  (v) $C_{1-6}$ alkyl-$C_{3-7}$ cycloalkyl,
  (vi) heterocycle $C_{1-6}$ alkyl,
  (vii) aryl,
  (viii) aryl-$C_{1-3}$ alkyl,
  (ix) heteroaryl,
  (x) heteroaryl $C_{1-6}$ alkyl,
  (xi) $C(=O)R^{3a}$ wherein $R^{3a}$ is $C_{1-10}$ alkyl, $C_{2-10}$ alkenyl or $C_{3-7}$ cycloalkyl, or
  (xii) a fragment of formula IIa-IIc;

$R^4$ is (i) $C_{1-10}$ alkyl,
  (ii) $C_{3-7}$ cycloalkyl-$C_{1-10}$ substituted alkyl,
  (iii) heterocycle,
  (iv) aryl, or
  (v) heteroaryl;
$R^5$ and $R^6$ are (A) when taken independently are hydrogen, $C_{1-10}$ alkyl, $C_{1-10}$ heteroalkyl, $C_{3-7}$ cycloalkyl, $C_{1-6}$ alkyl-$C_{3-7}$ cycloalkyl, heterocycle $C_{1-6}$ alkyl, aryl, aryl-$C_{1-3}$ alkyl, heteroaryl or heteroaryl $C_{1-6}$ alkyl; or,
  (B) $C_{3-6}$ alkylene or $[(CH_2)_2]_2O$ when taken together;
$R^{5a}$ and $R^{6a}$ are (A) hydrogen, $C_{1-6}$ alkyl or $C_{1-6}$ alkylcarbonyl when taken independently, or,
  (B) $C_{3-6}$ alkylene or $[(CH_2)_2]_2O$ when taken together;
$R^7$ is hydrogen, cyano or $C_{1-6}$ alky;
$R^8$ is —CN, —$NO_2$, —$CONR^{5a}R^{6a}$, $COR^9$, —$NHSO_2C_{1-6}$ alkyl;
$R^9$ is OH or $C_{1-6}$ alkoxy;
$R^{10}$ is N or $N^+$—$O^-$;
$R^{11}$ is $C_{1-10}$ alkyl, $C_{1-10}$ heteroalkyl, $C_{3-7}$ cycloalkyl, $C_{1-6}$ alkyl-$C_{3-7}$ cycloalkyl, heterocycle $C_{1-6}$ alkyl, aryl, aryl-$C_{1-3}$ alkyl, heteroaryl or heteroaryl $C_{1-6}$ alkyl;
m is 0 or 1;
n is independently 0 to 2;
o is independently 0 or 1;
p is 0 to 2;
q is 1 to 3;
wherein,
  each said heteroaryl is independently selected from the group consisting of pyridyl, 1-oxy-pyridinyl, pyrimidyl, oxypyrimdyl, pyrazinyl, pyridazinyl, pyrrolyl, thienyl, furyl, imidazolyl, pyrazolyl, oxazolyl, thiazolyl, isoxazolyl, isothiazolyl indolinyl, N-Boc-indolinyl, quinolinyl, isoquinolinyl, benzofuranyl, 4,5,6,7-tetrahydrobenzofuranyl and 1,2,3,4-tetrahydroacridinyl;
  each said aryl and said heteroaryl are optionally independently substituted with 1 to 3 substituents selected from the group consisting of hydroxy, $C_{1-6}$ alkyl, $C_{1-6}$ haloalkyl, $C_{1-6}$ alkoxy, $C_{1-6}$ haloalkoxy, $C_{1-6}$ thioalkyl, aryl, aryl $C_{1-3}$ alkyl, aryloxy, heteroaryloxy, thioaryl, thioheteroaryl, aryl $C_{1-3}$ alkoxy, heteroaryl, heterocyclyl, heterocycle $C_{1-6}$ alkyl, $C_{1-6}$ alkylsulfonyl, —NIHSO$_2C_{1-6}$ alkyl, $SO_2NR^{5a}R^{6a}$, $(CH_2)_uCO_2R^9$, $(CH_2)_uCONR^{5a}R^{6a}$, —$X^1C(=O)X^2$, $C_{1-10}$ alkylcarbonyl, halogen, $NR^{5a}R^{6a}$, cyano, nitro and $C_{1-10}$ alkyl wherein 2 or 3 nonadjacent carbon atoms are independently replaced with —O—, —S(O)$_p$—, —NH— or NR$^5$, wherein u is an integer from 0 to 6, X$^1$ is NR$^{5b}$ or O; X$^2$ is NR$^5$R$^6$ or OR$^3$ and R$^{5b}$ is H or C$_{1-6}$ alkyl;

each said heterocycle is independently selected from the group consisting of pyrrolidinyl, 1-methyl-pyrrolidinyl, piperidinyl, morpholinyl, thiomorpholinyl, tetrahydrofuranyl, dioxolanyl and pyranyl optionally substituted with 1 to 3 substituents independently selected from the group consisting of hydroxy C$_{1-6}$ alkyl, C$_{1-6}$ haloalkyl, C$_{1-6}$ alkoxy, C$_{1-6}$ thioalkyl, C$_{1-6}$ alkylsulfonyl, halogen, NR$^{5a}$R$^{6a}$, cyano and nitro;

pure enantiomers, partially resolved enantiomers, racemic mixtures, pharmaceutically acceptable acid addition salts, hydrates and solvates thereof.

Compounds and compositions of the present invention are useful for treating diseases mediated by human immunodeficiency virus in humans. Compounds and compositions of the present invention also may be used for treatment of respiratory disorders, including adult respiratory distress syndrome (ARDS), bronchitis, chronic bronchitis, chronic obstructive pulmonary disease, cystic fibrosis, asthma, emphysema, rhinitis and chronic sinusitis. Conditions triggered, affected or are in any other way correlated with T-cell trafficking in different organs may be treated with compounds of the invention. Compounds of the present invention may be useful for the treatment of such conditions and in particular, but not limited to the following for which a correlation with CCR5 or CCR5 chemokines has been established: inflammatory bowel disease, including Crohn's disease and ulcerative colitis, multiple sclerosis, rheumatoid arthritis, graft rejection, in particular but not limited to kidney and lung allografts, endometriosis, type I diabetes, renal diseases, chronic pancreatitis, inflammatory lung conditions or chronic heart failure. For recent reviews of possible applications of chemokines and chemokine receptor blockers see: Cascieri, M. A., and Springer, M. S., *The chemokine/chemokine receptor family: potential and progress for therapeutic intervention*, Curr. Opin. Chem. Biol. 2000 4(4):420-7; A. E. I. Proudfoot *The Strategy of Blocking the Chemokine System to Combat Disease*, Immunol. Rev. 2000 177:246-256.

DETAILED DESCRIPTION OF THE INVENTION

In one embodiment of the present invention there is provided a compound according to formulae Ia or Ib wherein A, X, X$^1$, X$^2$, R$^1$, R$^{2a}$, R$^{2b}$, R$^3$, R$^4$, R$^5$, R$^{5a}$, R$^6$, R$^{6a}$, R$^7$, R$^1$, R$^9$, R$^{10}$, R$^{11}$, m, n, o, p, q, u, w, heteroaryl, substituted aryl, substituted heteroaryl and heterocycle are as defined hereinabove.

In another embodiment of the present invention there is provided a compound according to formulae Ia" or Ib" wherein A, X, R$^1$, R$^4$, R$^5$, R$^6$, R$^7$, R$^8$, R$^9$, R$^{11}$, m, n, o, p and q are as defined hereinabove, and wherein:

R$^{2a}$ and R$^{2b}$ are (A), independently hydrogen, C$_{1-10}$ alkyl, C$_{1-10}$ haloalkyl, C$_{3-7}$ cycloalkyl, C$_{1-3}$ alkyl-C$_{3-7}$ cycloalkyl, C$_{1-10}$ heteroalkyl, C$_{1-10}$ alkylidene, C$_{1-10}$ heteroalkylidene, —(CH$_2$)$_q$R$^8$, aryl, aryl-C$_{1-3}$ alkyl, heteroaryl, heteroaryl-C$_{1-3}$ alkyl, C$_{1-10}$ alkyl wherein 2 or 3 nonadjacent carbon atoms are independently replaced with —O—, —S(O)$_p$—, —NH— or NR$^5$, or (B), together with the carbon atoms to which they are attached, are o-phenylene optionally substituted with 1 to 3 substituents independently selected from the group consisting of C$_{1-6}$ alkyl, C$_{1-6}$ haloalkyl, C$_{1-6}$ alkoxy, C$_{1-6}$ thioalkyl, C$_{1-6}$ alkylsulfonyl, halogen, NR$^{5a}$R$^{6a}$, cyano and nitro with the proviso that if R$^{2a}$ and R$^{2b}$, together with the carbon atoms to which they are optionally substituted o-phenylene, m is 1;

R$^3$ is C$_{1-10}$ alkyl, C$_{1-10}$ heteroalkyl, C$_{3-7}$ cycloalkyl, C$_{1-6}$ alkyl-C$_{3-7}$ cycloalkyl, heterocycle C$_{1-6}$ alkyl, aryl, aryl-C$_{1-3}$ alkyl, heteroaryl, heteroaryl C$_{1-6}$ alkyl;

R$^{5a}$ and R$^{6a}$ are (A) hydrogen, C$_{1-6}$ alkyl or C$_{1-6}$ alkylcarbonyl when taken independently or (B) C$_{3-6}$ alkylene when together;

q is an integer from 1 to 3;

each said heteraryl is independently selected from the group consisting of pyridyl, pyrimidyl, pyrazinyl, pyridazinyl, pyrrolyl. thienyl, furyl, imidazolyl, pyrazolyl, oxazolyl, thiazolyl, isoxazolyl and isothiazolyl, each said aryl and said heteroaryl are optionally independently substituted with 1 to 3 substituents selected from the group consisting of hydroxy, C$_{1-6}$ alkyl, C$_{1-6}$ haloalkyl, C$_{1-6}$ alkoxy, C$_{1-6}$ thioalkyl, C$_{1-6}$ alkylsulfonyl, halogen, NR$^{5a}$R$^{6a}$, cyano and nitro;

each said heterocycle is independently selected from the group consisting of pyrrolidinyl, 1-methyl-pyrrolidinyl; piperidinyl, tetrahydrofuranyl, and pyranyl optionally substituted with 1 to 3 substituents independently selected from the group consisting of hydroxy C$_{1-6}$ alkyl, C$_{1-6}$ haloalkyl, C$_{1-6}$ alkoxy, C$_{1-6}$ thioalkyl, C$_{1-6}$ alkylsulfonyl, halogen, NR$^{5a}$R$^{6a}$, cyano and nitro.

In another embodiment of the present invention there is provided a compound according to formula Ic wherein R$^{2a}$ is C$_{1-10}$ alkyl, C$_{1-10}$ haloalkyl, C$_{3-7}$ cycloalkyl, C$_{3-7}$ cycloalkyl-C$_{1-3}$ alkyl, C$_{1-10}$ heteroalkyl, C$_{1-10}$ alkylidene, C$_{1-10}$ heteroalkylidene or C$_{1-10}$ alkyl wherein 2 or 3 nonadjacent carbon atoms are independently replaced with —O—, —S(O)$_p$—, —NH— or NR$^5$; R$^{2b}$ is hydrogen; R$^3$ is C$_{1-10}$ alkyl, C$_{3-7}$ cycloalkyl, C$_{1-6}$ alkyl-C$_{3-7}$ cycloalkyl, optionally substituted aryl, optionally substituted aryl-C$_{1-3}$ alkyl, optionally substituted heteroaryl, optionally substituted heteroaryl-C$_{1-6}$ alkyl; R$^4$ is C$_{1-10}$ alkyl, optionally substituted aryl or optionally substituted heteroaryl; R$^7$ is hydrogen or C$_{1-6}$ alkyl; n and o are 1; p is 2; and X, X$^1$, X$^2$, R$^1$, R$^5$, R$^{5a}$, R$^6$, R$^{6a}$, R$^9$, R$^{10}$, R$^{11}$, m, u, heteroaryl, substituted aryl, substituted heteroaryl and heterocycle are as defined hereinabove.

In another embodiment of the present invention there is provided a compound according to formula Ic wherein R$^{2a}$ is C$_{1-10}$ alkyl, C$_{1-10}$ haloalkyl, C$_{3-7}$ cycloalkyl, C$_{3-7}$ cycloalkyl-C$_{1-3}$ alkyl, C$_{1-10}$ heteroalkyl, C$_{1-10}$ alkylidene, C$_{1-10}$ heteroalkylidene or C$_{1-10}$ alkyl wherein 2 or 3 nonadjacent carbon atoms are independently replaced with —O—, —S(O)$_p$—, —NH— or NR$^5$; R$^{2b}$ is hydrogen; R$^3$ is C$_{1-10}$ alkyl, C$_{3-7}$ cycloalkyl, C$_{1-6}$ alkyl-C$_{3-7}$ cycloalkyl, optionally substituted aryl, optionally substituted aryl-C$_{1-3}$ alkyl, optionally substituted heteroaryl, optionally substituted heteroaryl-C$_{1-6}$ alkyl; R$^4$ is C$_{1-10}$ alkyl, optionally substituted aryl or optionally substituted heteroaryl; R$^7$ is hydrogen or methyl; p is 2; and X, X$^1$, X$^2$, R$^1$, R$^5$, R$^{5a}$, R$^6$, R$^{6a}$, R$^9$, R$^{10}$, R$^{11}$, m, u, heteroaryl, substituted aryl, substituted heteroaryl and heterocycle are as defined hereinabove.

In another embodiment of the present invention there is provided a compound according to formula Ic wherein R$^1$ is COR$^4$; R$^{2a}$ is C$_{1-10}$ alkyl, C$_{1-10}$ heteroalkyl or C$_{1-10}$ alkyl wherein 2 or 3 nonadjacent carbon atoms in the alkyl chain optionally can be independently replaced with —O—, —S(O)$_p$—, —NH— or NR$^5$; R$^{2b}$ is hydrogen; R$^3$ is C$_{1-10}$ alkyl, C$_{3-7}$ cycloalkyl, C$_{1-6}$ alkyl-C$_{3-7}$ cycloalkyl, optionally substituted aryl, optionally substituted aryl-C$_{1-3}$ alkyl, optionally substituted heteroaryl, optionally substituted heteroaryl-C$_{1-6}$ alkyl; R$^4$ is optionally substituted aryl or optionally substituted heteroaryl; R$^7$ is hydrogen or methyl; R$^{10}$ is N; p is 2; and, $X^1$, X, $R^5$, $R^{5a}$, $R^6$, $R^{6a}$, $R^9$, m, u, heteroaryl, substituted aryl, substituted heteroaryl and heterocycle are as defined hereinabove.

In another embodiment of the present invention there is provided a compound according to formula Ic wherein $R^1$ is $COR^4$; $R^{2a}$ is $C_{1-10}$ alkyl, $C_{1-10}$ heteroalkyl or $C_{1-10}$ alkyl wherein 2 or 3 nonadjacent carbon atoms in the alkyl chain optionally can be independently replaced with —O—, —S(O)$_p$—, —NH— or $NR^5$; $R^{2b}$ is hydrogen; $R^3$ is $C_{1-10}$ alkyl, $C_{3-7}$ cycloalkyl, $C_{1-6}$ alkyl-$C_{3-7}$ cycloalkyl, optionally substituted aryl, optionally substituted aryl-$C_{1-3}$ alkyl, optionally substituted heteroaryl, optionally substituted heteroaryl-$C_{1-6}$ alkyl; $R^4$ is optionally substituted aryl; $R^7$ is hydrogen or methyl; $R^{10}$ is N; p is 2; and $X^1$, $X^2$, $R^5$, $R^{5a}$, $R^6 R^{6a}$, $R^9$, m, u, heteroaryl, substituted aryl, substituted heteroaryl and heterocycle are as defined hereinabove.

In another embodiment of the present invention there is provided a compound according to formula Ic wherein $R^1$ is $COR^4$; $R^{2a}$ is $C_{1-10}$ alkyl, $C_{1-10}$ heteroalkyl or $C_{1-10}$ alkyl wherein 2 or 3 nonadjacent carbon atoms in the alkyl chain optionally can be independently replaced with —O—, —S(O)$_p$—, —NH— or $NR^5$; $R^{2b}$ is hydrogen; $R^3$ is $C_{1-10}$ allyl, $C_{3-7}$ cycloalkyl, $C_{1-6}$ alkyl-$C_{3-7}$ cycloalkyl, optionally substituted aryl, optionally substituted aryl-$C_{1-3}$ alkyl, optionally substituted heteroaryl, optionally substituted heteroaryl-$C_{1-6}$ alkyl; $R^4$ is optionally substituted phenyl, 1-naphthyl or 2-naphthyl; $R^7$ is hydrogen or methyl; $R^{10}$ is N; p is 2; and $X^1$, $X^2$, $R^5$, $R^{5a}$, $R^6$, $R^{6a}$, $R^9$, m, u, heteroaryl, substituted aryl, substituted heteroaryl and heterocycle are as defined hereinabove.

In another embodiment of the present invention there is provided a compound according to formula Ic wherein $R^1$ is $COR^4$; $R^{2a}$ is $C_{1-10}$ alkyl, $C_{1-10}$ heteroalkyl or $C_{1-10}$ alkyl wherein 2 or 3 nonadjacent carbon atoms in the alkyl chain optionally can be independently replaced with —O—, —S(O)$_p$—, —NH— or $NR^5$; $R^{2b}$ is hydrogen; $R^3$ is $C_{1-10}$ alkyl, $C_{3-7}$ cycloalkyl, $C_{1-6}$ alkyl-$C_{3-7}$ cycloalkyl, optionally substituted aryl, optionally substituted aryl-$C_{1-3}$ alkyl, optionally substituted heteroaryl, optionally substituted heteroaryl-$C_{1-6}$ alkyl; $R^4$ is optionally substituted heteroaryl; $R^7$ is hydrogen or methyl; $R^{10}$ is N; p is 2; $X^1$, $X^2$, $R^5$, $R^{5a}$, $R^6$, $R^{6a}$, $R^9$, m, u, heteroaryl, substituted aryl, substituted heteroaryl and heterocycle are as defined hereinabove.

In another embodiment of the present invention there is provided a compound according to formula Ic wherein $R^1$ is $COR^4$; $R^{2a}$ is $C_{1-10}$ alkyl, $C_{1-10}$ heteroalkyl or $C_{1-10}$ alkyl wherein 2 or 3 nonadjacent carbon atoms in the alkyl chain optionally can be independently replaced with —O—, —S(O)$_p$—, —NH— or $NR^5$; $R^{2b}$ is hydrogen; $R^3$ is $C_{1-10}$ alkyl, $C_{3-7}$ cycloalkyl, $C_{1-6}$ alkyl-$C_{3-7}$ cycloalkyl, optionally substituted aryl, optionally substituted aryl-$C_{1-3}$ alkyl, optionally substituted heteroaryl, heteroaryl-$C_{1-6}$ alkyl; $R^4$ is optionally substituted pyridyl, optionally substituted pyrimidyl, optionally substituted pyrazolyl, optionally substituted oxazolyl, optionally substituted isoxazolyl or optionally substituted pyrrolyl; $R^7$ is hydrogen or methyl; $R^{10}$ is N; p is 2; $X^1$, $X^2$, $R^5 R^{5a}$, $R^6$, $R^{6a}$, $R^9$, m, u, heteroaryl, substituted aryl, substituted heteroaryl and heterocycle are as defined hereinabove.

In another embodiment of the present invention there is provided a compound according to formula 1d wherein $R^1$ is $COR^4$; $R^{2a}$ is $C_{1-10}$ alkyl, $C_{1-10}$ haloalkyl, $C_{3-7}$ cycloalkyl, $C_{3-7}$ cycloalkyl-$C_{1-3}$ alkyl, $C_{1-10}$ heteroalkyl, $C_{1-10}$ alkylidene, $C_{1-10}$ heteroalkylidene or $C_{1-10}$ alkyl wherein 2 or 3 nonadjacent carbon atoms are independently replaced with —O—, —S(O)$_p$—, —NH— or $NR^5$; $R^{2b}$ is hydrogen; $R^3$ is either as defined in claim 1 or in claim 2; $R^4$ is optionally substituted aryl or optionally substituted heteroaryl; $R^7$ is hydrogen or $C_{1-6}$ alkyl; n and o are 1; p is 2; A, $X^1$, $X^2$, $R^3$, $R^5$, $R^{5a}$, $R^6$, $R^{6a}$, $R^9$, $R^1$, m, q, u, heteroaryl, substituted aryl, substituted heteroaryl and heterocycle are as defined hereinabove.

In another embodiment of the present invention there is provided a compound according to formula Id wherein A is $(CH_2)_2$; $R^1$ is $COR^4$; $R^{2a}$ is $C_{1-10}$ alkyl, $C_{1-10}$ haloalkyl, $C_{3-7}$ cycloalkyl, $C_{3-7}$ cycloalkyl-$C_{1-3}$ alkyl, $C_{1-10}$ heteroalkyl, $C_{1-10}$ alkylidene, $C_{1-10}$ heteroalkylidene or $C_{1-10}$ alkyl wherein 2 or 3 nonadjacent carbon atoms are independently replaced with —O—, —S(O)$_p$—, —NH— or $NR^5$; $R^{2b}$ is hydrogen; $R^3$ is either as defined in claim 1 or in claim 2; $R^4$ is optionally substituted aryl or optionally substituted heteroaryl; $R^7$ is hydrogen or $C_{1-6}$ alkyl; n and o are 1; p is 2; $X^1$, $X^2$, $R^3$, $R^5$, $R^{5a}$, $R^6$, $R^{6a}$, $R^9$, $R^{10}$, m, q, u, heteroaryl, substituted aryl, substituted heteroaryl and heterocycle are as defined hereinabove.

In another embodiment of the present invention there is provided a compound according to formula Ie wherein $R^{2a}$ and $R^{2b}$ are optionally substituted o-phenylene; $R^3$ is $C_{1-10}$ alkyl, $C_{3-7}$ cycloalkyl, $C_{1-6}$ alkyl-$C_{3-7}$ cycloalkyl, optionally substituted aryl, optionally substituted aryl-$C_{1-3}$ alkyl, optionally substituted heteroaryl, optionally substituted heteroaryl-$C_{1-3}$ alkyl; $R^4$ is optionally substituted aryl or optionally substituted heteroaryl; $R^7$ is hydrogen or $C_{1-6}$ alkyl; $R^{12}$ in each occurrence is independently hydroxy, $C_{1-6}$ alkyl, $C_{1-6}$ haloalkyl, $C_{1-6}$ alkoxy, $C_{1-6}$ thioalkyl, $C_{1-6}$ alkylsulfonyl, halogen, $NR^{5a}R^{6a}$, cyano and nitro; m is 1; n and o are 1; p is 2; and, $R^1$, $R^5$, $R^{5a}$, $R^6$, $R^{6a}$, $R^9$, $R^{10}$, u, heteroaryl, substituted aryl, substituted heteroaryl and heterocycle are as defined hereinabove.

In another embodiment of the present invention there is provided a compound according to formulae Ia or Ib selected from:

5-Butyl-9-[1-(4,6-dimethyl-2-trifluoromethyl-pyrimidine-5-carbonyl)-4-methyl-piperidin-4-yl]-3-(tetrahydro-pyran-4-ylmethyl)-1-oxa-3,9-diaza-spiro[5.5]undecan-2-one; compound with trifluoro-acetic acid 5-Butyl-9-[1-(4,6-dimethyl-pyrimidine-5-carbonyl)-4-methyl-piperidin-4-yl]-3-(tetrahydro-pyran-4-ylmethyl)-1-oxa-3,9-diaza-spiro[5.5]undecan-2-one; compound with trifluoro-acetic acid 5-Butyl-3-(4,4-difluoro-cyclohexylmethyl)-9-[1-(4,6-dimethyl-2-trifluoromethyl-pyrimidine -5-carbonyl)-4-methyl-piperidin-4-yl]-1-oxa-3,9-diaza-spiro[5.5]undecan-2-one; compound with trifluoro-acetic acid 5-Butyl-3-(4,4-difluoro-cyclohexylmethyl)-9-[1-(4,6-dimethyl-pyrimidine-5-carbonyl)-4-methyl-piperidin-4-yl]-1-oxa-3,9-diaza-spiro[5.5]undecan-2-one; compound with trifluoro-acetic acid 5-Butyl-9-{1-[1-(4-fluoro-phenyl)-3,5-dimethyl-1H-pyrazole-4-carbonyl]-4-methyl-piperidin-4-yl}-3-(tetrahydro-pyran-4-ylmethyl)-1-oxa-3,9-diaza-spiro[5.5]undecan-2-one; compound with trifluoro-acetic acid 5-Butyl-9-{1-[3-(4-methoxy-phenyl)-5-methyl-isoxazole-4-carbonyl]-4-methyl-piperidin-4-yl}-3-(tetrahydro-pyran-4-ylmethyl)-1-oxa-3,9-diaza-spiro[5.5]undecan-2-one; compound with trifluoro-acetic acid (S)-5-Butyl-3-cyclohexylmethyl-9-[1-(2,6-dimethyl-benzoyl)-piperidin-4-yl]-1-oxa-3,9-diaza-spiro[5.5]undecan-2-one (R)-5-Butyl-3-cyclohexylmethyl-9-[1-(2,6-dimethyl-benzoyl)-piperidin-4-yl]-1-oxa-3,9-diaza-spiro[5.5]undecan-2-one 5-Butyl-3-cyclohexylmethyl-9-[1-(4,6-dimethyl-pyrimidine-5-carbonyl)-4-methyl-piperidin-4-yl]-1-oxa-3,9-diaza-spiro[5.5]undecan-2-one; compound with trifluoro-acetic acid 5-Butyl-9-[1-(2,6-dimethyl-benzoyl)-piperidin-4-yl]-3-(tetrahydro-pyran-4-ylmethyl) -1-oxa-3,9-diaza-spiro[5.5]undecan-2-one; compound with trifluoro-acetic acid 5-Butyl-3-cyclohexylmethyl-9-[1-(4,6-dimethyl-pyrimidine-5-carbonyl)-piperidin-4-yl]-1-oxa-3,9-diaza-spiro[5.5]undecan-2-one; compound with trifluoro-acetic acid 5-Butyl-3-cyclohexylmethyl-9-[1-(2,6-dimethyl-benzoyl)-piperidin-4-yl]-1-oxa-3,9-diaza-spiro[5.5]undecan-2-one; compound with trifluoro-acetic acid 5-Butyl-9-[1-(4,6-dimethyl-pyrimidine-5-carbonyl)-piperidin-4-yl]-3-(tetrahydro-pyran-4-ylmethyl)-1-oxa-3,9-diaza-spiro[5.5]undecan-2-one; compound with trifluoro-acetic acid In another embodiment of the present invention there is provided a method for treating or preventing an human immunodeficiency virus (HIV) infection, or treating AIDS or ARC, in a patient in need thereof which comprises administering to the patient a therapeutically effective amount of a compound according to formulae Ia or Ib wherein A, X, $X^1$, $X^2$, $R^1$, $R^{2a}$, $R^{2b}$, $R^3$, $R^4$, $R^5$, $R^{5a}$, $R^6$, $R^{6a}$, $R^7$, $R^8$, $R^9$, $R^{10}$, $R^{11}$, m, n, o, p, q, u, w, heteroaryl, substituted aryl, substituted heteroaryl and heterocycle are as defined hereinabove.

In another embodiment of the present invention there is provided a method for treating a mammal having a disease mediated by human immunodeficiency virus comprising co-administering to a mammal, a CCR5 receptor antagonist of formulae Ia or Ib wherein A, X, $X^1$, $X^2$, $R^1$, $R^{2a}$, $R^{2b}$, $R^3$, $R^4$, $R^5$, $R^{5a}$, $R^6$, $R^{6a}$, $R^7$, $R^8$, $R^9$, $R^{10}$, $R^{11}$, m, n, o, p, q, u, w, heteroaryl, substituted aryl, substituted heteroaryl and heterocycle are as defined hereinabove and at least one compound selected from the group consisting of HIV nucleoside reverse transcriptase, HIV nonnucleoside reverse transcriptase, HIV protease inhibitor and viral fusion inhibitors.

In another embodiment of the present invention there is provided a method for treating a mammal having a disease mediated by human immunodeficiency virus comprising co-administering to a mammal, a CCR5 receptor antagonist of formulae Ia or Ib wherein A, X, $X^1$, $X^2$, $R^1$, $R^{2a}$, $R^{2b}$, $R^3$, $R^4$, $R^5$, $R^{5a}$, $R^6$, $R^{6a}$, $R^7$, $R^8$, $R^9$, $R^{10}$, $R^{11}$, m, n, o, p, q, u, w, heteroaryl, substituted aryl, substituted heteroaryl and heterocycle are as defined hereinabove and at least one reverse transcriptase inhibitor selected from the group consisting of zidovudine, lamivudine, didanosine, zalcitabine, stavudine, rescriptor, sustiva and viramune, efavirenz, nevirapine or delavirdine, and/or the nucleoside reverse transcriptase inhibitor selected from the group consisting of zidovudine, didanosin, zalcitabine, stavudine, lamivudine, abacavir, adefovir and dipivoxil, and/or the protease inhibitor selected from the group consisting of saquinavir, ritonavir, nelfinavir, indinavir, amprenavir, lopinavir.

In another embodiment of the present invention there is provided a method for treating a mammal having a disease state that is alleviated by treating the mammal with a CCR5 receptor antagonist wherein the disease state is solid organ transplant rejection, graft v. host disease, arthritis, rheumatoid arthritis, inflammatory bowel disease, atopic dermatitis, psoriasis, asthma, allergies or multiple sclerosis comprising co-administering a compound of formulae Ia or Ib wherein A, X, $X^1$, $X^2$, $R^1$, $R^{2a}$, $R^{2b}$, $R^3$, $R^4$, $R^5$, $R^{5a}$, $R^6$, $R^{6a}$, $R^7$, $R^8$, $R^9$, $R^{10}$, $R^{11}$, m, n, o, p, q, u, w, heteroaryl, substituted aryl, substituted heteroaryl and heterocycle are as defined hereinabove.

In another embodiment of the present invention there is provided a method for treating a human having a disease state that is alleviated by treating the human with a CCR5 receptor antagonist wherein the disease state is solid organ transplant rejection, graft v. host disease, arthritis, rheumatoid arthritis, inflammatory bowel disease, atopic dermatitis, psoriasis, asthma, allergies or multiple sclerosis comprising co-administering a compound of formulae Ia or Ib wherein A, X, $X^1$, $X^2$, $R^1$, $R^{2a}$, $R^{2b}$, $R^3$, $R^4$, $R^5$, $R^{5a}$, $R^6$, $R^{6a}$, $R^7$, $R^8$, $R^9$, $R^{10}$, $R^{11}$, m, n, o, p, q, u, w, heteroaryl, substituted aryl, substituted heteroaryl and heterocycle are as defined hereinabove, and at least one other immune modulator.

In another embodiment of the present invention there is provided a pharmaceutical composition comprising a compound according to formulae Ia or Ib wherein A, X, $X^1$, $X^2$, $R^1$, $R^{2a}$, $R^{2b}$, $R^3$, $R^4$, $R^5$, $R^{5a}$, $R^6$, $R^{6a}$, $R^7$, $R^8$, $R^9$, $R^{10}$, $R^{11}$, m, n, o, p, q, u, w, heteroaryl, substituted aryl, substituted heteroaryl and heterocycle are as defined hereinabove admixed with at least one pharmaceutical acceptable carrier, diluent or excipient.

DEFINITIONS

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined hereinabove" refers to the first definition provided in the Summary of the Invention.

The term "optional" or "optionally" as used herein means that a subsequently described event or circumstance may, but need not, occur, and that the description includes instances where the event or circumstance occurs and instances in which it does not. For example, "optionally substituted" means that the moiety may be hydrogen or a substituent.

It is contemplated that the definitions described herein may be appended to form chemically-relevant combinations, such as "heteroalkylaryl," "haloalkylheteroaryl," "arylalkylheterocyclyl," "alkylcarbonyl," "alkoxyalkyl," and the like.

The term "alkyl" as used herein denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-10}$ alkyl" as used herein refers to an alkyl composed of 1 to 10 carbons. Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, and octyl.

When the term "alkyl" is used as a suffix following another term, as in "phenylalkyl," or "hydroxyalkyl," this is intended to refer to an alkyl group, as defined above, being substituted with one to two substituents (preferably one substituent) selected from the other, specifically-named group. Thus, for example, "phenylalkyl" refers to an alkyl group having one to two phenyl substituents, and thus includes benzyl, phenylethyl, and biphenyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl)-3-hydroxypropyl, and so forth. Accordingly, as used herein, the term "hydroxyalkyl" is used to define a subset of heteroalkyl groups defined below.

The term "alkylidene" as used herein means a bivalent radical =CRR', wherein R and R' are independently alkyl radicals or hydrogen where alkyl is as defined herein.

Examples of alkylidenyl radicals include, but are not limited to, ethylidene, butylidene, pentylidene and 1-methyl-butylidene.

The term "alkenyl" or "alkene" as used herein denotes an unsubstituted hydrocarbon chain radical having from 2 to 10 carbon atoms having one or two olefinic double bonds. $C_{2-10}$ alkenyl" as used herein refers to an alkenyl composed of 2 to 10 carbons. Examples are vinyl, 1-propenyl, 2-propenyl (allyl) or 2-butenyl (crotyl). Examples of the corresponding alkene are ethane, 1-propene, 2-propene and 2-butene.

The term "haloalkyl" as used herein denotes an unbranched or branched chain alkyl group as defined above wherein 1, 2, 3 or more hydrogen atoms are substituted by a halogen. Examples are 1-fluoromethyl, 1-chloromethyl, 1-bromomethyl, 1-iodomethyl, trifluoromethyl, trichloromethyl, tribromomethyl, triiodomethyl, 1-fluoroethyl, 1-chloroethyl, 1-bromoethyl, 1-iodoethyl, 2-fluoroethyl, 2-chloroethyl, 2-bromoethyl, 2-iodoethyl, 2,2-dichloroethyl, 3-bromopropyl or 2,2,2-trifluoroethyl.

The term "cycloalkyl" as used herein denotes a saturated carbocyclic ring containing 3 to 8 carbon atoms, i.e. cyclopropyl, cyclobutyl, cyclopentyl, cyclohexyl, cycloheptyl or cyclooctyl. "$C_{3-7}$ cycloalkyl" as used herein refers to a cycloalkyl composed of 3 to 7 carbons in the carbocyclic ring.

The term "cycloalkyl alkyl" as used herein refers to the radical R'R"—, wherein R' is a cycloalkyl radical as defined herein, and R" is an alkylene radical as defined herein with the understanding that the attachment point of the cycloalkylalkyl moiety will be on the alkylene radical. Examples of cycloalkylalkyl radicals include, but are not limited to, cyclopropylmethyl, cyclohexylmethyl, cyclopentylethyl. $C_{3-7}$ cycloalkyl-$C_{1-3}$ alkyl refers to the radical R'R" where R' is $C_{3-7}$ cycloalkyl and R" is $C_{1-3}$ alkylene as defined herein.

The term "heteroalkyl" as used herein means an alkyl radical as defined herein wherein one, two or three hydrogen atoms have been replaced with a substituent independently selected from the group consisting of —$OR^a$, —$NR^bR^c$, and —$S(O)_nR^d$ (where n is an integer from 0 to 2), with the understanding that the point of attachment of the heteroalkyl radical is through a carbon atom, wherein $R^a$ is hydrogen, acyl, alkyl, cycloalkyl, or cycloalkylalkyl; $R^b$ and $R^c$ are independently of each other hydrogen, acyl, alkyl, cycloalkyl, or cycloalkylalkyl; and when n is 0, $R^d$ is hydrogen, alkyl, cycloalkyl, or cycloalkylalkyl, and when n is 1 or 2, $R^d$ is alkyl, cycloalkyl, cycloalkylalkyl, amino, acylamino, or alkylamino. Alternatively a heteroalkyl group is an alkyl radical wherein one or more of the carbon atoms is replaced by —O—, $NR^b$—, or —$S(O)_n$—. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

The term "alkylene" as used herein denotes a divalent saturated linear hydrocarbon radical of 1 to 10 carbon atoms or a branched saturated divalent hydrocarbon radical of 3 to 10 carbon atoms, unless otherwise indicated. Examples of alkylene radicals include, but are not limited to, methylene, ethylene, propylene, 2-methyl-propylene, butylene and 2-ethylbutylene.

The term "heteroalkylidenyl" or "heteroalkylidene" as used herein means a bivalent radical =CRR', wherein R is an heteroalkyl radical, an haloalkyl radical, an alkyl radical, or hydrogen, and R' is an heteroalkyl radical or an haloalkyl radical, as defined herein. Examples of heteroalkylidenyl radicals include, but are not limited to, 3,3,3-trifluoropropylidenyl, 2-hydroxybutylidenyl, 3-aminopropylidenyl, and the like.

The term "aryl" as used herein denotes a monovalent aromatic carbocyclic radical containing 5 to 15 carbon atoms consisting of one individual ring, or one or more fused rings in which at least one ring is aromatic in nature, which can optionally be substituted with one or more, preferably one or three substituents independently selected from hydroxy, thio, cyano, alkyl, alkoxy, lower haloalkoxy, alkylthio, halogen, haloalkyl, hydroxyalkyl, nitro, alkoxycarbonyl, amino, alkylamino, dialkylamino, aminoalkyl, alkylaminoalkyl, and dialkylaminoalkyl, alkylsulfonyl, arylsulfinyl, alkylaminosulfonyl, arylaminosulfonyl, alkylsulfonylamino, arylsulfonylamino, carbamoyl, alkylcarbamoyl and dialkylcarbamoyl, arylcarbamoyl, alkylcarbonylamino, arylcarbonylamino, unless otherwise indicated. Alternatively two adjacent atoms of the aryl ring may be substituted with a methylenedioxy or ethylenedioxy group. Examples of aryl radicals include, but are not limited to, phenyl, naphthyl, indanyl, anthraquinolyl tetrahydronaphthyl, 3,4-methylenedioxyphenyl, 1,2,3,4-tetrahydroquinolin-7-yl, 1,2,3,4-tetrahydroisoquinoline-7-yl, and the like.

The term "arylalkyl" or "aralkyl" as used herein denotes the radical R'R"—, wherein R' is an aryl radical as defined herein, and R" is an alkylene radical as defined herein with the understanding that the attachment point of the arylalkyl moiety will be on the alkylene radical. Examples of arylalkyl radicals include, but are not limited to, benzyl, phenylethyl and 3-phenylpropyl.

The term "aryloxy" as used herein denotes an O-aryl group, wherein aryl is as defined above. An aryloxy group can be unsubstituted or substituted with one or two suitable substituents. The term "phenoxy" refers to an aryloxy group wherein the aryl moiety is a phenyl ring.

The term "thioaryl" as used herein denotes an S-aryl group, wherein aryl is as defined above The term "heteroaryl" or "heteroaromatic" as used herein means a monocyclic or bicyclic radical of 5 to 12 ring atoms having at least one aromatic ring containing four to eight atoms per ring, incorporating one or more N, O, or S heteroatoms, the remaining ring atoms being carbon, with the understanding that the attachment point of the heteroaryl radical will be on an aromatic ring. As well known to those skilled in the art, heteroaryl rings have less aromatic character than their all-carbon counter parts. Thus, for the purposes of the invention, a heteroaryl group need only have some degree of aromatic character. Examples of heteroaryl moieties include monocyclic aromatic heterocycles having 5 to 6 ring atoms and 1 to 3 heteroatoms include, but is not limited to, pyridinyl, pyrimidyl, pyrazinyl, pyrrolyl, pyrazolyl, imidazolyl, oxazole, isoxazole, thiazole, isothiazole, triazoline, thiadiazole and oxadiaxoline which can optionally be substituted with one or more, preferably one or two substituents selected from hydroxy, cyano, alkyl, alkoxy, thio, lower haloalkoxy, alkylthio, halo, haloalkyl, alkylsulfinyl, alkylsulfonyl, halogen, amino, alkylamino, dialkylamino, aminoalkyl, alkylaminoalkyl, and dialkylaminoalkyl, nitro, alkoxycarbonyl and carbamoyl, alkylcarbamoyl, dialkylcarbamoyl, arylcarbamoyl, alkylcarbonylamino and arylcarbonylamino. Examples of bicyclic moieties include, but are not limited to, quinolinyl, isoquinolinyl, benzofuryl, benzothiophenyl, benzoxazole, benzisoxazole, benzothiazole and benzisothiazole. Bicyclic moieties can be optionally substituted on either ring.

The term "heteroaryloxy" as used herein means an —O-heteroaryl group, wherein "heteroaryl" is as defined above such as 3-pyridyloxy and 2-pyrimidinoxy.

The term "heteroarylalkyl" or "heteroaralkyl" means the radical of the formula R'R", wherein R' is an optionally substituted heteroaryl radical as defined herein, and R" is an alkylene radical as defined herein with the understanding that the attachment point of the heteroaryl radical will be on the alkylene radical. Examples of heteroarylalky radicals include, but are not limited to, 2-imidazolylmethyl, 3-pyrrolylethyl.

The term "heterocyclyl" or "heterocycle" as used herein denotes a monovalent saturated cyclic radical, consisting of one or more rings, preferably one to two rings, of three to eight atoms per ring, incorporating one or more ring heteroatoms (chosen from N, O or $S(O)_{0-2}$), and which can optionally be independently substituted with one or more, preferably one or two substituents selected from hydroxy, oxo, cyano, lower alkyl, lower alkoxy, lower haloalkoxy, alkylthio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, arylcarbonylamino, unless otherwise indicated. Examples of heterocyclic radicals include, but are not limited to, pyrrolidinyl, tetrahydrofuranyl, tetrahydrothiophenyl, oxazolidinyl, isoxazolidinyl, morpholinyl, piperazinyl, piperidinyl, tetrahydropyranyl, thiomorpholinyl, quinuclidinyl.

The term "alkoxy group" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an —O-alkyl wherein alkyl is $C_{1-10}$.

The term "alkylthio" or "thioalkyl" means an —S-alkyl group, wherein alkyl is as defined above such as meththio, ethylthio, n-propylthio, i-propylthio, n-butylthio, hexylthio, including their isomers. "Lower alkylthio" or "lower thioalkyl" as used herein denotes an alkylthio group with a "lower alkyl" group as previously defined. "$C_{1-10}$ alkylthio" as used herein refers to an —S-alkyl wherein alkyl is $C_{1-10}$.

The terms "alkylsulfonyl" and "arylsulfonyl" as used herein denotes a group of formula —S($=$O)$_2$R wherein R is alkyl or aryl respectively and alkyl and aryl are as defined herein.

The term "halogen" or "halo" as used herein means fluorine, chlorine, bromine, or iodine.

The term "phenylene" as used herein refers to a $C_6H_4=$radical derived from benzene by replacement of 2H atoms. Three isomers, ortho (o-), meta (m-) and para (p-) are possible.

The term "acyl" as used herein denotes a group of formula —C($=$O)R wherein R is hydrogen or lower alkyl as defined herein. The term or "alkylcarbonyl" as used herein denotes a group of formula C($=$O)R wherein R is alkyl as defined herein. The term "arylcarbonyl" as used herein means a group of formula C($=$O)R wherein R is an aryl group; the term "benzoyl" as used herein an "arylcarbonyl" group wherein R is phenyl.

Compounds of formula I exhibit tautomerism. Tautomeric compounds can exist as two or more interconvertable species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C($=$O)—CH— $\leftrightarrows$ —C(—OH)$=$CH—), amide/imidic acid (—C($=$O)—NH— $\leftrightarrows$ —C(—OH)$=$N—) and amidine (—C($=$NR)—NH— $\leftrightarrows$ —C(—NHR)$=$N—) tautomers. The latter two are particularly common in heteroaryl and heterocyclic rings and the present invention encompasses all tautomeric forms of the compounds.

It will be appreciated by the skilled artisan that the compounds of formulae Ia and Ib may contain one or more chiral centers and therefore exist in two or more stereoisomeric forms. The racemates of these isomers, the individual isomers and mixtures enriched in one enantiomer, as well as diastereomers when there are two chiral centers, and mixtures partially enriched with specific diastereomers are within the scope of the present invention. It will be further appreciated by the skilled artisan that substitution of the tropane ring can be in either endo- or exo-configuration, and the present invention covers both configurations. The present invention includes all the individual stereoisomers (e.g. enantiomers), racemic mixtures or partially resolved mixtures of the compounds of formulae Ia and Ib and, where appropriate, the individual tautomeric forms thereof.

The racemates can be used as such or can be resolved into their individual isomers. The resolution can afford stereochemically pure compounds or mixtures enriched in one or more isomers. Methods for separation of isomers are well known (cf. Allinger N. L. and Eliel E. L. in "Topics in Stereochemistry", Vol. 6, Wiley Interscience, 1971) and include physical methods such as chromatography using a chiral adsorbent. Individual isomers can be prepared in chiral form from chiral precursors. Alternatively individual isomers can be separated chemically from a mixture by forming diastereomeric salts with a chiral acid, such as the individual enantiomers of 10-camphorsulfonic acid, camphoric acid, .alpha.-bromocamphoric acid, tartaric acid, diacetyltartaric acid, malic acid, pyrrolidone-5-carboxylic acid, and the like, fractionally crystallizing the salts, and then freeing one or both of the resolved bases, optionally repeating the process, so as obtain either or both substantially free of the other; i.e., in a form having an optical purity of >95%. Alternatively the racemates can be covalently linked to a chiral compound (auxiliary) to produce diastereomers which can be separated by chromatography or by fractional crystallization after which time the chiral auxiliary is chemically removed to afford the pure enantiomers.

The compounds of formulae Ia or Ib contain at least two basic centers and suitable acid addition salts are formed from acids which form non-toxic salts. Examples of salts of inorganic acids include the chloride, bromide, iodide, sulfate, bisulphate, nitrate, phosphate, hydrogen phosphate. Examples of salts of organic acids include acetate, fumarate, pamoate, aspartate, besylate, carbonate, bicarbonate, camsylate, D and L-lactate, D and L-tartrate, esylate, mesylate, malonate, orotate, gluceptate, methylsulphate, stearate, glucuronate, 2-napsylate, tosylate, hibenzate, nicotinate, isethionate, malate, maleate, citrate, gluconate, succinate, saccharate, benzoate and pamoate salts. For a review on suitable salts see Berge et al, *J. Pharm. Sci.*, 66, 1-19, 1977.

The term "solvate" as used herein means a compound of the invention or a salt, thereof, that further includes a stoichiometric or non-stoichiometric amount of a solvent bound by non-covalent intermolecular forces. Preferred solvents are volatile, non-toxic, and/or acceptable for administration to humans in trace amounts.

The term "hydrate" as used herein means a compound of the invention or a salt thereof, that further includes a stoichiometric or non-stoichiometric amount of water bound by non-covalent intermolecular forces.

The term "wild type" as used herein refers to the HIV virus strain which possesses the dominant genotype which naturally occurs in the normal population which has not been exposed to reverse transcriptase inhibitors. The term "wild type reverse transcriptase" used herein has refers to the reverse transcriptase expressed by the wild type strain which has been sequenced and deposited in the SwissProt database with an accession number P03366.

The term "reduced susceptibility" as used herein refers to about a 10 fold, or greater, change in sensitivity of a particular viral isolate compared to the sensitivity exhibited by the wild type virus in the same experimental system The term "nucleoside and nucleotide reverse transcriptase inhibitors" ("NRTI's) as used herein means nucleosides and nucleotides and analogues thereof that inhibit the activity of HIV-1 reverse transcriptase, the enzyme which catalyzes the conversion of viral genomic HIV-1 RNA into proviral HIV-1 DNA.

The term "non-nucleoside reverse transcriptase inhibitors" ("NNRTI's) as used herein means non-nucleosides that inhibit the activity of HIV-1 reverse transcriptase.

The term "protease inhibitor" ("PI") as used herein means inhibitors of the HIV-1 protease, an enzyme required for the proteolytic cleavage of viral polyprotein precursors (e.g., viral GAG and GAG Pol polyproteins), into the individual functional proteins found in infectious HIV-1. HIV protease inhibitors include compounds having a peptidomimetic structure, high molecular weight (7600 daltons) and substantial peptide character, e.g. CRIXIVAN as well as nonpeptide protease inhibitors e.g., VIRACEPT.

The following abbreviations are used throughout this specification and claims: (atm) atmospheres, (BBN or 9-BBN) 9-borabicyclo[3.3.1]nonane, (Boc) tert-butoxycarbonyl, ((BOC)$_2$O) di-tert-butyl pyrocarbonate or boc anhydride, (Bn) benzyl, (Bu) butyl, (cbz or Z) benzyloxycarbonyl, (DABCO) diazabicyclooctane, (DAST) diethylaminosulfur trifluoride, (DBU) 1,8-diazabicyclo[5,4,0]undec-7-ene, (DCE) 1,2-dichloroethane, (DCM) dichloromethane, (DEAD) diethyl azodicarboxylate, (DLAD) di-iso-propylazodicarboxylate, (DEIPA) diethyl iso-propylamine, (DIBAL-H) di-iso-butylaluminumhydride, (DMA) N,N-dimethyl acetamide, (DMAP) 4-N,N-dimethylaminopyridine, (DMF) N,N-dimethylformamide, (dppf) 1,1'-bis-(diphenylphosphino)ferrocene, (EDCI) 1-(3-dimethylaminopropyl)-3-ethylcarbodiimide hydrochloride, (EtOAc) ethyl acetate, (Et$_2$O) diethyl ether, (Et) ethyl, (EtOH) ethanol, (LiHMDS) lithium hexamethyl disilazane, (HOAc) acetic acid, (HPLC) high pressure liquid chromatography, (i-Pr) iso-propyl, (Me) methyl, (MeCN) acetonitrile, (MeOH) methanol, (MTBE) methyl t-butyl ether, (mp) melting point, (ms) mass spectrum, (NBS) N-bromosuccinimide, (NMP) N-methylpyrrolidone, (PCC) pyridinium chlorochromate, (PDC) pyridinium dichromate, (Pr) propyl, (psi) pounds per square inch, (pyr) pyridine (rt or RT) room temperature, (TEA or Et$_3$N) triethylamine, (Tf) triflate CF$_3$SO$_2$—, (TFA) trifluoroacetic acid, (THF) tetrahydrofuran, (TLC) thin layer chromatography, (TMHD) 2,2,6,6-tetramethylheptane-2,6-dione, (TsOH) p-toluenesulfonic acid monohydrate,

EXAMPLES OF COMPOUNDS OF THE INVENTION

Examples of representative compounds encompassed by the present invention and within the scope of the invention are provided in the following Table. These examples and preparations which follow are provided to enable those skilled in the art to more clearly understand and to practice the present invention. They should not be considered as limiting the scope of the invention, but merely as being illustrative and representative thereof.

In general, the nomenclature used in this Application is based on AUTONOM™ v.4.0, a Beilstein Institute computerized system for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

| Cpd # | NAME | MS [M + H]$^+$ |
|---|---|---|
| I-1 | 4-Butyl-3-cyclohexylmethyl-8-[1-(2,6-dimethyl-benzoyl)-piperidin-4-yl]-1-oxa-3,8-diaza-spiro[4.5]decan-2-one | 524 |
| I-2 | 4-Butyl-8-[1-(2,6-dimethyl-benzoyl)-piperidin-4-yl]-1-oxa-3,8-diaza-spiro[4.5]decan-2-one | 428 |
| I-3 | 3-Benzyl-4-butyl-8-[1-(2,6-dimethyl-benzoyl)-piperidin-4-yl]-1-oxa-3,8-diaza-spiro[4.5]decan-2-one | 518 |
| I-4 | 4-Butyl-8-[1-(2,6-dimethyl-benzoyl)-piperidin-4-yl]-3-(tetrahydro-pyran-4-ylmethyl)-1-oxa-3,8-diaza-spiro[4.5]decan-2-one | 526 |
| I-5 | 4-Butyl-8-[1-(2,6-dimethyl-benzoyl)-piperidin-4-yl]-3-isobutyl-1-oxa-3,8-diaza-spiro[4.5]decan-2-one | 484 |
| I-6 | 4-Butyl-8-[1-(2,6-dimethyl-benzoyl)-piperidin-4-yl]-3-(tetrahydro-furan-3-ylmethyl)-1-oxa-3,8-diaza-spiro[4.5]decan-2-one; compound with hydrochloric acid | 512 |
| I-7 | 3-Cyclohexylmethyl-8-[1-(2,6-dimethyl-benzoyl)-piperidin-4-yl]-4-propyl-1-oxa-3,8-diaza-spiro[4.5]decan-2-one | 510 |
| I-8 | 3-Cyclohexylmethyl-8-[1-(2,6-dimethyl-benzoyl)-piperidin-4-yl]-4-isobutyl-1-oxa-3,8-diaza-spiro[4.5]decan-2-one | 524 |
| I-9 | 4-Cyclohexylmethyl-8-[1-(2,6-dimethyl-benzoyl)-piperidin-4-yl]-1-oxa-3,8-diaza-spiro[4.5]decan-2-one | 468 |

-continued

| Cpd # | NAME | MS [M + H]+ |
|---|---|---|
| I-10 | 3-Butyl-4-cyclohexylmethyl-8-[1-(2,6-dimethyl-benzoyl)-piperidin-4-yl]-1-oxa-3,8-diaza-spiro[4.5]decan-2-one | 524 |
| I-11 | 3-Cyclohexylmethyl-8-[1-(2,6-dimethyl-benzoyl)-piperidin-4-yl]-4-ethoxymethyl-1-oxa-3,8-diaza-spiro[4.5]decan-2-one | 526 |
| 1-12 | 3-Cyclohexylmethyl-8-[1-(2,6-dimethyl-benzoyl)-piperidin-4-yl]-4-(2-methoxy-ethyl)-1-oxa-3,8-diaza-spiro[4.5]decan-2-one | 526 |
| I-13 | 3-Cyclohexylmethyl-8-[1-(2,6-dimethyl-benzoyl)-piperidin-4-yl]-4-(2-methoxy-ethyl)-1-oxa-3,8-diaza-spiro[4.5]decan-2-one; compound with hydrochloric acid | 526 |
| I-14 | 4-But-(E)-ylidene-3-cyclohexylmethyl-8-[1-(2,6-dimethyl-benzoyl)-piperidin-4-yl]-1-oxa-3,8-diaza-spiro[4.5]decan-2-one | 522 |
| I-15 | 4-Butyl-3-cyclohexylmethyl-8-[8-(2,6-dimethyl-benzoyl)-8-aza-bicyclo[3.2.1]oct-3-yl]-1-oxa-3,8-diaza-spiro[4.5]decan-2-one | 550 |
| I-16 | 4-Butyl-cyclohexylmethyl-8-[8-(2,6-dimethyl-benzoyl)-8-aza-bicyclo[3.2.1]oct-3-yl]-1-oxa-3,8-diaza-spiro[4.5]decan-2-one | 550 |
| I-17 | 4-Butyl-3-cyclohexylmethyl-8-[1-(4,6-dimethyl-pyrimidine-5-carbonyl)-piperidin-4-yl]-1-oxa-3,8-diaza-spiro[4.5]decan-2-one | 526 |
| I-18 | 4-Butyl-3-cyclohexylmethyl-8-[1-(2,4-dimethyl-pyridine-3-carbonyl)-piperidin-4-yl]-1-oxa-3,8-diaza-spiro[4.5]decan-2-one | 525 |
| I-19 | 4-Butyl-3-cyclohexylmethyl-8-[1-(2-methyl-benzoyl)-piperidin-4-yl]-1-oxa-3,8-diaza-spiro[4.5]decan-2-one | 510 |
| I-20 | 4-Butyl-3-cyclohexylmethyl-8-[1-(1,3,5-trimethyl-1H-pyrazole-4-carbonyl)-piperidin-4-yl]-1-oxa-3,8-diaza-spiro[4.5]decan-2-one | 528 |
| I-21 | 4-Butyl-3-cyclohexylmethyl-8-[1-(4-methoxy-2,6-dimethyl-benzoyl)-piperidin-4-yl]-1-oxa-3,8-diaza-spiro[4.5]decan-2-one; compound with trifluoro-acetic acid | 554 |
| I-22 | 4-Butyl-3-cyclohexylmethyl-8-[1-(2,4-dimethyl-6-oxo-6H-pyran-3-carbonyl)-piperidin-4-yl]-1-oxa-3,8-diaza-spiro[4.5]decan-2-one; compound with trifluoro-acetic acid | 542 |
| I-23 | 4-Butyl-3-cyclohexylmethyl-8-[1-(3,5-dimethyl-isoxazole-4-carbonyl)-piperidin-4-yl]-1-oxa-3,8-diaza-spiro[4.5]decan-2-one | 515 |
| I-24 | 4-Butyl-3-cyclohexylmethyl-8-[1-(2,6-dimethoxy-benzoyl)-piperidin-4-yl]-1-oxa-3,8-diaza-spiro[4.5]decan-2-one; compound with trifluoro-acetic acid | 556 |
| I-25 | 4-Butyl-3-cyclohexylmethyl-8-[1-(3-fluoro-2-methyl-benzoyl)-piperidin-4-yl]-1-oxa-3,8-diaza-spiro[4.5]decan-2-one; compound with trifluoro-acetic acid | 528 |
| I-26 | 4-Butyl-3-cyclohexylmethyl-8-[1-(2,3-dimethyl-benzoyl)-piperidin-4-yl]-1-oxa-3,8-diaza-spiro[4.5]decan-2-one; compound with trifluoro-acetic acid | 524 |
| I-27 | 4-Butyl-3-cyclohexylmethyl-8-[1-(2,4-dimethyl-benzoyl)-piperidin-4-yl]-1-oxa-3,8-diaza-spiro[4.5]decan-2-one; compound with trifluoro-acetic acid | 524 |
| I-28 | 4-Butyl-3-cyclohexylmethyl-8-[1-(1-methyl-1H-pyrrole-2-carbonyl)-piperidin-4-yl]-1-oxa-3,8-diaza-spiro[4.5]decan-2-one; compound with trifluoro-acetic acid | 499 |
| I-29 | 4-Butyl-3-cyclohexylmethyl-8-[1-(1H-pyrrole-2-carbonyl)-piperidin-4-yl]-1-oxa-3,8-diaza-spiro[4.5]decan-2-one; compound with trifluoro-acetic acid | 485 |
| I-30 | 4-Butyl-3-cyclohexylmethyl-8-[1-(2-ethyl-5-methyl-2H-pyrazole-3-carbonyl)-piperidin-4-yl]-1-oxa-3,8-diaza-spiro[4.5]decan-2-one; compound with trifluoro-acetic acid | 528 |
| I-31 | 4-Butyl-3-cyclohexylmethyl-8-[1-(2-methylamino-benzoyl)-piperidin-4-yl]-1-oxa-3,8-diaza-spiro[4.5]decan-2-one; compound with trifluoro-acetic acid | 525 |
| I-32 | 4-Butyl-3-cyclohexylmethyl-8-[1-(2-dimethylamino-benzoyl)-piperidin-4-yl]-1-oxa-3,8-diaza-spiro[4.5]decan-2-one; compound with trifluoro-acetic acid | 539 |
| I-33 | 4-Butyl-3-cyclohexylmethyl-8-[1-(2,6-difluoro-benzoyl)-piperidin-4-yl]-1-oxa-3,8-diaza-spiro[4.5]decan-2-one; compound with trifluoro-acetic acid | 532 |
| I-34 | 8-[1-(1-Acetyl-piperidine-4-carbonyl)-piperidin-4-yl]-4-butyl-3-cyclohexylmethyl-1-oxa-3,8-diaza-spiro[4.5]decan-2-one; compound with trifluoro-acetic acid | 545 |
| I-35 | 8-(1-Benzoyl-piperidin-4-yl)-4-butyl-3-cyclohexylmethyl-1-oxa-3,8-diaza-spiro[4.5]decan-2-one; compound with trifluoro-acetic acid | 496 |
| I-36 | 4-[4-(4-Butyl-3-cyclohexylmethyl-2-oxo-1-oxa-3,8-diaza-spiro[4.5]dec-8-yl)-piperidine-1-carbonyl]-benzonitrile; compound with trifluoro-acetic acid | |
| I-37 | 4-Butyl-8-(1-cyclohexanecarbonyl-piperidin-4-yl)-3-cyclohexylmethyl-1-oxa-3,8-diaza-spiro[4.5]decan-2-one; compound with trifluoro-acetic acid | 521 |
| I-38 | 4-Butyl-3-cyclohexylmethyl-8-[1-(furan-2-carbonyl)-piperidin-4-yl]-1-oxa-3,8-diaza-spiro[4.5]decan-2-one; compound with trifluoro-acetic acid | 486 |
| I-39 | 4-Butyl-3-cyclohexylmethyl-8-[1-(furan-3-carbonyl)-piperidin-4-yl]-1-oxa-3,8-diaza-spiro[4.5]decan-2-one; compound with trifluoro-acetic acid | 486 |
| I-40 | 4-Butyl-3-cyclohexylmethyl-8-[1-(pyridine-4-carbonyl)-piperidin-4-yl]-1-oxa-3,8-diaza-spiro[4.5]decan-2-one; compound with trifluoro-acetic acid | 497 |
| I-41 | 3-[4-(4-Butyl-3-cyclohexylmethyl-2-oxo-1-oxa-3,8-diaza-spiro[4.5]dec-8-yl)-piperidine-1-carbonyl]-benzoic acid; compound with trifluoro-acetic acid | 540 |
| I-42 | 4-Butyl-3-cyclohexylmethyl-8-[1-(2-trifluoromethyl-benzoyl)-piperidin-4-yl]-1-oxa-3,8-diaza-spiro[4.5]decan-2-one; compound with trifluoro-acetic acid | 564 |
| I-43 | 4-Butyl-3-cyclohexylmethyl-8-[1-(5-methoxy-1H-indole-2-carbonyl)-piperidin-4-yl]-1-oxa-3,8-diaza-spiro[4.5]decan-2-one; compound with trifluoro-acetic acid | 565 |
| I-44 | 4-Butyl-3-cyclohexylmethyl-8-[1-(5-methyl-thiophene-2-carbonyl)-piperidin-4-yl]-1-oxa-3,8-diaza-spiro[4.5]decan-2-one; compound with trifluoro-acetic acid | 516 |

-continued

| Cpd # | NAME | MS [M + H]+ |
|---|---|---|
| I-45 | 4-Butyl-3-cyclohexylmethyl-8-[1-(thiophene-3-carbonyl)-piperidin-4-yl]-1-oxa-3,8-diaza-spiro[4.5]decan-2-one; compound with trifluoro-acetic acid | 502 |
| I-46 | 4-Butyl-3-cyclohexylmethyl-8-[1-(pyridine-2-carbonyl)-piperidin-4-yl]-1-oxa-3,8-diaza-spiro[4.5]decan-2-one; compound with trifluoro-acetic acid | 497 |
| I-47 | 4-Butyl-3-cyclohexylmethyl-8-[1-(2-methyl-pyridine-3-carbonyl)-piperidin-4-yl]-1-oxa-3,8-diaza-spiro[4.5]decan-2-one; compound with trifluoro-acetic acid | 511 |
| I-48 | 4-Butyl-3-cyclohexylmethyl-8-[1-(3-methyl-furan-2-carbonyl)-piperidin-4-yl]-1-oxa-3,8-diaza-spiro[4.5]decan-2-one; compound with trifluoro-acetic acid | 500 |
| I-49 | 4-Butyl-3-cyclohexylmethyl-8-[1-(pyridine-3-carbonyl)-piperidin-4-yl]-1-oxa-3,8-diaza-spiro[4.5]decan-2-one; compound with trifluoro-acetic acid | 497 |
| I-50 | 4-Butyl-3-cyclohexylmethyl-8-[1-(pyrazine-2-carbonyl)-piperidin-4-yl]-1-oxa-3,8-diaza-spiro[4.5]decan-2-one; compound with trifluoro-acetic acid | 498 |
| I-51 | 4-Butyl-8-[1-(2-chloro-benzoyl)-piperidin-4-yl]-3-cyclohexylmethyl-1-oxa-3,8-diaza-spiro[4.5]decan-2-one; compound with trifluoro-acetic acid | 530 |
| I-52 | 4-Butyl-3-cyclohexylmethyl-8-[1-(5-methyl-isoxazole-4-carbonyl)-piperidin-4-yl]-1-oxa-3,8-diaza-spiro[4.5]decan-2-one; compound with trifluoro-acetic acid | 501 |
| I-53 | 4-Butyl-3-cyclohexylmethyl-8-[1-(2-methyl-thiazole-4-carbonyl)-piperidin-4-yl]-1-oxa-3,8-diaza-spiro[4.5]decan-2-one; compound with trifluoro-acetic acid | 517 |
| I-54 | 4-Butyl-3-cyclohexylmethyl-8-[1-(1-methyl-1H-pyrazole-3-carbonyl)-piperidin-4-yl]-1-oxa-3,8-diaza-spiro[4.5]decan-2-one; compound with trifluoro-acetic acid | 500 |
| I-55 | 4-Butyl-3-cyclohexylmethyl-8-[1-(1-methyl-1H-imidazole-2-carbonyl)-piperidin-4-yl]-1-oxa-3,8-diaza-spiro[4.5]decan-2-one; compound with trifluoro-acetic acid | 500 |
| I-56 | 4-Butyl-3-cyclohexylmethyl-8-[1-(tetrahydro-furan-2-carbonyl)-piperidin-4-yl]-1-oxa-3,8-diaza-spiro[4.5]decan-2-one; compound with trifluoro-acetic acid | 490 |
| I-57 | 4-Butyl-3-cyclohexylmethyl-8-[1-(4-methoxy-thiophene-3-carbonyl)-piperidin-4-yl]-1-oxa-3,8-diaza-spiro[4.5]decan-2-one; compound with trifluoro-acetic acid | 532 |
| I-58 | 4-Butyl-3-cyclohexylmethyl-8-[1-(3-methyl-pyridine-2-carbonyl)-piperidin-4-yl]-1-oxa-3,8-diaza-spiro[4.5]decan-2-one; compound with trifluoro-acetic acid | 511 |
| I-59 | 4-Butyl-3-cyclohexylmethyl-8-[1-(1H-pyrazole-4-carbonyl)-piperidin-4-yl]-1-oxa-3,8-diaza-spiro[4.5]decan-2-one; compound with trifluoro-acetic acid | 486 |
| I-60 | 4-Butyl-3-cyclohexylmethyl-8-{1-[2-(1-methyl-1H-imidazol-4-yl)-acetyl]-piperidin-4-yl}-1-oxa-3,8-diaza-spiro[4.5]decan-2-one; compound with trifluoro-acetic acid | 514 |
| I-61 | 4-Butyl-3-cyclohexylmethyl-8-(1-phenylacetyl-piperidin-4-yl)-1-oxa-3,8-diaza-spiro[4.5]decan-2-one; compound with trifluoro-acetic acid | 510 |
| I-62 | 4-Butyl-3-cyclohexylmethyl-8-[1-(2-imidazol-1-yl-acetyl)-piperidin-4-yl]-1-oxa-3,8-diaza-spiro[4.5]decan-2-one; compound with trifluoro-acetic acid | 500 |
| I-63 | 4-Butyl-3-cyclohexylmethyl-8-[1-(3-morpholin-4-yl-propionyl)-piperidin-4-yl]-1-oxa-3,8-diaza-spiro[4.5]decan-2-one; compound with trifluoro-acetic acid | 533 |
| I-64 | 4-Butyl-3-cyclohexylmethyl-8-{1-[3-(4-methyl-piperazin-1-yl)-propionyl]-piperidin-4-yl}-1-oxa-3,8-diaza-spiro[4.5]decan-2-one; compound with trifluoro-acetic acid | 546 |
| I-65 | 4-Butyl-3-cyclohexylmethyl-8-[1-(2-1H-tetrazol-5-yl-acetyl)-piperidin-4-yl]-1-oxa-3,8-diaza-spiro[4.5]decan-2-one; compound with trifluoro-acetic acid | 502 |
| I-66 | 4-Butyl-3-cyclohexylmethyl-8-[1-(3-pyridin-3-yl-propionyl)-piperidin-4-yl]-1-oxa-3,8-diaza-spiro[4.5]decan-2-one; compound with trifluoro-acetic acid | 525 |
| I-67 | 4-(4-Butyl-3-cyclohexylmethyl-2-oxo-1-oxa-3,8-diaza-spiro[4.5]dec-8-yl)-piperidine-1-carboxylic acid benzyl ester | 526 |
| I-68 | 4-Butyl-3-cyclohexylmethyl-8-[1-(3,5-dimethyl-isoxazole-4-sulfonyl)-piperidin-4-yl]-1-oxa-3,8-diaza-spiro[4.5]decan-2-one; compound with trifluoro-acetic acid | 551 |
| I-69 | 4-Butyl-8-[1-(5-chloro-1,3-dimethyl-1H-pyrazole-4-sulfonyl)-piperidin-4-yl]-3-cyclohexylmethyl-1-oxa-3,8-diaza-spiro[4.5]decan-2-one; compound with trifluoro-acetic acid | 584 |
| I-70 | 4-[4-(4-Butyl-3-cyclohexylmethyl-2-oxo-1-oxa-3,8-diaza-spiro[4.5]dec-8-yl)-piperidine-1-sulfonyl]-2,5-dimethyl-furan-3-carboxylic acid methyl ester; compound with trifluoro-acetic acid | 608 |
| I-71 | 8-(1-Benzenesulfonyl-piperidin-4-yl)-4-butyl-cyclohexylmethyl-1-oxa-3,8-diaza-spiro[4.5]decan-2-one; compound with trifluoro-acetic acid | 532 |
| I-72 | 4-Butyl-3-cyclohexylmethyl-8-[1-(thiophene-2-sulfonyl)-piperidin-4-yl]-1-oxa-3,8-diaza-spiro[4.5]decan-2-one; compound with trifluoro-acetic acid | 538 |
| I-73 | 4-Butyl-3-cyclohexylmethyl-8-[1-(2,4,6-trimethyl-benzenesulfonyl)-piperidin-4-yl]-1-oxa-3,8-diaza-spiro[4.5]decan-2-one | 574 |
| I-74 | 4-(4-Butyl-3-cyclohexylmethyl-2-oxo-1-oxa-3,8-diaza-spiro[4.5]dec-8-yl)-piperidine-1-carboxylic acid (2,6-dimethyl-phenyl)-amide; compound with trifluoro-acetic acid | 539 |
| I-75 | 1-Butyl-3-cyclohexylmethyl-9-[1-(2,6-dimethyl-benzoyl)-piperidin-4-yl]-1,4,9-triaza-spiro[5.5]undecane-2,5-dione | 662 |
| I-76 | 1-Butyl-3-((S)-cyclohexyl-hydroxy-methyl)-9-[1-(2,6-dimethyl-benzoyl)-piperidin-4-yl]-1,4,9-triaza-spiro[5.5]undecane-2,5-dione (m.p. 246.9-248) | |
| I-77 | 5-Butyl-3-methyl-9-(1-{(E)-3-(3,4,5-trimethoxy-phenyl)-acryloyl}-piperidin-4-yl)-1-oxa-3,9-diaza-spiro[5.5]undecan-2-one; compound with trifluoro-acetic acid | 544 |

-continued

| Cpd # | NAME | MS [M + H]+ |
|---|---|---|
| I-78 | 4-(5-Butyl-3-methyl-2-oxo-1-oxa-3,9-diaza-spiro[5.5]undec-9-yl)-piperidine-1-carboxylic acid (2,6-dimethyl-phenyl)-amide; compound with trifluoro-acetic acid | 471 |
| I-79 | 8-[1-(2,6-Dimethyl-benzoyl)-piperidin-4-yl]-3-phenethyl-1-oxa-3,8-diaza-spiro[4.5]decan-2-one; compound with trifluoro-acetic acid | 476 |
| I-80 | 4-Butyl-3-cyclohexylmethyl-8-[1-(2,6-dimethyl-benzoyl)-4-methyl-piperidin-4-yl]-1-oxa-3,8-diaza-spiro[4.5]decan-2-one; compound with hydrochloric acid | 538 |
| I-81 | 4-Butyl-8-[1-(2,6-dimethyl-benzoyl)-piperidin-4-yl]-3-(2-methoxy-ethyl)-1-oxa-3,8-diaza-spiro[4.5]decan-2-one; compound with trifluoroacetic acid | 486 |
| I-82 | 4-Butyl-8-[1-(2,6-dimethyl-benzoyl)-piperidin-4-yl]-3-ethyl-1-oxa-3,8-diaza-spiro[4.5]decan-2-one; compound with methane | 456.7 |
| I-83 | 4-Butyl-8-[1-(2,6-dimethyl-benzoyl)-piperidin-4-yl]-3-phenethyl-1-oxa-3,8-diaza-spiro[4.5]decan-2-one; compound with trifluoro-acetic acid | 532.6 |
| I-84 | 4-Butyl-8-[1-(2,6-dimethyl-benzoyl)-piperidin-4-yl]-3-(2-fluoro-ethyl)-1-oxa-3,8-diaza-spiro[4.5]decan-2-one; compound with trifluoro-acetic acid | 474.7 |
| I-85 | 4-Butyl-8-[1-(2,6-dimethyl-benzoyl)-piperidin-4-yl]-3-hexyl-1-oxa-3,8-diaza-spiro[4.5]decan-2-one; compound with trifluoro-acetic acid | 512.8 |
| I-86 | 4-Butyl-8-[1-(2,6-dimethyl-benzoyl)-piperidin-4-yl]-3-((S)-2-methyl-butyl)-1-oxa-3,8-diaza-spiro[4.5]decan-2-one; compound with trifluoro-acetic acid | 498.8 |
| I-87 | 4-Butyl-8-[1-(2,6-dimethyl-benzoyl)-piperidin-4-yl]-3-(3-methyl-butyl)-1-oxa-3,8-diaza-spiro[4.5]decan-2-one; compound with trifluoro-acetic acid | 498.8 |
| I-88 | 4-Butyl-3-cyclopropylmethyl-8-[1-(2,6-dimethyl-benzoyl)-piperidin-4-yl]-1-oxa-3,8-diaza-spiro[4.5]decan-2-one; compound with trifluoro-acetic acid | 482.2 |
| I-89 | 4-Butyl-8-[1-(2,6-dimethyl-benzoyl)-piperidin-4-yl]-3-(5-methyl-hexyl)-1-oxa-3,8-diaza-spiro[4.5]decan-2-one; compound with trifluoro-acetic acid | 526.8 |
| I-90 | 4-Butyl-8-[1-(2,6-dimethyl-benzoyl)-piperidin-4-yl]-3-(2-methyl-butyl)-1-oxa-3,8-diaza-spiro[4.5]decan-2-one; compound with trifluoro-acetic acid | 512.8 |
| I-91 | 4-Butyl-8-[1-(2,6-dimethyl-benzoyl)-piperidin-4-yl]-3-pentyl-1-oxa-3,8-diaza-spiro[4.5]decan-2-one; compound with trifluoro-acetic acid | 498.8 |
| I-92 | 4-Butyl-8-[1-(2,6-dimethyl-benzoyl)-piperidin-4-yl]-3-(2-methyl-benzyl)-1-oxa-3,8-diaza-spiro[4.5]decan-2-one; compound with trifluoro-acetic acid | 532.8 |
| I-93 | 4-Butyl-3-(2-cyclohexyl-ethyl)-8-[1-(2,6-dimethyl-benzoyl)-piperidin-4-yl]-1-oxa-3,8-diaza-spiro[4.5]decan-2-one; compound with trifluoro-acetic acid | 538.9 |
| I-94 | 4-Butyl-8-[1-(2,6-dimethyl-benzoyl)-piperidin-4-yl]-3-(2-fluoro-benzyl)-1-oxa-3,8-diaza-spiro[4.5]decan-2-one; compound with trifluoro-acetic acid | 536.8 |
| I-95 | 4-Butyl-8-[1-(2,6-dimethyl-benzoyl)-piperidin-4-yl]-3-(1-phenyl-ethyl)-1-oxa-3,8-diaza-spiro[4.5]decan-2-one; compound with trifluoro-acetic acid | 532.8 |
| I-96 | 4-Butyl-3-cyclobutylmethyl-8-[1-(2,6-dimethyl-benzoyl)-piperidin-4-yl]-1-oxa-3,8-diaza-spiro[4.5]decan-2-one; compound with trifluoro-acetic acid | 496.8 |
| I-97 | 4-Butyl-8-[1-(2,6-dimethyl-benzoyl)-piperidin-4-yl]-3-(2-hydroxy-ethyl)-1-oxa-3,8-diaza-spiro[4.5]decan-2-one; compound with trifluoro-acetic acid | 472.8 |
| I-98 | 4-Butyl-8-[1-(2,6-dimethyl-benzoyl)-piperidin-4-yl]-3-(2-hydroxy-ethyl)-1-oxa-3,8-diaza-spiro[4.5]decan-2-one; compound with trifluoro-acetic acid | 500.9 |
| I-99 | 8-[1-(2,6-Dimethyl-benzoyl)-piperidin-4-yl]-4-methyl-3-(tetrahydro-furan-2-ylmethyl)-1-oxa-3,8-diaza-spiro[4.5]decan-2-one; compound with trifluoro-acetic acid | 512 |
| I-100 | 4-Butyl-8-[1-(2,6-dimethyl-benzoyl)-piperidin-4-yl]-3-(2-hydroxy-ethyl)-1-oxa-3,8-diaza-spiro[4.5]decan-2-one; compound with trifluoro-acetic acid | 472.8 |
| I-101 | 4-Butyl-8-[1-(2,6-dimethyl-benzoyl)-piperidin-4-yl]-3-(2-hydroxy-ethyl)-1-oxa-3,8-diaza-spiro[4.5]decan-2-one; compound with trifluoro-acetic acid | 500.9 |
| I-102 | 4-Butyl-8-[1-(2,6-dimethyl-benzoyl)-piperidin-4-yl]-3-(2-methoxy-ethyl)-1-oxa-3,8-diaza-spiro[4.5]decan-2-one; compound with trifluoro-acetic acid | |
| I-103 | 8-[1-(2,6-Dimethyl-benzoyl)-piperidin-4-yl]-4-methyl-3-(tetrahydro-furan-2-ylmethyl)-1-oxa-3,8-diaza-spiro[4.5]decan-2-one; compound with trifluoro-acetic acid | |
| I-104 | 4-Butyl-8-[1-(2,6-dimethyl-benzoyl)-piperidin-4-yl]-3-(4-fluoro-2-trifluoromethyl-benzyl)-1-oxa-3,8-diaza-spiro[4.5]decan-2-one; compound with trifluoro-acetic acid | 604.7 |
| I-105 | 4-Butyl-8-[1-(2,6-dimethyl-benzoyl)-piperidin-4-yl]-3-(2-trifluoromethyl-benzyl)-1-oxa-3,8-diaza-spiro[4.5]decan-2-one; compound with trifluoro-acetic acid | 586.7 |
| I-106 | 4-Butyl-3-(2,6-difluoro-benzyl)-8-[1-(2,6-dimethyl-benzoyl)-piperidin-4-yl]-1-oxa-3,8-diaza-spiro[4.5]decan-2-one; compound with trifluoro-acetic acid | 554.7 |
| I-107 | 4-Butyl-3-(2-diethylamino-ethyl)-8-[1-(2,6-dimethyl-benzoyl)-piperidin-4-yl]-1-oxa-3,8-diaza-spiro[4.5]decan-2-one; compound with trifluoro-acetic acid | 527.7 |
| I-108 | 4-Butyl-8-[1-(2,6-dimethyl-benzoyl)-piperidin-4-yl]-3-(2-methoxy-ethyl)-1-oxa-3,8-diaza-spiro[4.5]decan-2-one; compound with trifluoro-acetic acid | 486.7 |
| I-109 | 4-Butyl-8-[1-(2,6-dimethyl-benzoyl)-piperidin-4-yl]-3-propyl-1-oxa-3,8-diaza-spiro[4.5]decan-2-one; compound with trifluoro-acetic acid | 470.7 |
| I-110 | 3,4-Dibutyl-8-[1-(2,6-dimethyl-benzoyl)-piperidin-4-yl]-1-oxa-3,8-diaza-spiro[4.5]decan-2-one; compound with trifluoro-acetic acid | 484.7 |
| I-111 | 4-Butyl-8-[1-(2,6-dimethyl-benzoyl)-piperidin-4-yl]-3-pyridin-3-ylmethyl-1-oxa-3,8-diaza-spiro[4.5]decan-2-one; compound with trifluoro-acetic acid | 519.7 |
| I-112 | 2-{4-Butyl-8-[1-(2,6-dimethyl-benzoyl)-piperidin-4-yl]-2-oxo-1-oxa-3,8-diaza-spiro[4.5]dec-3-ylmethyl}-furan-3-carboxylic acid methyl ester; compound with trifluoro-acetic acid | 566.7 |

-continued

| Cpd # | NAME | MS [M + H]+ |
|---|---|---|
| I-113 | 2-{4-Butyl-8-[1-(2,6-dimethyl-benzoyl)-piperidin-4-yl]-2-oxo-1-oxa-3,8-diaza-spiro[4.5]dec-3-yl}-N,N-diethyl-acetamide; compound with trifluoro-acetic acid | 541.7 |
| I-114 | 4-Butyl-8-[1-(2,6-dimethyl-benzoyl)-piperidin-4-yl]-3-(2-methoxy-benzyl)-1-oxa-3,8-diaza-spiro[4.5]decan-2-one; compound with trifluoro-acetic acid | 548.7 |
| I-115 | 4-Butyl-8-[1-(2,6-dimethyl-benzoyl)-piperidin-4-yl]-3-pyridin-4-ylmethyl-1-oxa-3,8-diaza-spiro[4.5]decan-2-one; compound with trifluoro-acetic acid | 519.7 |
| I-116 | 4-Butyl-8-[1-(2,6-dimethyl-benzoyl)-piperidin-4-yl]-3-pyridin-2-ylmethyl-1-oxa-3,8-diaza-spiro[4.5]decan-2-one; compound with trifluoro-acetic acid | 519.7 |
| I-117 | 4-Butyl-3-(2-dimethylamino-ethyl)-8-[1-(2,6-dimethyl-benzoyl)-piperidin-4-yl]-1-oxa-3,8-diaza-spiro[4.5]decan-2-one; compound with trifluoro-acetic acid | 499.7 |
| I-118 | 4-Butyl-8-[1-(2,6-dimethyl-benzoyl)-piperidin-4-yl]-3-(2-morpholin-4-yl-ethyl)-1-oxa-3,8-diaza-spiro[4.5]decan-2-one; compound with trifluoro-acetic acid | 541.7 |
| I-119 | 4-Butyl-8-[1-(2,6-dimethyl-benzoyl)-piperidin-4-yl]-3-(2-piperidin-1-yl-ethyl)-1-oxa-3,8-diaza-spiro[4.5]decan-2-one; compound with trifluoro-acetic acid | 539.7 |
| I-120 | 4-Butyl-8-[1-(2,6-dimethyl-benzoyl)-piperidin-4-yl]-3-(2-pyrrolidin-1-yl-ethyl)-1-oxa-3,8-diaza-spiro[4.5]decan-2-one; compound with trifluoro-acetic acid | 525.9 |
| I-121 | 4-Butyl-8-[1-(2,6-dimethyl-benzoyl)-piperidin-4-yl]-3-[2-(1-methyl-pyrrolidin-2-yl)-ethyl]-1-oxa-3,8-diaza-spiro[4.5]decan-2-one; compound with trifluoro-acetic acid | 539.7 |
| I-122 | 2-{4-Butyl-8-[1-(2,6-dimethyl-benzoyl)-piperidin-4-yl]-2-oxo-1-oxa-3,8-diaza-spiro[4.5]dec-3-yl}-N,N-dimethyl-acetamide; compound with trifluoro-acetic acid | 513.7 |
| I-123 | 4-Butyl-8-[1-(2,6-dimethyl-benzoyl)-piperidin-4-yl]-3-(2-methyl-thiazol-4-ylmethyl)-1-oxa-3,8-diaza-spiro[4.5]decan-2-one; compound with trifluoro-acetic acid | 539.7 |
| I-124 | 3-(2-tert-Butoxy-ethyl)-4-butyl-8-[1-(2,6-dimethyl-benzoyl)-piperidin-4-yl]-1-oxa-3,8-diaza-spiro[4.5]decan-2-one; compound with trifluoro-acetic acid | 528.8 |
| I-125 | 4-Butyl-3-cyclopentylmethyl-8-[1-(2,6-dimethyl-benzoyl)-piperidin-4-yl]-1-oxa-3,8-diaza-spiro[4.5]decan-2-one; compound with trifluoro-acetic acid | 510.7 |
| I-126 | 4-Butyl-3-cyclohexylmethyl-8-[1-(2,6-dimethyl-4-morpholin-4-yl-benzoyl)-piperidin-4-yl]-1-oxa-3,8-diaza-spiro[4.5]decan-2-one; compound with trifluoro-acetic acid | 609.8 |
| I-127 | 4-Butyl-8-[1-(2,6-dimethyl-benzoyl)-piperidin-4-yl]-3-thiazol-4-ylmethyl-1-oxa-3,8-diaza-spiro[4.5]decan-2-one; compound with trifluoro-acetic acid | 525.8 |
| I-128 | 4-Butyl-8-[1-(2,6-dimethyl-benzoyl)-piperidin-4-yl]-3-(2-pyrrol-1-yl-ethyl)-1-oxa-3,8-diaza-spiro[4.5]decan-2-one; compound with trifluoro-acetic acid | 521.8 |
| I-129 | 4-Butyl-8-[1-(2,6-dimethyl-benzoyl)-piperidin-4-yl]-3-(4-methyl-pent-3-enyl)-1-oxa-3,8-diaza-spiro[4.5]decan-2-one; compound with trifluoro-acetic acid | 510.8 |
| I-130 | 4-Butyl-8-[1-(2,6-dimethyl-benzoyl)-piperidin-4-yl]-3-(1-methyl-butyl)-1-oxa-3,8-diaza-spiro[4.5]decan-2-one; compound with trifluoro-acetic acid | 498.8 |
| I-131 | 4-Butyl-8-[1-(2,6-dimethyl-benzoyl)-piperidin-4-yl]-3-(tetrahydro-pyran-2-ylmethyl)-1-oxa-3,8-diaza-spiro[4.5]decan-2-one; compound with trifluoro-acetic acid | 526.7 |
| I-132 | 4-Butyl-8-[1-(2,6-dimethyl-benzoyl)-piperidin-4-yl]-3-(2-ethoxy-ethyl)-1-oxa-3,8-diaza-spiro[4.5]decan-2-one; compound with trifluoro-acetic acid | 500.7 |
| I-133 | 4-Butyl-8-[1-(2,6-dimethyl-benzoyl)-piperidin-4-yl]-3-[2-(2-methoxy-ethoxy)-ethyl]-1-oxa-3,8-diaza-spiro[4.5]decan-2-one; compound with trifluoro-acetic acid | 530.7 |
| I-134 | 4-Butyl-8-[1-(2,6-dimethyl-benzoyl)-piperidin-4-yl]-3-(3,5-dimethyl-isoxazol-4-ylmethyl)-1-oxa-3,8-diaza-spiro[4.5]decan-2-one; compound with trifluoro-acetic acid | 537.7 |
| I-135 | 4-Butyl-8-[1-(2,6-dimethyl-benzoyl)-piperidin-4-yl]-3-(5-methyl-isoxazol-3-ylmethyl)-1-oxa-3,8-diaza-spiro[4.5]decan-2-one; compound with trifluoro-acetic acid | 523.7 |
| I-136 | 4-Butyl-8-[1-(2,6-dimethyl-benzoyl)-piperidin-4-yl]-3-(3-methyl-pyridin-2-ylmethyl)-1-oxa-3,8-diaza-spiro[4.5]decan-2-one; compound with trifluoro-acetic acid | 533.8 |
| I-137 | 4-Butyl-8-[1-(2,6-dimethyl-benzoyl)-piperidin-4-yl]-3-(4-fluoro-butyl)-1-oxa-3,8-diaza-spiro[4.5]decan-2-one; compound with trifluoro-acetic acid | 502.7 |
| I-138 | 4-Butyl-3-cyclohexylmethyl-8-[1-(4-fluoro-2,6-dimethyl-benzoyl)-piperidin-4-yl]-1-oxa-3,8-diaza-spiro[4.5]decan-2-one; compound with trifluoro-acetic acid | 542.8 |
| I-139 | 4-[4-(4-Butyl-3-cyclohexylmethyl-2-oxo-1-oxa-3,8-diaza-spiro[4.5]dec-8-yl)-piperidine-1-carbonyl]-3,5-dimethyl-benzamide; compound with trifluoro-acetic acid | 567.8 |
| I-140 | 4-Butyl-3-cyclohexylmethyl-8-[1-(2,6-dimethyl-4-pyridin-4-yl-benzoyl)-piperidin-4-yl]-1-oxa-3,8-diaza-spiro[4.5]decan-2-one; compound with trifluoro-acetic acid | 601.3 |
| I-141 | 4-[4-(5-Butyl-3-cyclohexylmethyl-2-oxo-1-oxa-3,9-diaza-spiro[5.5]undec-9-yl)-piperidine-1-carbonyl]-3,5-dimethyl-benzoic acid; compound with trifluoro-acetic acid | 582.4 |
| I-142 | 5-Butyl-3-cyclohexylmethyl-9-[1-(2,6-dimethyl-4-pyridin-4-yl-benzoyl)-piperidin-4-yl]-1-oxa-3,9-diaza-spiro[5.5]undecan-2-one; compound with trifluoro-acetic acid | 615.6 |

-continued

| Cpd # | NAME | MS [M + H]+ |
|---|---|---|
| I-143 | 4-[4-(5-Butyl-3-cyclohexylmethyl-2-oxo-1-oxa-3,9-diaza-spiro[5.5]undec-9-yl)-piperidine-1-carbonyl]-3,5-dimethyl-benzoic acid ethyl ester; compound with trifluoro-acetic acid | 610.6 |
| I-144 | 5-Butyl-3-cyclohexylmethyl-9-[1-(4-iodo-2,6-dimethyl-benzoyl)-piperidin-4-yl]-1-oxa-3,9-diaza-spiro[5.5]undecan-2-one; compound with trifluoro-acetic acid | 664.5 |
| I-145 | 5-Butyl-3-cyclohexylmethyl-9-[1-(2,6-dimethyl-4-thiophen-2-yl-benzoyl)-piperidin-4-yl]-1-oxa-3,9-diaza-spiro[5.5]undecan-2-one; compound with trifluoro-acetic acid | 620.7 |
| I-146 | 4-[4-(5-Butyl-3-cyclohexylmethyl-2-oxo-1-oxa-3,9-diaza-spiro[5.5]undec-9-yl)-piperidine-1-carbonyl]-3,5-dimethyl-benzonitrile; compound with trifluoro-acetic acid | 563.6 |
| I-147 | 5-Butyl-3-cyclohexylmethyl-9-[1-(2,6-dimethyl-4-pyridin-3-yl-benzoyl)-piperidin-4-yl]-1-oxa-3,9-diaza-spiro[5.5]undecan-2-one; compound with trifluoro-acetic acid | 615.6 |
| I-148 | 5-Butyl-3-cyclohexylmethyl-9-{1-[2,6-dimethyl-4-(4-methyl-thiazol-5-yl)-benzoyl]-piperidin-4-yl}-1-oxa-3,9-diaza-spiro[5.5]undecan-2-one; compound with trifluoro-acetic acid | 635.6 |
| I-149 | {4-[4-(4-Butyl-3-cyclohexylmethyl-2-oxo-1-oxa-3,8-diaza-spiro[4.5]dec-8-yl)-piperidine-1-carbonyl]-3,5-difluoro-phenyl}-carbamic acid tert-butyl ester | 647 |
| I-150 | 8-[1-(4-Amino-2,6-difluoro-benzoyl)-piperidin-4-yl]-4-butyl-3-cyclohexylmethyl-1-oxa-3,8-diaza-spiro[4.5]decan-2-one | 547 |
| I-151 | N-{4-[4-(4-Butyl-3-cyclohexylmethyl-2-oxo-1-oxa-3,8-diaza-spiro[4.5]dec-8-yl)-piperidine-1-carbonyl]-3,5-difluoro-phenyl}-acetamide | 589 |
| I-152 | 2-[4-(4-Butyl-3-cyclohexylmethyl-2-oxo-1-oxa-3,8-diaza-spiro[4.5]dec-8-yl)-piperidine-1-carbonyl]-3-methyl-benzonitrile | 535 |
| I-153 | 2-[4-(5-Butyl-3-cyclohexylmethyl-2-oxo-1-oxa-3,9-diaza-spiro[5.5]undec-9-yl)-piperidine-1-carbonyl]-3-methyl-benzonitrile | 549 |
| I-154 | 5-But-3-enyl-3-cyclohexylmethyl-9-[1-(2,6-dimethyl-benzoyl)-piperidin-4-yl]-1-oxa-3,9-diaza-spiro[5.5]undecan-2-one | 536 |
| I-155 | 5-Butyl-3-cyclohexylmethyl-9-[4-methyl-1-(2,4,5-trimethyl-thiophene-3-carbonyl)-piperidin-4-yl]-1-oxa-3,9-diaza-spiro[5.5]undecan-2-one | 572 |
| I-156 | 5-Butyl-3-cyclohexylmethyl-9-[4-methyl-1-(5-methyl-3-phenyl-isoxazole-4-carbonyl)-piperidin-4-yl]-1-oxa-3,9-diaza-spiro[5.5]undecan-2-one; compound with trifluoro-acetic acid | 605 |
| I-157 | 5-Butyl-9-{1-[4,6-dimethyl-2-(pyridin-2-yloxy)-pyrimidine-5-carbonyl]-piperidin-4-yl}-1-oxa-3,9-diaza-spiro[5.5]undecan-2-one; compound with trifluoro-acetic acid | 537 |
| I-158 | 4-Butyl-3-cyclohexylmethyl-8-[1-(3,5-dichloro-pyridine-4-carbonyl)-piperidin-4-yl]-1-oxa-3,8-diaza-spiro[4.5]decan-2-one | 565 |
| I-159 | (S)-4-Butyl-3-cyclohexylmethyl-8-[1-(2,6-dimethyl-benzoyl)-piperidin-4-yl]-1-oxa-3,8-diaza-spiro[4.5]decan-2-one | 524 |
| I-160 | (R)-4-Butyl-3-cyclohexylmethyl-8-[1-(2,6-dimethyl-benzoyl)-piperidin-4-yl]-1-oxa-3,8-diaza-spiro[4.5]decan-2-one | 524 |
| I-161 | 4-Butyl-3-cyclohexylmethyl-8-[1-(3,5-dichloro-pyridine-4-carbonyl)-piperidin-4-yl]-8-oxy-1-oxa-3,8-diaza-spiro[4.5]decan-2-one | 581 |
| I-162 | 4-Butyl-8-[1-(2,6-dimethyl-benzoyl)-piperidin-4-yl]-3-(1-hydroxy-cyclohexylmethyl)-1-oxa-3,8-diaza-spiro[4.5]decan-2-one | 540 |
| I-163 | 4-Butyl-3-cyclohexylmethyl-8-[1-(4-methoxy-2,6-dimethyl-benzoyl)-piperidin-4-yl]-8-oxy-1-oxa-3,8-diaza-spiro[4.5]decan-2-one | 570 |
| I-164 | 5-Butyl-9-[1-(2,6-dimethyl-benzoyl)-piperidin-4-yl]-3-(1-hydroxy-cyclohexylmethyl)-1-oxa-3,9-diaza-spiro[5.5]undecan-2-one | 554 |
| I-165 | 5-Butyl-3-cyclohexanecarbonyl-9-[1-(2,6-dimethyl-benzoyl)-piperidin-4-yl]-1-oxa-3,9-diaza-spiro[5.5]undecan-2-one | 552 |
| I-166 | 1-{5-Butyl-9-[1-(2,6-dimethyl-benzoyl)-piperidin-4-yl]-2-oxo-1-oxa-3,9-diaza-spiro[5.5]undec-3-ylmethyl}-cyclohexanecarbonitrile | 563 |
| I-167 | (E)-4-{3-Cyclohexylmethyl-9-[1-(2,6-dimethyl-benzoyl)-piperidin-4-yl]-2-oxo-1-oxa-3,9-diaza-spiro[5.5]undec-5-yl}-but-2-enoic acid methyl ester | 580 |
| I-168 | (E)-4-{3-Cyclohexylmethyl-9-[1-(2,6-dimethyl-benzoyl)-piperidin-4-yl]-2-oxo-1-oxa-3,9-diaza-spiro[5.5]undec-5-yl}-but-2-enenitrile | 547 |
| I-169 | 4-{3-Cyclohexylmethyl-9-[1-(2,6-dimethyl-benzoyl)-piperidin-4-yl]-2-oxo-1-oxa-3,9-diaza-spiro[5.5]undec-5-yl}-butyric acid methyl ester | 582 |
| I-170 | 4-{3-Cyclohexylmethyl-9-[1-(2,6-dimethyl-benzoyl)-piperidin-4-yl]-2-oxo-1-oxa-3,9-diaza-spiro[5.5]undec-5-yl}-butyronitrile | 549 |
| I-171 | 3-Cyclohexylmethyl-9-[1-(2,6-dimethyl-benzoyl)-piperidin-4-yl]-5-((E)-4-oxo-pent-2-enyl)-1-oxa-3,9-diaza-spiro[5.5]undecan-2-one | 564 |
| I-172 | (E)-4-(3-Cyclohexylmethyl-9-[1-(2,6-dimethyl-benzoyl)-piperidin-4-yl]-2-oxo-1-oxa-3,9-diaza-spiro[5.5]undec-5-yl}-but-2-enoic acid | 566 |
| I-173 | 3-Cyclohexylmethyl-9-[1-(2,6-dimethyl-benzoyl)-piperidin-4-yl]-5-((E)-4-hydroxy-pent-2-enyl)-1-oxa-3,9-diaza-spiro[5.5]undecan-2-one | 566 |
| I-174 | 3-Cyclohexylmethyl-9-[1-(2,6-dimethyl-benzoyl)-piperidin-4-yl]-5-(4-oxo-pentyl)-1-oxa-3,9-diaza-spiro[5.5]undecan-2-one | 566 |
| I-175 | 4-(3-Cyclohexylmethyl-9-[1-(2,6-dimethyl-benzoyl)-piperidin-4-yl]-2-oxo-1-oxa-3,9-diaza-spiro[5.5]undec-5-yl}-butyric acid | 568 |
| I-176 | 3-Cyclohexylmethyl-9-[1-(2,6-dimethyl-benzoyl)-piperidin-4-yl]-5-(4-hydroxy-pentyl)-1-oxa-3,9-diaza-spiro[5.5]undecan-2-one | 568 |

-continued

| Cpd # | NAME | MS [M + H]+ |
|---|---|---|
| I-177 | {3-Cyclohexylmethyl-9-[1-(2,6-dimethyl-benzoyl)-piperidin-4-yl]-2-oxo-1-oxa-3,9-diaza-spiro[5.5]undec-5-yl}-acetaldehyde oxime | 539 |
| I-178 | 3-Cyclohexylmethyl-9-[1-(2,6-dimethyl-benzoyl)-piperidin-4-yl]-5-((E)-pent-2-enyl)-1-oxa-3,9-diaza-spiro[5.5]undecan-2-one | 550 |
| I-179 | 3-Cyclohexylmethyl-9-[1-(2,6-dimethyl-benzoyl)-piperidin-4-yl]-5-pentyl-1-oxa-3,9-diaza-spiro[5.5]undecan-2-one | 552 |
| I-180 | 3-Cyclohexylmethyl-9-[1-(2,6-dimethyl-benzoyl)-piperidin-4-yl]-5-((E)-3-methanesulfonyl-allyl)-1-oxa-3,9-diaza-spiro[5.5]undecan-2-one | 600 |
| I-181 | 3-Cyclohexylmethyl-9-[1-(2,6-dimethyl-benzoyl)-piperidin-4-yl]-5-(2-methoxy-ethyl)-1-oxa-3,9-diaza-spiro[5.5]undecan-2-one | 540 |
| I-182 | 3-Cyclohexylmethyl-9-[1-(2,6-dimethyl-benzoyl)-piperidin-4-yl]-5-(3-methanesulfonyl-propyl)-1-oxa-3,9-diaza-spiro[5.5]undecan-2-one | 602 |
| I-183 | 5-Allyl-3-cyclohexylmethyl-9-[1-(2,6-dimethyl-benzoyl)-piperidin-4-yl]-1-oxa-3,9-diaza-spiro[5.5]undecan-2-one | 522 |
| I-184 | 3-Cyclohexylmethyl-9-[1-(2,6-dimethyl-benzoyl)-piperidin-4-yl]-5-propyl-1-oxa-3,9-diaza-spiro[5.5]undecan-2-one | 524 |
| I-185 | 3-Cyclohexylmethyl-9-[1-(2,6-dimethyl-benzoyl)-piperidin-4-yl]-5-(3,3,3-trifluoro-2-hydroxy-propyl)-1-oxa-3,9-diaza-spiro[5.5]undecan-2-one | 594 |
| I-186 | 3-Cyclohexylmethyl-9-[1-(2,6-dimethyl-benzoyl)-piperidin-4-yl]-5-(3,3,3-trifluoro-2-hydroxy-propyl)-1-oxa-3,9-diaza-spiro[5.5]undecan-2-one | 594 |
| I-187 | 3-Cyclohexylmethyl-5-(2-cyclopropyl-ethyl)-9-[1-(2,6-dimethyl-benzoyl)-piperidin-4-yl]-1-oxa-3,9-diaza-spiro[5.5]undecan-2-one | 550 |
| I-188 | 7-[4-(5-Butyl-3-cyclohexylmethyl-2-oxo-1-oxa-3,9-diaza-spiro[5.5]undec-9-yl)-piperidine-1-carbonyl]-2,3-dihydro-indole-1-carboxylic acid tert-butyl ester | 651 |
| I-189 | 5-Butyl-3-cyclohexylmethyl-9-[1-(2,3-dihydro-1H-indole-7-carbonyl)-piperidin-4-yl]-1-oxa-3,9-diaza-spiro[5.5]undecan-2-one | 551 |
| I-190 | (R)-5-Butyl-3-cyclohexylmethyl-9-[1-(2,6-dimethyl-benzoyl)-piperidin-4-yl]-1-oxa-3,9-diaza-spiro[5.5]undecan-2-one | 538 |
| I-191 | (S)-5-Butyl-3-cyclohexylmethyl-9-[1-(2,6-dimethyl-benzoyl)-piperidin-4-yl]-1-oxa-3,9-diaza-spiro[5.5]undecan-2-one | 538 |
| I-192 | 4-Butyl-3-methyl-8-[1-(2,4,6-trimethyl-benzoyl)-piperidin-4-yl]-1-oxa-3,8-diaza-spiro[4.5]decan-2-one; compound with trifluoro-acetic acid | 456.8 |
| I-193 | 4-Butyl-8-[1-(2,6-dichloro-benzoyl)-piperidin-4-yl]-3-methyl-1-oxa-3,8-diaza-spiro[4.5]decan-2-one; compound with trifluoro-acetic acid | 482.7 |
| I-194 | 4-Butyl-8-[1-(2-chloro-6-methyl-benzoyl)-piperidin-4-yl]-3-methyl-1-oxa-3,8-diaza-spiro[4.5]decan-2-one; compound with trifluoro-acetic acid | 462.7 |
| I-195 | 4-Butyl-8-[1-(2,6-dichloro-4-methyl-benzoyl)-piperidin-4-yl]-3-methyl-1-oxa-3,8-diaza-spiro[4.5]decan-2-one; compound with trifluoro-acetic acid | 469.7 |
| I-196 | 4-Butyl-8-[1-(4-methoxy-2,6-dimethyl-benzoyl)-piperidin-4-yl]-3-methyl-1-oxa-3,8-diaza-spiro[4.5]decan-2-one; compound with trifluoro-acetic acid | 472.8 |
| I-197 | 8-[1-(4-Butoxy-2,6-dimethyl-benzoyl)-piperidin-4-yl]-4-butyl-3-methyl-1-oxa-3,8-diaza-spiro[4.5]decan-2-one; compound with trifluoro-acetic acid | 514.8 |
| I-198 | 4-Butyl-8-[1-(4-ethoxy-2,6-dimethyl-benzoyl)-piperidin-4-yl]-3-methyl-1-oxa-3,8-diaza-spiro[4.5]decan-2-one; compound with trifluoro-acetic acid | 486.8 |
| I-199 | 4-Butyl-8-[1-(2-chloro-6-fluoro-benzoyl)-piperidin-4-yl]-3-methyl-1-oxa-3,8-diaza-spiro[4.5]decan-2-one; compound with trifluoro-acetic acid | 466.7 |
| I-200 | 8-[1-(2-Bromo-6-methyl-benzoyl)-piperidin-4-yl]-4-butyl-3-methyl-1-oxa-3,8-diaza-spiro[4.5]decan-2-one; compound with trifluoro-acetic acid | 508.7 |
| I-201 | 4-Butyl-8-[1-(2,6-difluoro-4-methoxy-benzoyl)-piperidin-4-yl]-3-methyl-1-oxa-3,8-diaza-spiro[4.5]decan-2-one; compound with trifluoro-acetic acid | 480.7 |
| I-202 | 4-Butyl-3-methyl-8-[1-(2,4,6-trimethoxy-benzoyl)-piperidin-4-yl]-1-oxa-3,8-diaza-spiro[4.5]decan-2-one; compound with trifluoro-acetic acid | 504.8 |
| I-203 | 4-Butyl-8-[1-(2,3-dimethyl-benzoyl)-piperidin-4-yl]-3-methyl-1-oxa-3,8-diaza-spiro[4.5]decan-2-one; compound with trifluoro-acetic acid | 442.8 |
| I-204 | 4-Butyl-8-[1-(2,4-dimethyl-benzoyl)-piperidin-4-yl]-3-methyl-1-oxa-3,8-diaza-spiro[4.5]decan-2-one; compound with trifluoro-acetic acid | 442.8 |
| I-205 | 4-Butyl-8-[1-(2-dimethylamino-benzoyl)-piperidin-4-yl]-3-methyl-1-oxa-3,8-diaza-spiro[4.5]decan-2-one; compound with trifluoro-acetic acid | 45738 |
| I-206 | 4-Butyl-3-methyl-8-[1-(1H-pyrrole-2-carbonyl)-piperidin-4-yl]-1-oxa-3,8-diaza-spiro[4.5]decan-2-one; compound with trifluoro-acetic acid | 403.7 |
| I-207 | 4-Butyl-8-[1-(3,5-dimethyl-isoxazole-4-carbonyl)-piperidin-4-yl]-3-methyl-1-oxa-3,8-diaza-spiro[4.5]decan-2-one; compound with trifluoro-acetic acid | 433.8 |
| I-208 | 4-Butyl-8-[1-(4,6-dimethyl-pyrimidine-5-carbonyl)-piperidin-4-yl]-3-methyl-1-oxa-3,8-diaza-spiro[4.5]decan-2-one; compound with trifluoro-acetic acid | 444.8 |
| I-209 | 8-[1-(4-Butoxy-2,6-dimethyl-benzoyl)-piperidin-4-yl]-4-butyl-3-cyclohexylmethyl-1-oxa-3,8-diaza-spiro[4.5]decan-2-one; compound with trifluoro-acetic acid | 596.9 |
| I-210 | 4-Butyl-3-cyclohexylmethyl-8-[1-(4-hydroxy-2,6-dimethyl-benzoyl)-piperidin-4-yl]-1-oxa-3,8-diaza-spiro[4.5]decan-2-one; compound with compound with hydrochloric acid | 540 |
| I-211 | 4-Butyl-3-cyclohexylmethyl-8-[1-(4-ethoxy-2,6-dimethyl-benzoyl)-piperidin-4-yl]-1-oxa-3,8-diaza-spiro[4.5]decan-2-one; compound with compound with hydrochloric acid | 568 |
| I-212 | 4-Butyl-3-cyclohexylmethyl-8-[1-(4,6-dimethyl-pyrimidine-5-carbonyl)-4-methyl-piperidin-4-yl]-1-oxa-3,8-diaza-spiro[4.5]decan-2-one; compound with trifluoro-acetic acid | 540.8 |

-continued

| Cpd # | NAME | MS [M + H]+ |
|---|---|---|
| I-213 | 4-Butyl-3-cyclohexylmethyl-8-[1-(2,4-dimethyl-pyridine-3-carbonyl)-4-methyl-piperidin-4-yl]-1-oxa-3,8-diaza-spiro[4.5]decan-2-one; compound with trifluoro-acetic acid | 539.8 |
| I-214 | 8-[1-(1-Benzyl-3,5-dimethyl-1H-pyrazole-4-carbonyl)-4-methyl-piperidin-4-yl]-4-butyl-3-cyclohexylmethyl-1-oxa-3,8-diaza-spiro[4.5]decan-2-one; compound with trifluoro-acetic acid | 618.9 |
| I-215 | 4-Butyl-3-cyclohexylmethyl-8-[1-(3,5-dimethyl-1-phenyl-1H-pyrazole-4-carbonyl)-4-methyl-piperidin-4-yl]-1-oxa-3,8-diaza-spiro[4.5]decan-2-one; compound with trifluoro-acetic acid | 604.8 |
| I-216 | 4-Butyl-3-cyclohexylmethyl-8-[1-(2,6-dichloro-benzoyl)-4-methyl-piperidin-4-yl]-1-oxa-3,8-diaza-spiro[4.5]decan-2-one; compound with trifluoro-acetic acid | 578.7 |
| I-217 | 8-[1-(4-Benzyloxy-2,6-dimethyl-benzoyl)-piperidin-4-yl]-4-butyl-3-cyclohexylmethyl-1-oxa-3,8-diaza-spiro[4.5]decan-2-one; compound with hydrochloric acid | 630.9 |
| I-218 | 4-Butyl-3-cyclohexylmethyl-8-[1-(5-methyl-3-phenyl-isoxazole-4-carbonyl)-piperidin-4-yl]-1-oxa-3,8-diaza-spiro[4.5]decan-2-one; compound with trifluoro-acetic acid | 577.7 |
| I-219 | 4-Butyl-3-cyclohexylmethyl-8-[1-(3-methyl-thiophene-2-carbonyl)-piperidin-4-yl]-1-oxa-3,8-diaza-spiro[4.5]decan-2-one; compound with trifluoro-acetic acid | 516.6 |
| I-220 | 4-Butyl-3-cyclohexylmethyl-8-[1-(2-methyl-2H-pyrazole-3-carbonyl)-piperidin-4-yl]-1-oxa-3,8-diaza-spiro[4.5]decan-2-one; compound with trifluoro-acetic acid | 500.7 |
| I-221 | 4-Butyl-3-cyclohexylmethyl-8-[1-(2-methyl-5-propyl-2H-pyrazole-3-carbonyl)-piperidin-4-yl]-1-oxa-3,8-diaza-spiro[4.5]decan-2-one; compound with trifluoro-acetic acid | 542.7 |
| I-222 | 4-Butyl-3-cyclohexylmethyl-8-[1-(4-methyl-2-phenyl-thiazole-5-carbonyl)-piperidin-4-yl]-1-oxa-3,8-diaza-spiro[4.5]decan-2-one; compound with trifluoro-acetic acid | 593.9 |
| I-223 | 4-Butyl-3-cyclohexylmethyl-8-[1-(4-methyl-2-pyridin-3-yl-thiazole-5-carbonyl)-piperidin-4-yl]-1-oxa-3,8-diaza-spiro[4.5]decan-2-one; compound with trifluoro-acetic acid | 594.7 |
| I-224 | 4-Butyl-3-cyclohexylmethyl-8-[1-(3,5-dimethyl-1H-pyrrole-2-carbonyl)-piperidin-4-yl]-1-oxa-3,8-diaza-spiro[4.5]decan-2-one; compound with trifluoro-acetic acid | 513.7 |
| I-225 | 4-Butyl-3-cyclohexylmethyl-8-[1-(5-ethyl-2-methyl-2H-pyrazole-3-carbonyl)-piperidin-4-yl]-1-oxa-3,8-diaza-spiro[4.5]decan-2-one; compound with trifluoro-acetic acid | 528.7 |
| I-226 | 4-Butyl-3-cyclohexylmethyl-8-[1-(4-methyl-thiazole-5-carbonyl)-piperidin-4-yl]-1-oxa-3,8-diaza-spiro[4.5]decan-2-one; compound with trifluoro-acetic acid | 517.7 |
| I-227 | 4-Butyl-3-cyclohexylmethyl-8-[1-(2,4-dimethyl-thiazole-5-carbonyl)-piperidin-4-yl]-1-oxa-3,8-diaza-spiro[4.5]decan-2-one; compound with trifluoro-acetic acid | 531.7 |
| I-228 | 5-[4-(4-Butyl-3-cyclohexylmethyl-2-oxo-1-oxa-3,8-diaza-spiro[4.5]dec-8-yl)-piperidine-1-carbonyl]-1-methyl-1H-pyrrole-2-sulfonic acid amide; compound with trifluoro-acetic acid | 578.7 |
| I-229 | 4-Butyl-3-cyclohexylmethyl-8-{1-[4-(2-methoxy-ethoxy)-2,6-dimethyl-benzoyl]-piperidin-4-yl}-1-oxa-3,8-diaza-spiro[4.5]decan-2-one; compound with trifluoro-acetic acid | 598.8 |
| I-230 | 5-Butyl-3-cyclohexylmethyl-9-[1-(2,6-dichloro-benzoyl)-piperidin-4-yl]-1-oxa-3,9-diaza-spiro[5.5]undecan-2-one; compound with trifluoro-acetic acid | 578.6 |
| I-231 | 5-Butyl-9-[1-(2-chloro-6-methyl-benzoyl)-piperidin-4-yl]-3-cyclohexylmethyl-1-oxa-3,9-diaza-spiro[5.5]undecan-2-one; compound with trifluoro-acetic acid | 558.7 |
| I-232 | 5-Butyl-3-cyclohexylmethyl-9-[1-(2,6-dichloro-4-methyl-benzoyl)-piperidin-4-yl]-1-oxa-3,9-diaza-spiro[5.5]undecan-2-one; compound with trifluoro-acetic acid | 592.7 |
| I-233 | 5-Butyl-3-cyclohexylmethyl-9-[1-(4-methoxy-2,6-dimethyl-benzoyl)-piperidin-4-yl]-1-oxa-3,9-diaza-spiro[5.5]undecan-2-one; compound with trifluoro-acetic acid | 568.8 |
| I-234 | 9-[1-(4-Butoxy-2,6-dimethyl-benzoyl)-piperidin-4-yl]-5-butyl-3-cyclohexylmethyl-1-oxa-3,9-diaza-spiro[5.5]undecan-2-one; compound with trifluoro-acetic acid | 610.8 |
| I-235 | 5-Butyl-3-cyclohexylmethyl-9-[1-(4-ethoxy-2,6-dimethyl-benzoyl)-piperidin-4-yl]-1-oxa-3,9-diaza-spiro[5.5]undecan-2-one; compound with trifluoro-acetic acid | 582.8 |
| I-236 | 5-Butyl-9-[1-(2-chloro-6-fluoro-benzoyl)-piperidin-4-yl]-3-cyclohexylmethyl-1-oxa-3,9-diaza-spiro[5.5]undecan-2-one; compound with trifluoro-acetic acid | 562.7 |
| I-237 | 5-Butyl-3-cyclohexylmethyl-9-[1-(2,4,6-trimethyl-benzoyl)-piperidin-4-yl]-1-oxa-3,9-diaza-spiro[5.5]undecan-2-one; compound with trifluoro-acetic acid | 552.8 |
| I-238 | 9-[1-(2-Bromo-6-methyl-benzoyl)-piperidin-4-yl]-5-butyl-3-cyclohexylmethyl-1-oxa-3,9-diaza-spiro[5.5]undecan-2-one; compound with trifluoro-acetic acid | 602.7 |
| I-239 | 5-Butyl-3-cyclohexylmethyl-9-[1-(2,6-difluoro-4-methoxy-benzoyl)-piperidin-4-yl]-1-oxa-3,9-diaza-spiro[5.5]undecan-2-one; compound with trifluoro-acetic acid | 576.8 |
| I-240 | 4-[4-(5-Butyl-3-cyclohexylmethyl-2-oxo-1-oxa-3,9-diaza-spiro[5.5]undec-9-yl)-piperidine-1-carbonyl]-3,5-dimethyl-benzamide; compound with trifluoro-acetic acid | 583.8 |

-continued

| Cpd # | NAME | MS [M + H]+ |
|---|---|---|
| I-241 | 5-Butyl-9-[1-(4-chloro-2-methoxy-benzoyl)-piperidin-4-yl]-3-cyclohexylmethyl-1-oxa-3,9-diaza-spiro[5.5]undecan-2-one; compound with trifluoro-acetic acid | 574.8 |
| I-242 | 5-Butyl-3-cyclohexylmethyl-9-[1-(2,3-dimethyl-benzoyl)-piperidin-4-yl]-1-oxa-3,9-diaza-spiro[5.5]undecan-2-one; compound with trifluoro-acetic acid | 538.8 |
| I-243 | 5-Butyl-3-cyclohexylmethyl-9-[1-(2,4-dimethyl-benzoyl)-piperidin-4-yl]-1-oxa-3,9-diaza-spiro[5.5]undecan-2-one; compound with trifluoro-acetic acid | 538.8 |
| I-244 | 5-Butyl-3-cyclohexylmethyl-9-[1-(2-methoxy-4-methylsulfanyl-benzoyl)-piperidin-4-yl]-1-oxa-3,9-diaza-spiro[5.5]undecan-2-one; compound with trifluoro-acetic acid | 586.8 |
| I-245 | 5-Butyl-3-cyclohexylmethyl-9-[1-(2-dimethylamino-benzoyl)-piperidin-4-yl]-1-oxa-3,9-diaza-spiro[5.5]undecan-2-one; compound with trifluoro-acetic acid | 553.8 |
| I-246 | 5-Butyl-3-cyclohexylmethyl-9-[1-(3,5-dimethyl-isoxazole-4-carbonyl)-piperidin-4-yl]-1-oxa-3,9-diaza-spiro[5.5]undecan-2-one; compound with trifluoro-acetic acid | 529.8 |
| I-247 | 5-Butyl-3-cyclohexylmethyl-9-[1-(4,6-dimethyl-pyrimidine-5-carbonyl)-piperidin-4-yl]-1-oxa-3,9-diaza-spiro[5.5]undecan-2-one; compound with trifluoro-acetic acid | 540.8 |
| I-248 | 9-[1-(2-Bromo-6-fluoro-benzoyl)-piperidin-4-yl]-5-butyl-3-cyclohexylmethyl-1-oxa-3,9-diaza-spiro[5.5]undecan-2-one; compound with trifluoro-acetic acid | 606.6 |
| I-249 | 9-[1-(1-Benzyl-3,5-dimethyl-1H-pyrazole-4-carbonyl)-piperidin-4-yl]-5-butyl-3-cyclohexylmethyl-1-oxa-3,9-diaza-spiro[5.5]undecan-2-one; compound with trifluoro-acetic acid | 618.8 |
| I-250 | 9-[1-(5-Acetyl-2,4-dimethyl-1H-pyrrole-3-carbonyl)-piperidin-4-yl]-5-butyl-3-cyclohexylmethyl-1-oxa-3,9-diaza-spiro[5.5]undecan-2-one; compound with trifluoro-acetic acid | 569.8 |
| I-251 | 5-Butyl-3-cyclohexylmethyl-9-[1-(2,4,6-trimethoxy-benzoyl)-piperidin-4-yl]-1-oxa-3,9-diaza-spiro[5.5]undecan-2-one; compound with trifluoro-acetic acid | 600.8 |
| I-252 | 5-Butyl-9-[1-(3-chloro-2,6-dimethoxy-benzoyl)-piperidin-4-yl]-3-cyclohexylmethyl-1-oxa-3,9-diaza-spiro[5.5]undecan-2-one; compound with trifluoro-acetic acid | 604.8 |
| I-253 | 5-Butyl-3-cyclohexylmethyl-9-[1-(2-fluoro-6-methoxy-benzoyl)-piperidin-4-yl]-1-oxa-3,9-diaza-spiro[5.5]undecan-2-one; compound with trifluoro-acetic acid | 558.8 |
| I-254 | 5-Butyl-3-cyclohexylmethyl-9-[1-(3,6-dichloro-2-methoxy-benzoyl)-piperidin-4-yl]-1-oxa-3,9-diaza-spiro[5.5]undecan-2-one; compound with trifluoro-acetic acid | 608.8 |
| I-255 | 5-Butyl-3-cyclohexylmethyl-9-[1-(3,5-dimethyl-1-phenyl-1H-pyrazole-4-carbonyl)-piperidin-4-yl]-1-oxa-3,9-diaza-spiro[5.5]undecan-2-one; compound with trifluoro-acetic acid | 604.9 |
| I-256 | 5-Butyl-3-cyclohexylmethyl-9-[1-(2,6-dimethoxy-3-nitro-benzoyl)-piperidin-4-yl]-1-oxa-3,9-diaza-spiro[5.5]undecan-2-onetrifluoro-acetic acid; | 615.8 |
| I-257 | 5-Butyl-3-cyclohexylmethyl-9-[1-(2,4,6-trichloro-benzoyl)-piperidin-4-yl]-1-oxa-3,9-diaza-spiro[5.5]undecan-2-one; compound with trifluoro-acetic acid | 612.7 |
| I-258 | 5-Butyl-9-[1-(3-chloro-2,6-difluoro-benzoyl)-piperidin-4-yl]-3-cyclohexylmethyl-1-oxa-3,9-diaza-spiro[5.5]undecan-2-one; compound with trifluoro-acetic acid | 580.8 |
| I-259 | 5-Butyl-9-[1-(2-chloro-3,6-difluoro-benzoyl)-piperidin-4-yl]-3-cyclohexylmethyl-1-oxa-3,9-diaza-spiro[5.5]undecan-2-one; compound with trifluoro-acetic acid | 580.8 |
| I-260 | 5-Butyl-3-cyclohexylmethyl-9-[1-(2-fluoro-6-trifluoromethyl-benzoyl)-piperidin-4-yl]-1-oxa-3,9-diaza-spiro[5.5]undecan-2-one; compound with trifluoro-acetic acid | 596.8 |
| I-261 | 5-Butyl-9-[1-(6-chloro-2-fluoro-3-methyl-benzoyl)-piperidin-4-yl]-3-cyclohexylmethyl-1-oxa-3,9-diaza-spiro[5.5]undecan-2-one; compound with trifluoro-acetic acid | 576.8 |
| I-262 | 5-Butyl-9-[1-(2-chloro-6-fluoro-3-methyl-benzoyl)-piperidin-4-yl]-3-cyclohexylmethyl-1-oxa-3,9-diaza-spiro[5.5]undecan-2-one; compound with trifluoro-acetic acid | 576.8 |
| I-263 | 5-Butyl-3-cyclohexylmethyl-9-[1-(2,4,6-trifluoro-benzoyl)-piperidin-4-yl]-1-oxa-3,9-diaza-spiro[5.5]undecan-2-one; compound with trifluoro-acetic acid | 564.8 |
| I-264 | 5-Butyl-9-[1-(3-chloro-2-fluoro-6-trifluoromethyl-benzoyl)-piperidin-4-yl]-3-cyclohexylmethyl-1-oxa-3,9-diaza-spiro[5.5]undecan-2-one; compound with trifluoro-acetic acid | 630.8 |
| I-265 | 5-Butyl-3-cyclohexylmethyl-9-[1-(2,3,6-trifluoro-benzoyl)-piperidin-4-yl]-1-oxa-3,9-diaza-spiro[5.5]undecan-2-one; compound with trifluoro-acetic acid | 564.8 |
| I-266 | 5-Butyl-9-[1-(2-chloro-6-nitro-benzoyl)-piperidin-4-yl]-3-cyclohexylmethyl-1-oxa-3,9-diaza-spiro[5.5]undecan-2-onetrifluoro-acetic acid; | 589.8 |
| I-267 | 5-Butyl-9-[1-(2,6-dimethyl-benzoyl)-piperidin-4-yl]-3-ethyl-1-oxa-3,9-diaza-spiro[5.5]undecan-2-one; compound with trifluoro-acetic acid | 470.7 |
| I-268 | 5-Butyl-9-[1-(2,6-dimethyl-benzoyl)-piperidin-4-yl]-3-phenethyl-1-oxa-3,9-diaza-spiro[5.5]undecan-2-one; compound with trifluoro-acetic acid | 546.7 |
| I-269 | 5-Butyl-9-[1-(2,6-dimethyl-benzoyl)-piperidin-4-yl]-3-(2-fluoro-ethyl)-1-oxa-3,9-diaza-spiro[5.5]undecan-2-one; compound with trifluoro-acetic acid | 488.7 |
| I-270 | 5-Butyl-9-[1-(2,6-dimethyl-benzoyl)-piperidin-4-yl]-3-((S)-2-methyl-butyl)-1-oxa-3,9-diaza-spiro[5.5]undecan-2-one; compound with trifluoro-acetic acid | 512.7 |

-continued

| Cpd # | NAME | MS [M + H]+ |
|---|---|---|
| I-271 | 5-Butyl-9-[1-(2,6-dimethyl-benzoyl)-piperidin-4-yl]-3-(3-methyl-butyl)-1-oxa-3,9-diaza-spiro[5.5]undecan-2-one; compound with trifluoro-acetic acid | 512.7 |
| I-272 | 5-Butyl-3-cyclopropylmethyl-9-[1-(2,6-dimethyl-benzoyl)-piperidin-4-yl]-1-oxa-3,9-diaza-spiro[5.5]undecan-2-one; compound with trifluoro-acetic acid | 496.7 |
| I-273 | 5-Butyl-9-[1-(2,6-dimethyl-benzoyl)-piperidin-4-yl]-3-(2-ethyl-butyl)-1-oxa-3,9-diaza-spiro[5.5]undecan-2-one; compound with trifluoro-acetic acid | 526.7 |
| I-274 | 5-Butyl-9-[1-(2,6-dimethyl-benzoyl)-piperidin-4-yl]-3-(2-methyl-benzyl)-1-oxa-3,9-diaza-spiro[5.5]undecan-2-one; compound with trifluoro-acetic acid | 546.7 |
| I-275 | 5-Butyl-3-(2-cyclohexyl-ethyl)-9-[1-(2,6-dimethyl-benzoyl)-piperidin-4-yl]-1-oxa-3,9-diaza-spiro[5.5]undecan-2-one; compound with trifluoro-acetic acid | 552.8 |
| I-276 | 5-Butyl-9-[1-(2,6-dimethyl-benzoyl)-piperidin-4-yl]-3-(2-fluoro-benzyl)-1-oxa-3,9-diaza-spiro[5.5]undecan-2-one; compound with trifluoro-acetic acid | 550.7 |
| I-277 | 5-Butyl-3-cyclobutylmethyl-9-[1-(2,6-dimethyl-benzoyl)-piperidin-4-yl]-1-oxa-3,9-diaza-spiro[5.5]undecan-2-one; compound with trifluoro-acetic acid | 510.7 |
| I-278 | 5-Butyl-9-[1-(2,6-dimethyl-benzoyl)-piperidin-4-yl]-3-(2-methoxy-ethyl)-1-oxa-3,9-diaza-spiro[5.5]undecan-2-one; compound with trifluoro-acetic acid | 500.8 |
| I-279 | 5-Butyl-9-[1-(2,6-dimethyl-benzoyl)-piperidin-4-yl]-3-propyl-1-oxa-3,9-diaza-spiro[5.5]undecan-2-one; compound with trifluoro-acetic acid | 484.8 |
| I-280 | 3,5-Dibutyl-9-[1-(2,6-dimethyl-benzoyl)-piperidin-4-yl]-1-oxa-3,9-diaza-spiro[5.5]undecan-2-one; compound with trifluoro-acetic acid | 498.8 |
| I-281 | 5-Butyl-9-[1-(2,6-dimethyl-benzoyl)-piperidin-4-yl]-3-pyridin-4-ylmethyl-1-oxa-3,9-diaza-spiro[5.5]undecan-2-one; compound with trifluoro-acetic acid | 533.8 |
| I-282 | 5-Butyl-3-(2-dimethylamino-ethyl)-9-[1-(2,6-dimethyl-benzoyl)-piperidin-4-yl]-1-oxa-3,9-diaza-spiro[5.5]undecan-2-one; compound with trifluoro-acetic acid | 513.8 |
| I-283 | 5-Butyl-9-[1-(2,6-dimethyl-benzoyl)-piperidin-4-yl]-3-(2-morpholin-4-yl-ethyl)-1-oxa-3,9-diaza-spiro[5.5]undecan-2-one; compound with trifluoro-acetic acid | 555.8 |
| I-284 | 5-Butyl-9-[1-(2,6-dimethyl-benzoyl)-piperidin-4-yl]-3-(2-piperidin-1-yl-ethyl)-1-oxa-3,9-diaza-spiro[5.5]undecan-2-one; compound with trifluoro-acetic acid | 553.8 |
| I-285 | 5-Butyl-3-cyclopentylmethyl-9-[1-(2,6-dimethyl-benzoyl)-piperidin-4-yl]-1-oxa-3,9-diaza-spiro[5.5]undecan-2-one; compound with trifluoro-acetic acid | 524.8 |
| I-286 | 5-Butyl-9-[1-(2,6-dimethyl-benzoyl)-piperidin-4-yl]-3-(tetrahydro-pyran-4-ylmethyl)-1-oxa-3,9-diaza-spiro[5.5]undecan-2-one; compound with trifluoro-acetic acid | 540.8 |
| I-287 | 5-Butyl-9-[1-(2,6-dimethyl-benzoyl)-piperidin-4-yl]-3-pyridin-3-ylmethyl-1-oxa-3,9-diaza-spiro[5.5]undecan-2-one; compound with trifluoro-acetic acid | 533.4 |
| I-288 | 5-Butyl-9-[1-(2,6-dimethyl-benzoyl)-piperidin-4-yl]-3-pyridin-2-ylmethyl-1-oxa-3,9-diaza-spiro[5.5]undecan-2-one; compound with trifluoro-acetic acid | 533.4 |
| I-289 | 5-Butyl-9-[1-(2,6-dimethyl-benzoyl)-piperidin-4-yl]-3-(tetrahydro-furan-2-ylmethyl)-1-oxa-3,9-diaza-spiro[5.5]undecan-2-one; compound with trifluoro-acetic acid | 526.4 |
| I-290 | 5-Butyl-9-[1-(2,6-dimethyl-benzoyl)-piperidin-4-yl]-3-[1,3]dioxolan-2-ylmethyl-1-oxa-3,9-diaza-spiro[5.5]undecan-2-one; compound with trifluoro-acetic acid | 528.4 |
| I-291 | 5-Butyl-9-[1-(2,6-dimethyl-benzoyl)-piperidin-4-yl]-3-(tetrahydro-pyran-2-ylmethyl)-1-oxa-3,9-diaza-spiro[5.5]undecan-2-one; compound with trifluoro-acetic acid | 540.4 |
| I-292 | 5-Butyl-3-cyclohexylmethyl-9-[1-(2,4-dimethyl-pyridine-3-carbonyl)-piperidin-4-yl]-1-oxa-3,9-diaza-spiro[5.5]undecan-2-one; compound with trifluoro-acetic acid | 539.4 |
| I-293 | 5-Butyl-3-cyclohexylmethyl-9-[1-(2,4,5-trimethyl-thiophene-3-carbonyl)-piperidin-4-yl]-1-oxa-3,9-diaza-spiro[5.5]undecan-2-one; compound with trifluoro-acetic acid | 558.6 |
| I-294 | 5-Butyl-9-[1-(2,6-dimethyl-benzoyl)-piperidin-4-yl]-3-(tetrahydro-furan-3-ylmethyl)-1-oxa-3,9-diaza-spiro[5.5]undecan-2-one; compound with trifluoro-acetic acid | 523.4 |
| I-295 | 5-Butyl-3-cyclohexylmethyl-9-[1-(6-hydroxy-2,4-dimethyl-pyridine-3-carbonyl)-piperidin-4-yl]-1-oxa-3,9-diaza-spiro[5.5]undecan-2-one; compound with trifluoro-acetic acid | 555.4 |
| I-296 | 9-[1-(4-Amino-2,6-difluoro-benzoyl)-piperidin-4-yl]-5-butyl-3-cyclohexylmethyl-1-oxa-3,9-diaza-spiro[5.5]undecan-2-one; compound with trifluoro-acetic acid | 561.4 |
| I-297 | 5-Butyl-3-cyclohexylmethyl-9-[1-(2-methoxy-4,6-dimethyl-pyrimidine-5-carbonyl)-piperidin-4-yl]-1-oxa-3,9-diaza-spiro[5.5]undecan-2-one; compound with trifluoro-acetic acid | 570.4 |
| I-298 | 5-Butyl-3-cyclohexylmethyl-9-[1-(4-fluoro-2,6-dimethyl-benzoyl)-piperidin-4-yl]-1-oxa-3,9-diaza-spiro[5.5]undecan-2-one; compound with trifluoro-acetic acid | 556.4 |
| I-299 | 5-Butyl-3-cyclohexylmethyl-9-[1-(2,4-dimethyl-1-oxy-pyridine-3-carbonyl)-piperidin-4-yl]-1-oxa-3,9-diaza-spiro[5.5]undecan-2-onetrifluoro-acetic acid; | 555.4 |
| I-300 | 5-Butyl-3-cyclohexylmethyl-9-[1-(4,6-dimethyl-2-methylsulfanyl-pyrimidine-5-carbonyl)-piperidin-4-yl]-1-oxa-3,9-diaza-spiro[5.5]undecan-2-one; compound with trifluoro-acetic acid | 586.4 |
| I-301 | 5-Butyl-3-cyclohexylmethyl-9-[1-(4,6-dimethyl-1-oxy-pyrimidine-5-carbonyl)-piperidin-4-yl]-1-oxa-3,9-diaza-spiro[5.5]undecan-2-onetrifluoro-acetic acid; | 556.4 |

-continued

| Cpd # | NAME | MS [M + H]+ |
|---|---|---|
| I-302 | 5-Butyl-3-cyclohexylmethyl-9-[1-(2,3-dihydro-1H-indole-7-carbonyl)-piperidin-4-yl]-1-oxa-3,9-diaza-spiro[5.5]undecan-2-one; compound with trifluoro-acetic acid | 551.5 |
| I-303 | 5-Butyl-3-cyclohexylmethyl-9-[1-(5-methyl-3-phenyl-isoxazole-4-carbonyl)-piperidin-4-yl]-1-oxa-3,9-diaza-spiro[5.5]undecan-2-one; compound with trifluoro-acetic acid | 591.3 |
| I-304 | 5-Butyl-3-cyclohexylmethyl-9-{1-[3-(2,6-dichloro-phenyl)-5-methyl-isoxazole-4-carbonyl]-piperidin-4-yl}-1-oxa-3,9-diaza-spiro[5.5]undecan-2-one; compound with trifluoro-acetic acid | 659.2 |
| I-305 | 9-[1-(Biphenyl-2-carbonyl)-piperidin-4-yl]-5-butyl-3-cyclohexylmethyl-1-oxa-3,9-diaza-spiro[5.5]undecan-2-one; compound with trifluoro-acetic acid | 586.3 |
| I-306 | 5-Butyl-3-cyclohexylmethyl-9-[1-(2-methyl-naphthalene-1-carbonyl)-piperidin-4-yl]-1-oxa-3,9-diaza-spiro[5.5]undecan-2-one; compound with trifluoro-acetic acid | 574.4 |
| I-307 | 5-Butyl-9-{1-[3-(2-chloro-phenyl)-5-methyl-isoxazole-4-carbonyl]-piperidin-4-yl}-3-cyclohexylmethyl-1-oxa-3,9-diaza-spiro[5.5]undecan-2-one; compound with trifluoro-acetic acid | 625.4 |
| I-308 | 5-Butyl-3-cyclohexylmethyl-9-[1-(1,2,3,4-tetrahydro-acridine-9-carbonyl)-piperidin-4-yl]-1-oxa-3,9-diaza-spiro[5.5]undecan-2-one; compound with trifluoro-acetic acid | 615.4 |
| I-309 | 5-Butyl-3-cyclohexylmethyl-9-[1-(2,6-dichloro-4-methanesulfonyl-benzoyl)-piperidin-4-yl]-1-oxa-3,9-diaza-spiro[5.5]undecan-2-one; compound with trifluoro-acetic acid | 656.4 |
| I-310 | 5-Butyl-3-cyclohexylmethyl-9-[1-(quinoline-3-carbonyl)-piperidin-4-yl]-1-oxa-3,9-diaza-spiro[5.5]undecan-2-one; compound with trifluoro-acetic acid | 561.4 |
| I-311 | 5-Butyl-3-cyclohexylmethyl-9-[1-(quinoline-4-carbonyl)-piperidin-4-yl]-1-oxa-3,9-diaza-spiro[5.5]undecan-2-one; compound with trifluoro-acetic acid | 561.4 |
| I-312 | 5-Butyl-3-cyclohexylmethyl-9-[1-(quinoline-6-carbonyl)-piperidin-4-yl]-1-oxa-3,9-diaza-spiro[5.5]undecan-2-one; compound with trifluoro-acetic acid | 561.4 |
| I-313 | 5-Butyl-3-cyclohexylmethyl-9-[1-(2-morpholin-4-yl-benzoyl)-piperidin-4-yl]-1-oxa-3,9-diaza-spiro[5.5]undecan-2-one; compound with trifluoro-acetic acid | 595.5 |
| I-314 | 5-Butyl-3-cyclohexylmethyl-9-[1-(2-morpholin-4-yl-5-pyrrol-1-yl-benzoyl)-piperidin-4-yl]-1-oxa-3,9-diaza-spiro[5.5]undecan-2-one; compound with trifluoro-acetic acid | 660.6 |
| I-315 | 5-Butyl-3-cyclohexylmethyl-9-[1-(quinoline-8-carbonyl)-piperidin-4-yl]-1-oxa-3,9-diaza-spiro[5.5]undecan-2-one; compound with trifluoro-acetic acid | 561.5 |
| I-316 | 5-Butyl-3-cyclohexylmethyl-9-[1-(2-methyl-quinoline-3-carbonyl)-piperidin-4-yl]-1-oxa-3,9-diaza-spiro[5.5]undecan-2-one; compound with trifluoro-acetic acid | 575.5 |
| I-317 | 5-Butyl-9-[1-(2-chloro-4-methyl-6-pyrrolidin-1-yl-benzoyl)-piperidin-4-yl]-3-cyclohexylmethyl-1-oxa-3,9-diaza-spiro[5.5]undecan-2-one; compound with trifluoro-acetic acid | 627.5 |
| I-318 | 5-Butyl-3-cyclohexylmethyl-9-{1-[2-(1,1-dioxo-1$\lambda^6$-thiomorpholin-4-yl)-benzoyl]-piperidin-4-yl}-1-oxa-3,9-diaza-spiro[5.5]undecan-2-one; compound with trifluoro-acetic acid | 643.6 |
| I-319 | 9-[1-(5-Amino-1-phenyl-1H-pyrazole-4-carbonyl)-piperidin-4-yl]-5-butyl-3-cyclohexylmethyl-1-oxa-3,9-diaza-spiro[5.5]undecan-2-one; compound with trifluoro-acetic acid | 591.6 |
| I-320 | 9-{1-[5-Amino-1-(4-methoxy-phenyl)-1H-pyrazole-4-carbonyl]-piperidin-4-yl}-5-butyl-3-cyclohexylmethyl-1-oxa-3,9-diaza-spiro[5.5]undecan-2-one; compound with trifluoro-acetic acid | 621.6 |
| I-321 | 5-Butyl-3-cyclohexylmethyl-9-[1-(1-phenyl-5-trifluoromethyl-1H-pyrazole-4-carbonyl)-piperidin-4-yl]-1-oxa-3,9-diaza-spiro[5.5]undecan-2-one; compound with trifluoro-acetic acid | 644.6 |
| I-322 | 5-Butyl-3-cyclohexylmethyl-9-{1-[1-(4-methoxy-phenyl)-5-trifluoromethyl-1H-pyrazole-4-carbonyl]-piperidin-4-yl}-1-oxa-3,9-diaza-spiro[5.5]undecan-2-one; compound with trifluoro-acetic acid | 674.6 |
| I-323 | 5-Butyl-3-cyclohexylmethyl-9-{1-[1-(2-methoxy-phenyl)-5-trifluoromethyl-1H-pyrazole-4-carbonyl]-piperidin-4-yl}-1-oxa-3,9-diaza-spiro[5.5]undecan-2-one; compound with trifluoro-acetic acid | 674.6 |
| I-324 | 5-Butyl-3-cyclohexylmethyl-9-{1-[2-(4-fluoro-benzyl)-5-methyl-2H-pyrazole-3-carbonyl]-piperidin-4-yl}-1-oxa-3,9-diaza-spiro[5.5]undecan-2-one; compound with trifluoro-acetic acid | 622.6 |
| I-325 | 5-Butyl-9-{1-[1-(4-chloro-phenyl)-5-trifluoromethyl-1H-pyrazole-4-carbonyl]-piperidin-4-yl}-3-cyclohexylmethyl-1-oxa-3,9-diaza-spiro[5.5]undecan-2-one; compound with trifluoro-acetic acid | 678.6 |
| I-326 | 5-Butyl-3-cyclohexylmethyl-9-[1-(1-p-tolyl-5-trifluoromethyl-1H-pyrazole-4-carbonyl)-piperidin-4-yl]-1-oxa-3,9-diaza-spiro[5.5]undecan-2-one; compound with trifluoro-acetic acid | 658.6 |
| I-327 | 5-Butyl-3-cyclohexylmethyl-9-{1-[1-(4-fluoro-phenyl)-5-trifluoromethyl-1H-pyrazole-4-carbonyl]-piperidin-4-yl}-1-oxa-3,9-diaza-spiro[5.5]undecan-2-one; compound with trifluoro-acetic acid | 662.6 |
| I-328 | 9-[1-(5-Amino-1-p-tolyl-1H-pyrazole-4-carbonyl)-piperidin-4-yl]-5-butyl-3-cyclohexylmethyl-1-oxa-3,9-diaza-spiro[5.5]undecan-2-one; compound with trifluoro-acetic acid | 605.6 |

-continued

| Cpd # | NAME | MS [M + H]+ |
|---|---|---|
| I-329 | 9-{1-[5-Amino-1-(4-fluoro-phenyl)-1H-pyrazole-4-carbonyl]-piperidin-4-yl}-5-butyl-3-cyclohexylmethyl-1-oxa-3,9-diaza-spiro[5.5]undecan-2-one; compound with trifluoro-acetic acid | 609.6 |
| I-330 | 9-{1-[5-Amino-1-(2-methoxy-phenyl)-1H-pyrazole-4-carbonyl]-piperidin-4-yl}-5-butyl-3-cyclohexylmethyl-1-oxa-3,9-diaza-spiro[5.5]undecan-2-one; compound with trifluoro-acetic acid | 621.6 |
| I-331 | 5-Butyl-3-cyclohexylmethyl-9-[1-(5-methyl-1-phenyl-1H-pyrazole-4-carbonyl)-piperidin-4-yl]-1-oxa-3,9-diaza-spiro[5.5]undecan-2-one; compound with trifluoro-acetic acid | 590.6 |
| I-332 | 5-Butyl-3-cyclohexylmethyl-9-[1-(5-methyl-1-p-tolyl-1H-pyrazole-4-carbonyl)-piperidin-4-yl]-1-oxa-3,9-diaza-spiro[5.5]undecan-2-one; compound with trifluoro-acetic acid | 604.6 |
| I-333 | 5-Butyl-9-{1-[1-(4-chloro-phenyl)-5-methyl-1H-pyrazole-4-carbonyl]-piperidin-4-yl}-3-cyclohexylmethyl-1-oxa-3,9-diaza-spiro[5.5]undecan-2-one; compound with trifluoro-acetic acid | 624.6 |
| I-334 | 5-Butyl-3-cyclohexylmethyl-9-[1-(5-methyl-2-p-tolyl-2H-pyrazole-3-carbonyl)-piperidin-4-yl]-1-oxa-3,9-diaza-spiro[5.5]undecan-2-one; compound with trifluoro-acetic acid | 604.6 |
| I-335 | 5-Butyl-3-cyclohexylmethyl-9-{1-[2-(4-methoxy-phenyl)-5-methyl-2H-pyrazole-3-carbonyl]-piperidin-4-yl}-1-oxa-3,9-diaza-spiro[5.5]undecan-2-one; compound with trifluoro-acetic acid | 620.6 |
| I-336 | 5-Butyl-3-cyclohexylmethyl-9-[1-(2-methyl-4,5,6,7-tetrahydro-benzofuran-3-carbonyl)-piperidin-4-yl]-1-oxa-3,9-diaza-spiro[5.5]undecan-2-one; compound with trifluoro-acetic acid | 568.6 |
| I-337 | 5-Butyl-3-cyclohexylmethyl-9-[1-(3,5-dimethyl-1H-pyrazole-4-carbonyl)-piperidin-4-yl]-1-oxa-3,9-diaza-spiro[5.5]undecan-2-one; compound with trifluoro-acetic acid | 528.6 |
| I-338 | 9-[1-(2-Bromo-pyridine-3-carbonyl)-piperidin-4-yl]-5-butyl-3-cyclohexylmethyl-1-oxa-3,9-diaza-spiro[5.5]undecan-2-one; compound with trifluoro-acetic acid | 589.5 |
| I-339 | 5-Butyl-3-cyclohexylmethyl-9-[1-(2-fluoro-pyridine-3-carbonyl)-piperidin-4-yl]-1-oxa-3,9-diaza-spiro[5.5]undecan-2-one; compound with trifluoro-acetic acid | 529.6 |
| I-340 | 5-Butyl-9-[1-(3-chloro-pyridine-4-carbonyl)-piperidin-4-yl]-3-cyclohexylmethyl-1-oxa-3,9-diaza-spiro[5.5]undecan-2-one; compound with trifluoro-acetic acid | 545.6 |
| I-341 | 5-Butyl-3-cyclohexylmethyl-9-[1-(2-methoxy-pyridine-3-carbonyl)-piperidin-4-yl]-1-oxa-3,9-diaza-spiro[5.5]undecan-2-one; compound with trifluoro-acetic acid | 541.6 |
| I-342 | 5-Butyl-3-cyclohexylmethyl-9-[1-(2-methanesulfonyl-benzoyl)-piperidin-4-yl]-1-oxa-3,9-diaza-spiro[5.5]undecan-2-one; compound with trifluoro-acetic acid | 588.6 |
| I-343 | 5-Butyl-3-cyclohexylmethyl-9-[1-(2-trifluoromethoxy-benzoyl)-piperidin-4-yl]-1-oxa-3,9-diaza-spiro[5.5]undecan-2-one; compound with trifluoro-acetic acid | 594.6 |
| I-344 | N-{2-[4-(5-Butyl-3-cyclohexylmethyl-2-oxo-1-oxa-3,9-diaza-spiro[5.5]undec-9-yl)-piperidine-1-carbonyl]-phenyl}-methanesulfonamide; compound with trifluoro-acetic acid | 603.6 |
| I-345 | 5-Butyl-3-cyclohexylmethyl-9-[1-(2-methyl-5-trifluoromethyl-oxazole-4-carbonyl)-piperidin-4-yl]-1-oxa-3,9-diaza-spiro[5.5]undecan-2-one; compound with trifluoro-acetic acid | 583.6 |
| I-346 | 9-[1-(2-Amino-6-trifluoromethyl-benzoyl)-piperidin-4-yl]-5-butyl-3-cyclohexylmethyl-1-oxa-3,9-diaza-spiro[5.5]undecan-2-one; compound with trifluoro-acetic acid | 593.6 |
| I-347 | 5-Butyl-3-cyclohexylmethyl-9-[1-(2,6-dimethyl-4-nitro-benzoyl)-piperidin-4-yl]-1-oxa-3,9-diaza-spiro[5.5]undecan-2-onetrifluoro-acetic acid; | 583.6 |
| I-348 | 4-Butyl-3-cyclohexylmethyl-8-[1-(2,6-dimethyl-benzoyl)-4-methyl-piperidin-4-yl]-1-oxa-3,8-diaza-spiro[4.5]decan-2-one; | 538 |
| I-349 | 4-Butyl-3-cyclohexylmethyl-8-[1-(2,6-dimethyl-benzoyl)-azetidin-3-yl]-1-oxa-3,8-diaza-spiro[4.5]decan-2-one; compound with trifluoro-acetic acid | 496 |
| I-350 | 4-Butyl-3-cyclohexylmethyl-8-[1-(2,6-dimethyl-benzoyl)-pyrrolidin-3-yl]-1-oxa-3,8-diaza-spiro[4.5]decan-2-one | 510 |
| I-351 | 4-Butyl-3-cyclohexylmethyl-8-[1-(2,6-dimethyl-benzoyl)-4-isobutyl-piperidin-4-yl]-1-oxa-3,8-diaza-spiro[4.5]decan-2-one | 580 |
| I-352 | 4-Butyl-3-cyclohexylmethyl-8-[1-(2,6-dimethyl-benzoyl)-4-ethyl-piperidin-4-yl]-1-oxa-3,8-diaza-spiro[4.5]decan-2-one | 552 |
| I-353 | 5-Butyl-3-cyclohexylmethyl-9-[1-(4,6-dimethyl-pyrimidine-5-carbonyl)-piperidin-4-yl]-1-oxa-3,9-diaza-spiro[5.5]undecan-2-one | 540 |
| I-354 | 5-Butyl-3-cyclohexylmethyl-9-[1-(4,6-dimethyl-pyrimidine-5-carbonyl)-piperidin-4-yl]-1-oxa-3,9-diaza-spiro[5.5]undecan-2-one; compound with methanesulfonic acid | 540 |
| I-355 | 5-Butyl-3-(4,4-difluoro-cyclohexylmethyl)-9-[1-(2,6-dimethyl-benzoyl)-piperidin-4-yl]-1-oxa-3,9-diaza-spiro[5.5]undecan-2-one | 574 |
| I-356 | 5-Butyl-3-cyclohexylmethyl-9-[1-(2,6-dimethyl-benzoyl)-4-methyl-piperidin-4-yl]-1-oxa-3,9-diaza-spiro[5.5]undecan-2-one; compound with 3,3,3-trifluoro-propionic acid | 552 |

-continued

| Cpd # | NAME | MS [M + H]+ |
|---|---|---|
| I-357 | 5-Butyl-3-cyclohexylmethyl-9-[4-methyl-1-(2,4,5-trimethyl-thiophene-3-carbonyl)-piperidin-4-yl]-1-oxa-3,9-diaza-spiro[5.5]undecan-2-one; compound with trifluoro-acetic acid | 572 |
| I-358 | 5-Butyl-3-cyclohexylmethyl-9-[1-(2-dimethylamino-benzoyl)-4-methyl-piperidin-4-yl]-1-oxa-3,9-diaza-spiro[5.5]undecan-2-one; compound with trifluoro-acetic acid | 567 |
| I-359 | 5-Butyl-9-[1-(2-chloro-6-fluoro-benzoyl)-4-methyl-piperidin-4-yl]-3-cyclohexylmethyl-1-oxa-3,9-diaza-spiro[5.5]undecan-2-one; compound with trifluoro-acetic acid | 577 |
| I-360 | 5-Butyl-3-cyclohexylmethyl-9-[1-(3,5-dimethyl-isoxazole-4-carbonyl)-4-methyl-piperidin-4-yl]-1-oxa-3,9-diaza-spiro[5.5]undecan-2-one; compound with trifluoro-acetic acid | 543 |
| I-361 | 9-[1-(Benzofuran-4-carbonyl)-4-methyl-piperidin-4-yl]-5-butyl-3-cyclohexylmethyl-1-oxa-3,9-diaza-spiro[5.5]undecan-2-one; compound with trifluoro-acetic acid | 564 |
| I-362 | 5-Butyl-3-cyclohexylmethyl-9-[1-(2-fluoro-6-methoxy-benzoyl)-4-methyl-piperidin-4-yl]-1-oxa-3,9-diaza-spiro[5.5]undecan-2-one; compound with trifluoro-acetic acid | 572 |
| I-363 | 5-Butyl-3-cyclohexylmethyl-9-[1-(3,5-dimethyl-1-phenyl-1H-pyrazole-4-carbonyl)-4-methyl-piperidin-4-yl]-1-oxa-3,9-diaza-spiro[5.5]undecan-2-one; compound with trifluoro-acetic acid | 618 |
| I-364 | 5-Butyl-3-cyclohexylmethyl-9-[1-(3,5-dimethyl-1H-pyrazole-4-carbonyl)-4-methyl-piperidin-4-yl]-1-oxa-3,9-diaza-spiro[5.5]undecan-2-one; compound with trifluoro-acetic acid | 542 |
| I-365 | 5-Butyl-3-cyclohexylmethyl-9-[1-(2,4-dimethyl-pyridine-3-carbonyl)-4-methyl-piperidin-4-yl]-1-oxa-3,9-diaza-spiro[5.5]undecan-2-one; compound with trifluoro-acetic acid | 553 |
| I-366 | 5-Butyl-3-cyclohexylmethyl-9-[4-methyl-1-(thiophene-3-carbonyl)-piperidin-4-yl]-1-oxa-3,9-diaza-spiro[5.5]undecan-2-one; compound with trifluoro-acetic acid | 530 |
| I-367 | 5-Butyl-3-cyclohexylmethyl-9-[1-(4-methoxy-thiophene-3-carbonyl)-4-methyl-piperidin-4-yl]-1-oxa-3,9-diaza-spiro[5.5]undecan-2-one; compound with trifluoro-acetic acid | 560 |
| I-368 | 5-Butyl-3-cyclohexylmethyl-9-[1-(furan-3-carbonyl)-4-methyl-piperidin-4-yl]-1-oxa-3,9-diaza-spiro[5.5]undecan-2-one; compound with trifluoro-acetic acid | 514 |
| I-369 | 9-[1-(5-Bromo-furan-3-carbonyl)-4-methyl-piperidin-4-yl]-5-butyl-3-cyclohexylmethyl-1-oxa-3,9-diaza-spiro[5.5]undecan-2-one; compound with trifluoro-acetic acid | 593 |
| I-370 | 5-Butyl-3-cyclohexylmethyl-9-[1-(2-methoxy-4,6-dimethyl-pyrimidine-5-carbonyl)-4-methyl-piperidin-4-yl]-1-oxa-3,9-diaza-spiro[5.5]undecan-2-one; compound with trifluoro-acetic acid | 584 |
| I-371 | 5-Butyl-3-cyclohexylmethyl-9-[1-(4,6-dimethyl-2-phenyl-pyrimidine-5-carbonyl)-4-methyl-piperidin-4-yl]-1-oxa-3,9-diaza-spiro[5.5]undecan-2-one; compound with trifluoro-acetic acid | 630 |
| I-372 | 5-Butyl-3-cyclohexylmethyl-9-[1-(4,6-dimethyl-2-pyridin-4-yl-pyrimidine-5-carbonyl)-4-methyl-piperidin-4-yl]-1-oxa-3,9-diaza-spiro[5.5]undecan-2-one; compound with trifluoro-acetic acid | 631 |
| I-373 | 3-Cyclohexylmethyl-9-[1-(2,6-dimethyl-benzoyl)-piperidin-4-yl]-5-phenyl-1-oxa-3,9-diaza-spiro[5.5]undecan-2-one; compound with trifluoro-acetic acid | 558 |
| I-374 | 5-Butyl-3-cyclohexylmethyl-9-[1-(2,5-dimethyl-furan-3-carbonyl)-4-methyl-piperidin-4-yl]-1-oxa-3,9-diaza-spiro[5.5]undecan-2-one; compound with trifluoro-acetic acid | 542 |
| I-375 | 5-Butyl-3-cyclohexylmethyl-9-[4-methyl-1-(2-methyl-furan-3-carbonyl)-piperidin-4-yl]-1-oxa-3,9-diaza-spiro[5.5]undecan-2-one; compound with trifluoro-acetic acid | 528 |
| I-376 | 5-Butyl-3-cyclohexylmethyl-9-{1-[5-(4-methoxy-phenyl)-2-methyl-furan-3-carbonyl]-4-methyl-piperidin-4-yl}-1-oxa-3,9-diaza-spiro[5.5]undecan-2-one; compound with trifluoro-acetic acid | 634 |
| I-377 | 5-Butyl-3-cyclohexylmethyl-9-{1-[3-(4-methoxy-phenyl)-5-methyl-isoxazole-4-carbonyl]-4-methyl-piperidin-4-yl}-1-oxa-3,9-diaza-spiro[5.5]undecan-2-one; compound with trifluoro-acetic acid | 635 |
| I-378 | 5-Butyl-3-cyclohexylmethyl-9-{1-[1-(4-fluoro-phenyl)-3,5-dimethyl-1H-pyrazole-4-carbonyl]-4-methyl-piperidin-4-yl}-1-oxa-3,9-diaza-spiro[5.5]undecan-2-one; compound with trifluoro-acetic acid | 636 |
| I-379 | N-{3-[4-(5-Butyl-3-cyclohexylmethyl-2-oxo-1-oxa-3,9-diaza-spiro[5.5]undec-9-yl)-4-methyl-piperidine-1-carbonyl]-thiophen-2-yl}-acetamide; compound with trifluoro-acetic acid | 587 |
| I-380 | 5-Butyl-9-{1-[5-(4-chloro-phenyl)-2-methyl-furan-3-carbonyl]-4-methyl-piperidin-4-yl}-3-cyclohexylmethyl-1-oxa-3,9-diaza-spiro[5.5]undecan-2-one; compound with trifluoro-acetic acid | 639 |
| I-381 | 5-Butyl-3-cyclohexylmethyl-9-{1-[1-(3,4-dichloro-phenyl)-3,5-dimethyl-1H-pyrazole-4-carbonyl]-4-methyl-piperidin-4-yl}-1-oxa-3,9-diaza-spiro[5.5]undecan-2-one; compound with trifluoro-acetic acid | 687 |
| I-382 | 5-Butyl-3-cyclohexylmethyl-9-{1-[1-(3,4-dichloro-phenyl)-3,5-dimethyl-1H-pyrazole-4-carbonyl]-4-methyl-piperidin-4-yl}-1-oxa-3,9-diaza-spiro[5.5]undecan-2-one; compound with trifluoro-acetic acid | 687 |

| Cpd # | NAME | MS [M + H]+ |
|---|---|---|
| I-383 | 5-Butyl-9-[1-(5-chloro-4-ethyl-thiophene-3-carbonyl)-4-methyl-piperidin-4-yl]-3-cyclohexylmethyl-1-oxa-3,9-diaza-spiro[5.5]undecan-2-one; compound with trifluoro-acetic acid | 593 |
| I-384 | 5-Butyl-3-cyclohexylmethyl-9-{1-[4,6-dimethyl-2-(2-methyl-thiazol-4-yl)-pyrimidine-5-carbonyl]-4-methyl-piperidin-4-yl}-1-oxa-3,9-diaza-spiro[5.5]undecan-2-one; compound with trifluoro-acetic acid | 651 |
| I-385 | 5-Butyl-3-cyclohexylmethyl-9-[1-(4,6-dimethyl-2-trifluoromethyl-pyrimidine-5-carbonyl)-4-methyl-piperidin-4-yl]-1-oxa-3,9-diaza-spiro[5.5]undecan-2-one; compound with trifluoro-acetic acid | 622 |
| I-386 | 5-Butyl-3-cyclohexylmethyl-9-[1-(4,6-dimethyl-2-methylsulfanyl-pyrimidine-5-carbonyl)-4-methyl-piperidin-4-yl]-1-oxa-3,9-diaza-spiro[5.5]undecan-2-one; compound with trifluoro-acetic acid | 560 |
| I-387 | 5-Butyl-3-cyclohexylmethyl-9-[1-(2,6-dichloro-4-methyl-benzoyl)-4-methyl-piperidin-4-yl]-1-oxa-3,9-diaza-spiro[5.5]undecan-2-one; compound with trifluoro-acetic acid | 607 |
| I-388 | 9-[1-(2-Bromo-6-methyl-benzoyl)-4-methyl-piperidin-4-yl]-5-butyl-3-cyclohexylmethyl-1-oxa-3,9-diaza-spiro[5.5]undecan-2-one; compound with trifluoro-acetic acid | 617 |
| I-389 | 5-Butyl-3-cyclohexylmethyl-9-[1-(2,6-dichloro-4-methanesulfonyl-benzoyl)-4-methyl-piperidin-4-yl]-1-oxa-3,9-diaza-spiro[5.5]undecan-2-one; compound with trifluoro-acetic acid | 671 |
| I-390 | 5-Butyl-3-cyclohexylmethyl-9-[1-(4,6-dimethyl-pyrimidine-5-carbonyl)-4-methyl-piperidin-4-yl]-1-oxa-3,9-diaza-spiro[5.5]undecan-2-one; compound with trifluoro-acetic acid | 554 |
| I-391 | 3-Cyclohexylmethyl-8-[1-(4-methoxy-2,6-dimethyl-benzoyl)-piperidin-4-yl]-4-methyl-1-oxa-3,8-diaza-spiro[4.5]decan-2-one | 512 |
| I-392 | 5-Butyl-3-cyclohexylmethyl-9-[1-(4,6-dimethyl-pyrimidine-5-carbonyl)-piperidin-4-yl]-1-oxa-3,9-diaza-spiro[5.5]undecan-2-one; compound with methanesulfonic acid | 540 |
| I-393 | 5-Butyl-9-[1-(4,6-dimethyl-pyrimidine-5-carbonyl)-piperidin-4-yl]-3-(tetrahydro-pyran-4-ylmethyl)-1-oxa-3,9-diaza-spiro[5.5]undecan-2-one; compound with trifluoro-acetic acid | 542 |
| I-394 | 5-Butyl-3-cyclohexylmethyl-9-[1-(2,4,6-trimethyl-pyrimidine-5-carbonyl)-piperidin-4-yl]-1-oxa-3,9-diaza-spiro[5.5]undecan-2-one; compound with trifluoro-acetic acid | 554.7 |
| I-395 | 5-Butyl-3-cyclohexylmethyl-9-[1-(4,6-dimethyl-2-trifluoromethyl-pyrimidine-5-carbonyl)-piperidin-4-yl]-1-oxa-3,9-diaza-spiro[5.5]undecan-2-one | 608.5 |
| I-396 | 5-Butyl-3-cyclohexylmethyl-9-[1-(4,6-dimethyl-2-methylsulfanyl-pyrimidine-5-carbonyl)-piperidin-4-yl]-1-oxa-3,9-diaza-spiro[5.5]undecan-2-one; compound with trifluoro-acetic acid | 586.5 |
| I-397 | 5-Butyl-9-[1-(4,6-dimethyl-2-methylsulfanyl-pyrimidine-5-carbonyl)-piperidin-4-yl]-3-(tetrahydro-pyran-4-ylmethyl)-1-oxa-3,9-diaza-spiro[5.5]undecan-2-one; compound with trifluoro-acetic acid | 588.5 |
| I-398 | 5-Butyl-3-cyclohexylmethyl-9-[1-(2-methanesulfinyl-4,6-dimethyl-pyrimidine-5-carbonyl)-piperidin-4-yl]-1-oxa-3,9-diaza-spiro[5.5]undecan-2-one | 602.5 |
| I-399 | 5-Butyl-3-cyclohexylmethyl-9-{1-[4,6-dimethyl-2-(pyrimidin-2-ylsulfanyl)-pyrimidine-5-carbonyl]-piperidin-4-yl}-1-oxa-3,9-diaza-spiro[5.5]undecan-2-one | 650.6 |
| I-400 | 5-Butyl-3-cyclohexylmethyl-9-[1-(2-methanesulfinyl-4,6-dimethyl-pyrimidine-5-carbonyl)-piperidin-4-yl]-9-oxy-1-oxa-3,9-diaza-spiro[5.5]undecan-2-onetrifluoro-acetic acid; | 618.5 |
| I-401 | 5-Butyl-3-cyclohexylmethyl-9-{1-[4,6-dimethyl-2-(pyridin-2-yloxy)-pyrimidine-5-carbonyl]-piperidin-4-yl}-1-oxa-3,9-diaza-spiro[5.5]undecan-2-one; compound with trifluoro-acetic acid | 633.6 |
| I-402 | 5-Butyl-3-cyclohexylmethyl-9-[1-(4,6-dimethyl-2-phenoxy-pyrimidine-5-carbonyl)-piperidin-4-yl]-1-oxa-3,9-diaza-spiro[5.5]undecan-2-one; compound with trifluoro-acetic acid | 632.6 |
| I-403 | 5-Butyl-3-cyclohexylmethyl-9-{1-[4,6-dimethyl-2-(pyridin-2-ylsulfanyl)-pyrimidine-5-carbonyl]-piperidin-4-yl}-1-oxa-3,9-diaza-spiro[5.5]undecan-2-one | 649.6 |
| I-404 | 5-Butyl-3-cyclohexylmethyl-9-{1-[4,6-dimethyl-2-(1-methyl-1H-imidazol-2-ylsulfanyl)-pyrimidine-5-carbonyl]-piperidin-4-yl}-1-oxa-3,9-diaza-spiro[5.5]undecan-2-one | 652.6 |
| I-405 | 5-Butyl-3-cyclohexylmethyl-9-{1-[4,6-dimethyl-2-(pyridin-4-yloxy)-pyrimidine-5-carbonyl]-piperidin-4-yl}-1-oxa-3,9-diaza-spiro[5.5]undecan-2-one; compound with trifluoro-acetic acid | 633.6 |
| I-406 | 5-Butyl-3-cyclohexylmethyl-9-{1-[4,6-dimethyl-2-(2-methyl-imidazol-1-yl)-pyrimidine-5-carbonyl]-piperidin-4-yl}-1-oxa-3,9-diaza-spiro[5.5]undecan-2-one; compound with trifluoro-acetic acid | 620.6 |
| I-407 | 5-Butyl-3-cyclohexylmethyl-9-[1-(4,6-dimethyl-2-pyridin-4-yl-pyrimidine-5-carbonyl)-piperidin-4-yl]-1-oxa-3,9-diaza-spiro[5.5]undecan-2-one; compound with trifluoro-acetic acid | 617.6 |
| I-408 | 5-Butyl-3-cyclohexylmethyl-9-[1-(4,6-dimethyl-2-phenyl-pyrimidine-5-carbonyl)-piperidin-4-yl]-1-oxa-3,9-diaza-spiro[5.5]undecan-2-one; compound with trifluoro-acetic acid | 616.7 |

-continued

| Cpd # | NAME | MS [M + H]+ |
|---|---|---|
| I-409 | 5-Butyl-3-cyclohexylmethyl-9-(1-[4,6-dimethyl-2-(2-methyl-thiazol-4-yl)-pyrimidine-5-carbonyl]-piperidin-4-yl}-1-oxa-3,9-diaza-spiro[5.5]undecan-2-one; compound with trifluoro-acetic acid | 637.7 |
| I-410 | 3'-[4-(5-Butyl-3-cyclohexylmethyl-2-oxo-1-oxa-3,9-diaza-spiro[5.5]undec-9-yl)-piperidine-1-carbonyl]-2',4'-dimethyl-biphenyl-4-carboxylic acid; compound with trifluoro-acetic acid | 658.6 |
| I-411 | 9-[1-(2-Amino-4,6-dimethyl-pyrimidine-5-carbonyl)-piperidin-4-yl]-5-butyl-3-cyclohexylmethyl-1-oxa-3,9-diaza-spiro[5.5]undecan-2-one; compound with trifluoro-acetic acid | 555.6 |
| I-412 | 5-Butyl-3-cyclohexylmethyl-9-[1-(2,4-dimethyl-biphenyl-3-carbonyl)-piperidin-4-yl]-1-oxa-3,9-diaza-spiro[5.5]undecan-2-one; compound with trifluoro-acetic acid | 614.6 |
| I-413 | 5-Butyl-3-cyclohexylmethyl-9-[1-(2,6-dimethyl-3-pyridin-4-yl-benzoyl)-piperidin-4-yl]-1-oxa-3,9-diaza-spiro[5.5]undecan-2-one | 615.6 |
| I-414 | 5-Butyl-9-[1-(4,6-dimethyl-2-trifluoromethyl-pyrimidine-5-carbonyl)-4-methyl-piperidin-4-yl]-3-(tetrahydro-pyran-4-ylmethyl)-1-oxa-3,9-diaza-spiro[5.5]undecan-2-one; compound with trifluoro-acetic acid | |
| I-415 | 5-Butyl-9-[1-(4,6-dimethyl-pyrimidine-5-carbonyl)-4-methyl-piperidin-4-yl]-3-(tetrahydro-pyran-4-ylmethyl)-1-oxa-3,9-diaza-spiro[5.5]undecan-2-one; compound with trifluoro-acetic acid | |
| I-416 | 5-Butyl-3-(4,4-difluoro-cyclohexylmethyl)-9-[1-(4,6-dimethyl-2-trifluoromethyl-pyrimidine-5-carbonyl)-4-methyl-piperidin-4-yl]-1-oxa-3,9-diaza-spiro[5.5]undecan-2-one; compound with trifluoro-acetic acid | |
| I-417 | 5-Butyl-3-(4,4-difluoro-cyclohexylmethyl)-9-[1-(4,6-dimethyl-pyrimidine-5-carbonyl)-4-methyl-piperidin-4-yl]-1-oxa-3,9-diaza-spiro[5.5]undecan-2-one; compound with trifluoro-acetic acid | |
| I-418 | 5-Butyl-9-{1-[1-(4-fluoro-phenyl)-3,5-dimethyl-1H-pyrazole-4-carbonyl]-4-methyl-piperidin-4-yl}-3-(tetrahydro-pyran-4-ylmethyl)-1-oxa-3,9-diaza-spiro[5.5]undecan-2-one; compound with trifluoro-acetic acid | |
| I-419 | 5-Butyl-9-{1-[3-(4-methoxy-phenyl)-5-methyl-isoxazole-4-carbonyl]-4-methyl-piperidin-4-yl}-3-(tetrahydro-pyran-4-ylmethyl)-1-oxa-3,9-diaza-spiro[5.5]undecan-2-one; compound with trifluoro-acetic acid | |
| I-420 | (S)-5-Butyl-3-cyclohexylmethyl-9-[1-(2,6-dimethyl-benzoyl)-piperidin-4-yl]-1-oxa-3,9-diaza-spiro[5.5]undecan-2-one | |
| I-421 | (R)-5-Butyl-3-cyclohexylmethyl-9-[1-(2,6-dimethyl-benzoyl)-piperidin-4-yl]-1-oxa-3,9-diaza-spiro[5.5]undecan-2-one | |
| I-422 | 5-Butyl-3-cyclohexylmethyl-9-[1-(4,6-dimethyl-pyrimidine-5-carbonyl)-4-methyl-piperidin-4-yl]-1-oxa-3,9-diaza-spiro[5.5]undecan-2-one; compound with trifluoro-acetic acid | |
| I-423 | [structure shown] | 662 |
| I-424 | 4-Butyl-8-[1-(2,6-dimethyl-benzoyl)-piperidin-4-yl]-3-((S)-3-hydroxy-2-methyl-propyl)-1-oxa-3,8-diaza-spiro[4.5]decan-2-one; compound with trifluoro-acetic acid | 500.9 |

Compound Preparation

The following preparations and examples are given to enable those skilled in the art to more clearly understand and to practice the present invention. They should not be considered as limiting the scope of the invention, but merely as being illustrative and representative thereof.

Efforts have been made to ensure accuracy with respect to numbers used (e.g., amounts, temperatures), but allowance for some experimental error and deviation, including differences in calibration, rounding of numbers, and the like, is contemplated.

Compounds of the present invention can be made by a variety of methods depicted in the illustrative synthetic reaction schemes shown and described below. The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, Volumes 1-21; R. C. LaRock, *Comprehensive Organic Transformations*, 2$^{nd}$ edition Wiley-VCH, New York 1999; *Comprehensive Organic Synthesis*, B. Trost and I. Fleming (Eds.) vol. 1-9 Pergamon, Oxford, 1991; *Comprehensive Heterocyclic Chemistry*, A. R. Katritzky and C. W. Rees (Eds) Pergamon, Oxford 1984, vol. 1-9; *Comprehensive Heterocyclic Chemistry II*, A. R. Katritzky and C. W. Rees (Eds) Pergamon, Oxford 1996, vol.

1-11; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data. Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Some compounds in following schemes are depicted with generalized substituents; however, one skilled in the art will immediately appreciate that the nature of the R groups can varied to afford the various compounds contemplated in this invention. Moreover, the reaction conditions are exemplary and alternative conditions are well known. The reaction sequences in the following examples are not meant to limit the scope of the invention as set forth in the claims.

The 1-oxa-3,8-diaza-spiro[4.5]decan-2-one ring system can be assembled from an N-protected 4-oxo-piperidine derivative. The parent 4-piperidone is commercially available or, alternatively, it can be prepared by cyclization of 3-(2-ethoxycarbonyl-ethylamino)-propionic acid ethyl ester (L. Ruzicka et al., *Helv. Chim, Acta* 1920 3:812). While Scheme 1 is depicted with the benzyloxycarbonyl protecting group 1a (Z=CO₂CH₂Ph), which is readily introduced by standard protocols utilizing benzyloxycarbonyl chloride, one will appreciated that a variety of other well-known nitrogen protecting groups would also suffice (T. W. Greene and P. G. M. Wuts, *Protective Groups in Organic Synthesis*, Wiley & Sons, New York 1999). Construction of the oxazolidinone ring follows the general outline of the route reported by P. W. Smith et al. (*J. Med. Chem.* 1995 38:3772) and J. M. Caroon et al. (*J. Med. Chem.* 1982 24:1320).

SCHEME 1

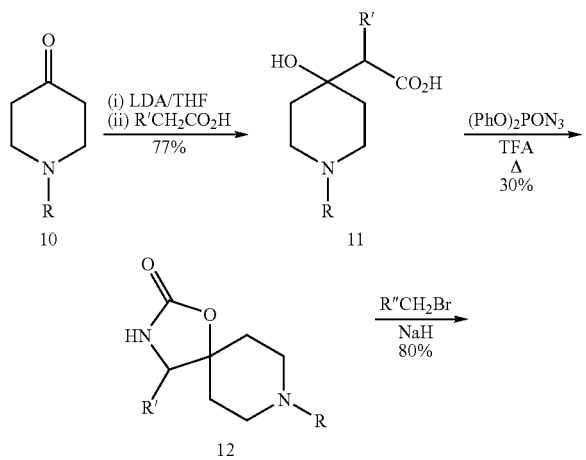

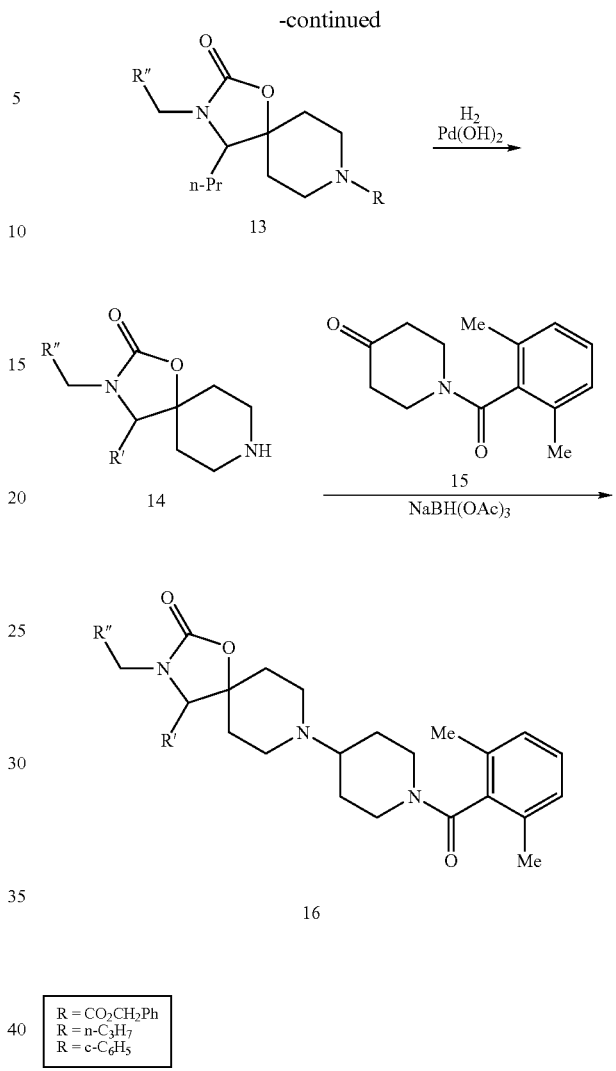

R = CO₂CH₂Ph
R = n-C₃H₇
R = c-C₆H₅

The dianion of butyric acid was treated with 4-oxo-piperidine-1-carboxylic acid benzyl ester to afford the tertiary carbinol 11a. Carboxylic acid dianions (J. C. Stowell, *Carbanions in Organic Synthesis*, Wiley-Interscience, New York, 1979, pp. 127-216; N. Petragnani et al. *Synthesis* 1982 521) are prepared by treating the carboxylic acid with two equivalents of base. While the reaction is conveniently carried out with lithium diisopropylamide, a variety of other non-nucleophilic strong bases, e.g. lithium 2,2',6,6'-tetramethylpiperidide or lithium hexamethyldisilazane can also be used. The base and carboxylic acid are typically combined at −78° C. and the initially formed carboxylate salt warmed to 0 to 20° C. to produce the dianion quantitatively. The reaction is run in polar inert solvents and THF, dioxane, dimethoxyethane are commonly used. By utilizing different carboxylic acids the substituent at the 4-position of the oxazolidone can easily be varied.

A variation of the Curtius reaction is employed to introduce the nitrogen atom and concomitantly generate a reactive acyl species which traps the hydroxyl; group and completes the spiro ring formation. The characteristic feature of the Curtius-type rearrangement of acyl azides is the loss of nitrogen and formation of a positively charged "nitronium ion" which undergoes 1,2-alkyl shift and produces an isocyanate which traps the alcohol. Diphenoxyphosphoryl azide (DPPA) has proven to be a convenient reagent to form the acyl azide in situ. Variations that can be used to convert a carboxylic acid derivative to the corresponding amine include the Hofmann, Schmidt or Lossen reactions (J. March *Advanced Organic Chemistry* 4*th* Ed J Wiley & Sons: New York, 1991; pp 1090-1095; T. Shioiri *Degradation Reactions in Comprehensive Organic Synthesis*, vol. 6, E. Winterfeldt (Ed) Pergamon, Oxford 1991 p. 795-825).

Alkylation of an amide is accomplished by treating the amine or a metal salt of the amine (i.e. a deprotonated form) with a compound $RZ^1$ wherein $Z^1$ is a leaving group such as halo, $C_{1-4}$ alkanesulphonyloxy, benzenesulphonyloxy or p-toluenesulphonyloxy, optionally in the presence of a base and/or a phase transfer catalyst. The reaction may typically be carried out in the presence of a base such as triethylamine or N,N-diisopropylethylamine; DBU (1,8-diazabicyclo[5,4,0]undec-7-ene; or an inorganic base such as $Na_2CO_3$, $NaHCO_3$, $K_2CO_3$ or $Cs_2CO_3$, optionally in the presence of a phase transfer catalyst, and in a solvent such as acetonitrile, DMF, DMSO, 1,4-dioxane, THF or toluene. A metal salt can be formed by treating the amide with a base such as sodium or potassium hydride, lithium diisopropyl amide, potassium tert-butoxide or sodium amylate in a non-protonated solvent such as THF, DMF or 1,4-dioxane which is then treated with a compound $RZ^1$. Introduction of a substituent onto the urethane nitrogen was accomplished by N-alkylation of the sodium salt of the amine which was generated by treating 12 with sodium hydride and subsequently treating the salt with an alkyl halide to afford 13.

Removal of the carbobenzyloxy protecting group is carried out catalytic hydrogenation. The deprotection conditions will, of course, vary with the nature of the N-protecting group. Acidic conditions also can be used to remove a benzyloxycarbonyl protecting group. The tert-butoxycarbonyl is a convenient alternative to the benzyloxycarbonyl protecting group which is removed in treatment with trifluoroacetic acid. One skilled in the art will recognize alternative protecting groups can used interchangeably which may alter the deprotection conditions.

The incorporation of the second piperidine ring is carried out by reductive amination of an N-acyl 4-piperidone. A reductive amination is preferably carried out by combining an amine and carbonyl compound in the presence of a complex metal hydride such as sodium borohydride, lithium borohydride, sodium cyanoborohydride, zinc borohydride, sodium triacetoxyborohydride or borane/pyridine conveniently at a pH of 1-7 optionally in the presence of a dehydrating agent such as molecular sieve or $Ti(IV)(O-i-Pr)_4$ to facilitate formation of the intermediate imine and at ambient temperature or with hydrogen in the presence of a hydrogenation catalyst, e.g. in the presence of palladium/charcoal, at a hydrogen pressure of 1 to 5 bar, preferably at temperatures between 20° C. and the boiling temperature of the solvent used. It may also be advantageous during the reaction if reactive groups are protected during the reaction by conventional protecting groups which are cleaved again by conventional methods after the reaction. Reductive amination procedures have been reviewed: R. M. Hutchings and M. K. Hutchings *Reduction of* C═N *to* CHNH *by Metal Hydrides in Comprehensive Organic Synthesis* col. 8, I. Fleming (Ed) Pergamon, Oxford 1991 pp. 47-54.

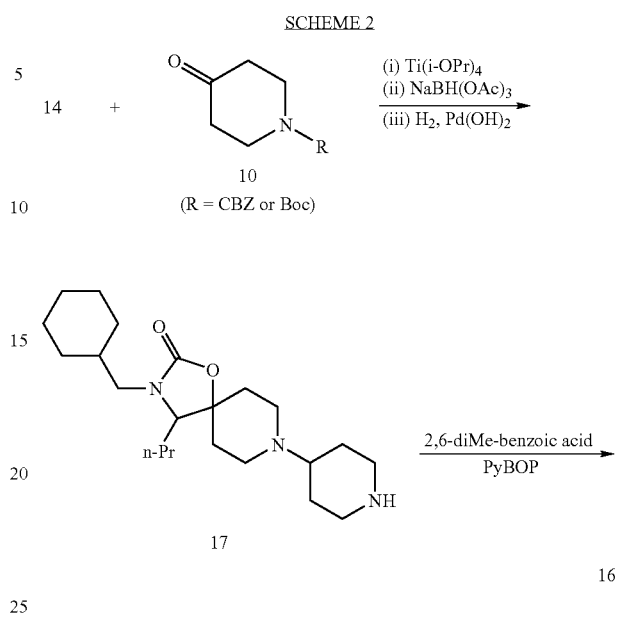

To prepare compound libraries, the availability of an advanced intermediate which can be reacted with a variety of fragments is often advantageous. Thus an alternate scheme (Scheme 2) is comprised of carrying out the reductive alkylation of 14 with 10 (R═CBZ or Boc) Reductive amination and subsequent deprotection of the piperidine nitrogen affords 17. Acylation of the free amine with 2,6-dimethylbenzoic acid affords 16; however, it should be readily apparent that 17 can be acylated or alkylated with a variety of compounds to afford a chemical library with diverse functionality on the piperidine which may be used in lead identification and optimization programs.

Amides of 17 may be formed by conventional amide bond formation techniques such as by first activating a carboxylic acid either as an acid chloride or acid anhydride. The activated acid and the amine 17 may be reacted in the presence of an excess of a suitable base, e.g., $Na_2CO_3$, $NaHCO_3$, $K_2CO_3$, triethylamine or N,N-diisopropylethylamine, and in a suitable solvent, e.g. dichloromethane, ethyl acetate, THF or toluene, with or without water as a co-solvent Alternatively an ester and an amine, or a metal salt thereof, may reacted together in the presence of a base, e.g. triethylamine, and an optional catalyst in a solvent such as dichloromethane, ethyl acetate, THF or toluene. In yet another alternative the acid may be activated with 1-[3-(dimethylamino)propyl]-3-ethyl-carbodiimide hydrochloride (EDCI), 1,1'-carbonyldiimidazole (CDI) or 1,3-dicyclohexylcarbodiimide (DCC) and 1-hydroxy-7-azabenzotriazole (HOAT) or 1-hydroxybenzotriazole hydrate (HOBT), and reacted with the amine in the presence of a base, e.g. triethylamine, in a solvent such as THF, dichloromethane or toluene. One skilled in the art will appreciate there are many alternatives to the reagents identified above which activate a carboxylic acid in like manner. These reactions are typically run at a moderately reduced temperature between about −10 to +10° C. and are typically complete in several hours. The product is recovered by conventional means.

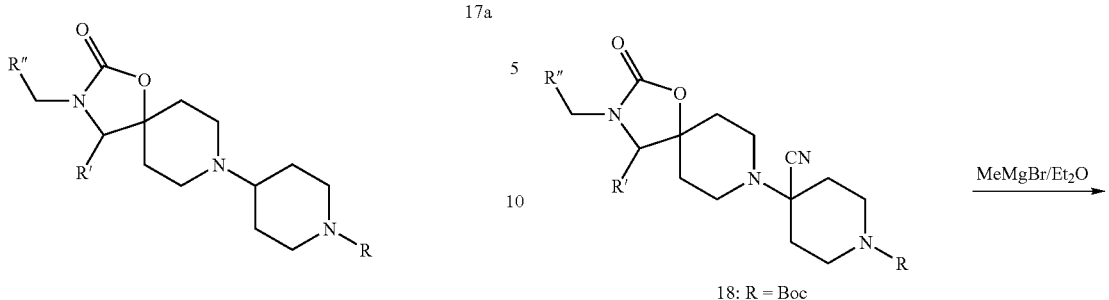

The secondary amine 17 can also be converted to sulfonamides (17a; R=SO$_2$Z$^1$ wherein Z$^1$ is alkyl or aryl) by treating 17 with aryl sulfonyl chlorides under Schotten-Bauman conditions. Ureas and thioureas (17a: R=CONR'R" or CSNHR'R") are also accessible from 17. Procedures for preparing ureas and thioureas have been described (J. Barluenga et al. *Functions Containing a Thiocarbonyl Group Bearing Two Heteroatoms Other than Halogen or a Chalcogen*, in *Comprehensive Organic Functional Group Transformations*, vol. 6, Thomas L. Gilchrist (ed) Elsevier Science Ltd., Oxford UK). Alkyl or aryl isothiocyanates react with ammonia, primary and secondary amines to give 1-substituted, 1,3-disubstituted and trisubstituted thioureas respectively. This reaction generally takes place with good yields and polar solvents such as diethyl ether, ethanol, water and acetone are usually preferred. Alternatively an amine can be treated with phosgene or a phosgene equivalent (e.g. carbonyl diimidazole) and afford an aminocarbonyl chloride which is treated with ammonia, primary or secondary amines. Thioureas are prepared by analogous procedures utilizing isothiocyanates or thiophosgene an equivalent thereof.

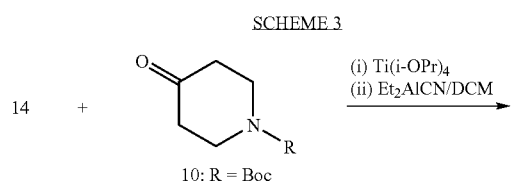

Introduction of a methyl radical at the 4-position was accomplished by treating the intermediate amino nitrile 18 from the Ti(O-i-Pr)$_4$ catalyzed condensation of 14 and N—BOC-4-oxopiperidine with diethylaluminum cyanide and subsequently displacing the nitrile with methyl magnesium bromide to afford 19 (A. Palani et al. J. Med. Chem. 2001 44(21):3339-42).

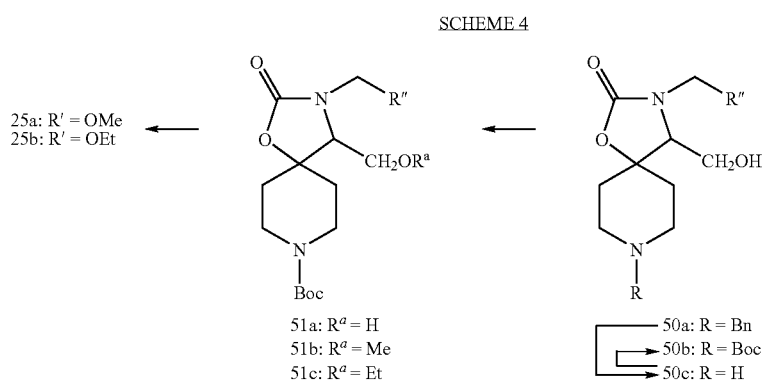

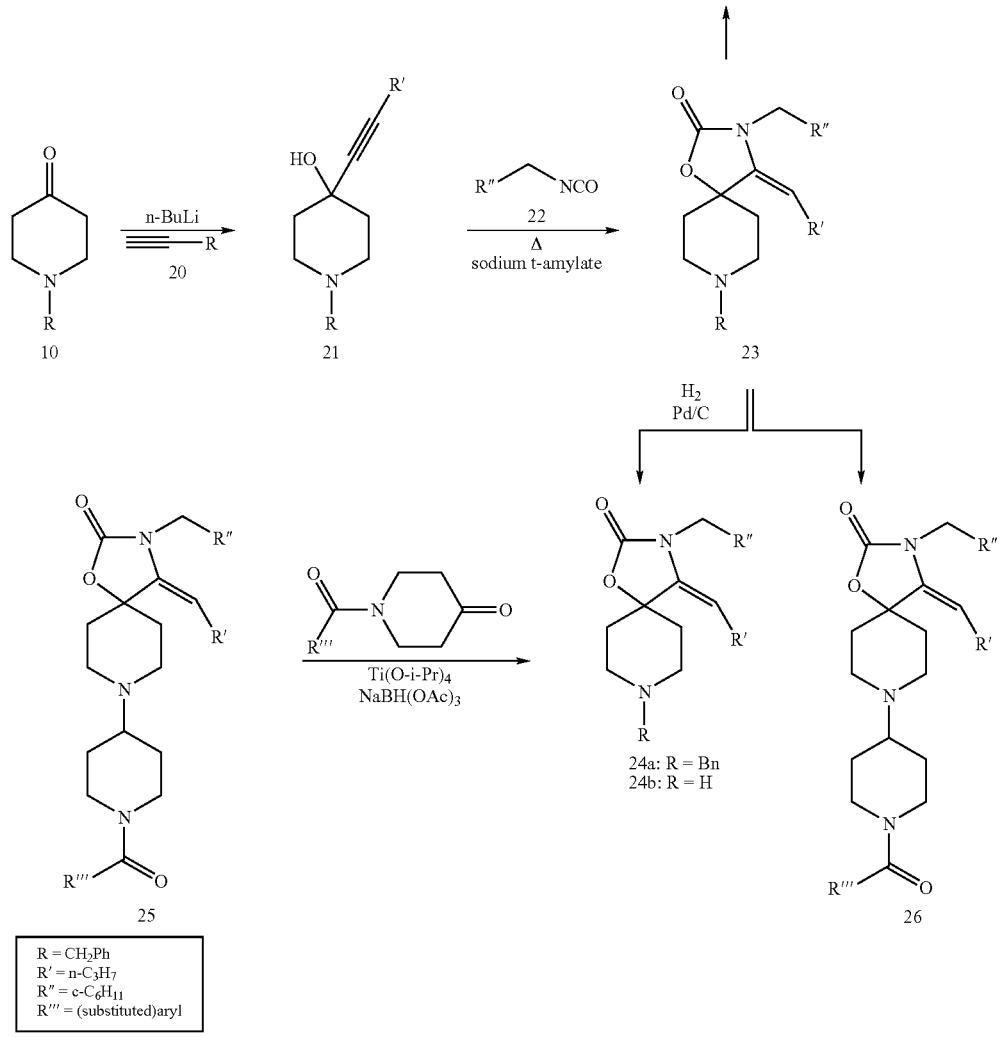

4-Alkylidenyl (23: R'=alkyl), 4-aralkylidenyl (23: R'=aralkyl), 4-heteroarylalkylidenyl (23: R'=heteroarylalkyl) and 4-heterocycloalkylidenyl (23: R'=heterocyclylalkyl) compounds can be prepared by exploiting the susceptibility of acetylenes to nucleophilic attack by nitrogen nucleophiles to afford 4-alkylidene compounds 23 (M. Kimura et al., *Tetrahedron Lett.* 1990 31(30):4887-4890; N. Shachat and J. J. Bagnell, Jr., *J. Org. Chem.* 1963 28:991; S. J. Miller and R. Tanaka, *Nucleophilic Additions to Acetylenes in Selective Organic Transformations*, vol. 1, B. S. Thyagarajan (ed.) Wiley & Sons, New York, N.Y., 1970, p. 143) as depicted in Scheme 4.

Propargyl carbinols 21 are prepared by addition of acetylide anions to N-benzyl-4-piperidone. Acetylide anions are prepared by treating a terminal acetylene with a strong base. Typical strong bases include alkyl lithiums, lithium dialkylamides, lithium hexamethyldisilazane, and sodium hydride. The reaction is run in a polar aprotic solvent such as THF, DME or dioxane at temperatures ranging from −70 to 0° C. The cyclization can be carried out by treating the resulting propargyl carbamate with sodium alkoxide in alcohol solvents to afford 23. Alternatively cyclization can be induced with copper(I) chloride and triethylamine in refluxing THF.

The resulting exocyclic olefins 23 (R=CH₂Ph) are relatively resistant to hydrogenation under mild conditions allowing selective removal of the benzyl protecting group to afford 23 (R=H) which can be converted to compounds of formula 26 by reductive amination as previously described in Schemes 1 and 2. High pressure hydrogenolysis (1000 psi) reduced the exo-olefin while also removing the benzyl protecting group to afford 24 which was converted to piperidines 25 as described previously.

SCHEME 5

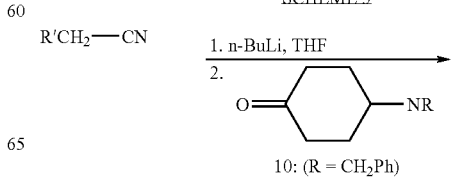

-continued

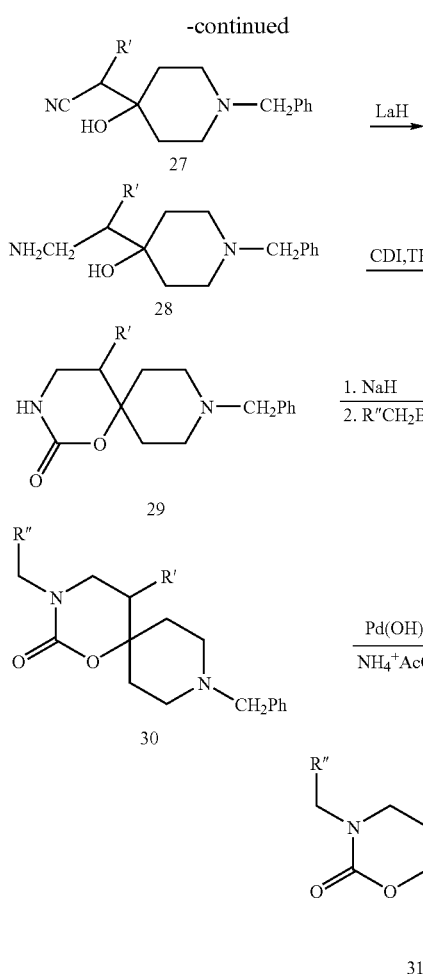

aprotic solvent in the presence of trialkylamine base at temperatures ranging form 0-100° C.

The remainder of the synthesis of 1-oxa-3,9-diaza-spiro[5.5]undecan-2-one compounds of the present invention, including N-alkylation, deprotection of the piperidinyl nitrogen and reductive amination with a suitably N-derivatized 4-oxopiperidine, is carried out utilizing processes analogous to those outlined in Schemes 1 and 2 for 1-oxa-3,8-diaza-spiro[4.5]decan-2-ones.

SCHEME 6

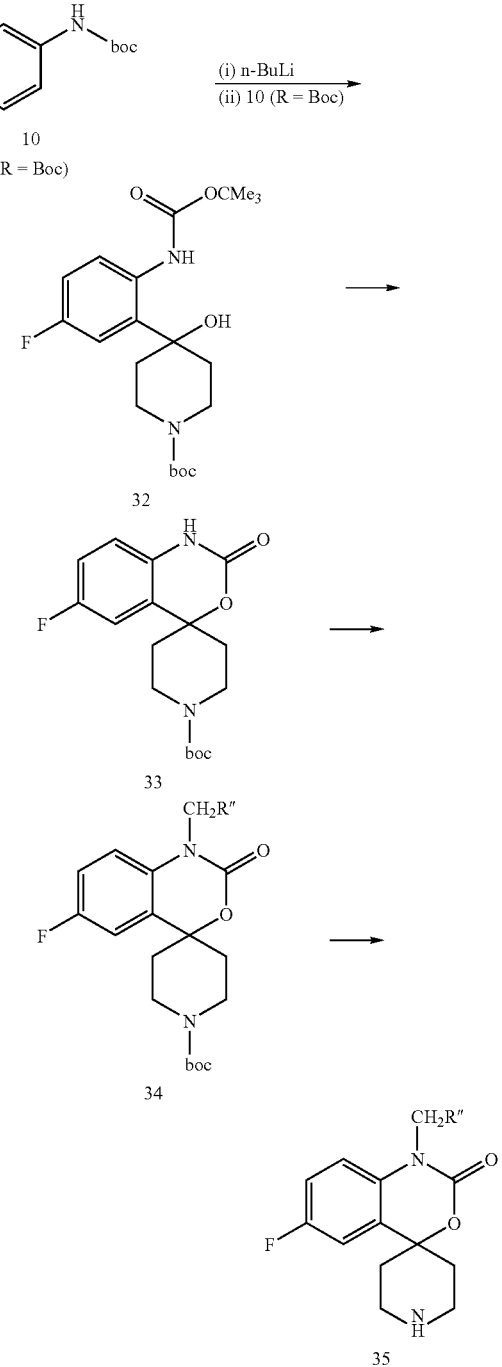

Acylation and alkylation of nitrites is accomplished by deprotonating a nitrile with strong base to form the corresponding nitrile stabilized carbanions. Bases useful for forming a-α-cyano carbanions include lithium dialkyl amides, sodium hexamethyldisilazane, sodium or potassium hydride or potassium amide The reactions are carried out in polar aprotic solvents such as THF, DME and dioxane. The reaction is run from −20 to −78° C. Addition of the N-benzyl piperidin-4-one 10 (R=CH$_2$Ph) compound to the carbanion derived from pentane nitrile afforded hydroxy nitrile 27. (J. March, Adv. Organic Chemistry, John Wiley & Sons, New York, 1992, p. 468-474; S. Arseniyadis et al. Org Reactions 1984 31:1-364; H. O. House, Modern Synthetic Reactions, Benjamin Inc, Menlo Park, Calif. 1972, p. 546-550).

Hydroxy nitrites can be convert amino alcohols with metal hydride reducing agents. (see, R. C. Larock, Comprehensive Organic Transformations, Verlag Chemie, New York, N.Y. 1989, p. 993) Metal hydrides suitable for reduction of nitrites include diborane-THF complex, lithium aluminum hydride and diisobutylaluminum hydride. Diborane reductions are carried out in aprotic ethereal solvents, especially THF. Lithium aluminum hydride reductions can be carried out in THF or diethyl ether. DIBAL reductions are carried out in toluene or THF. DIBAL is available as toluene solutions.

Intramolecular cyclization of the amino alcohol 30 with phosgene or a phosgene equivalent (e.g., carbonyl diimidazole) affords carbamate 29. The reaction is carried out in Benzo-fused 1-oxa-3,9-diaza-spiro[5.5]undecan-2-one compounds are prepared by treating metallated α-aminoalkoxycarbonyl aryl compound 10 with a suitably N-protected 4-oxo-piperidine (Scheme 6). The aminoalkoxycarbonyl radical directs metallation of the aryl ring regiospecifically adjacent to the heteroatom (for analogous ortho metallation of aminoacyl aryl compounds see, H. Takai et al., *Chem. Pharm. Bull.* 1985 33(3):1129-39; W. Fuhrer and H. W. Geschwend, *J. Org. Chem.* 1979 44:113-36) to afford an intermediate alkoxycarbonylamino alcohol compound which spontaneously cyclizes to afford 4,4-disubstitituted 1,4-dihydro-benzo[d][1,3]oxazin-2-one 33. The remainder of the synthesis of benzo-fused 1-oxa-3,9-diaza-spiro[5.5] undecan-2-one compounds of the present invention, including N-alkylation, deprotection of the piperidinyl nitrogen and reductive alkylation with a suitable N-derivatized 4-oxopiperidine 10, is carried out utilizing processes analogous to those outlined in Schemes 1 and 2 for 1-oxa-3,8-diaza-spiro[4.5]decan-2-ones.

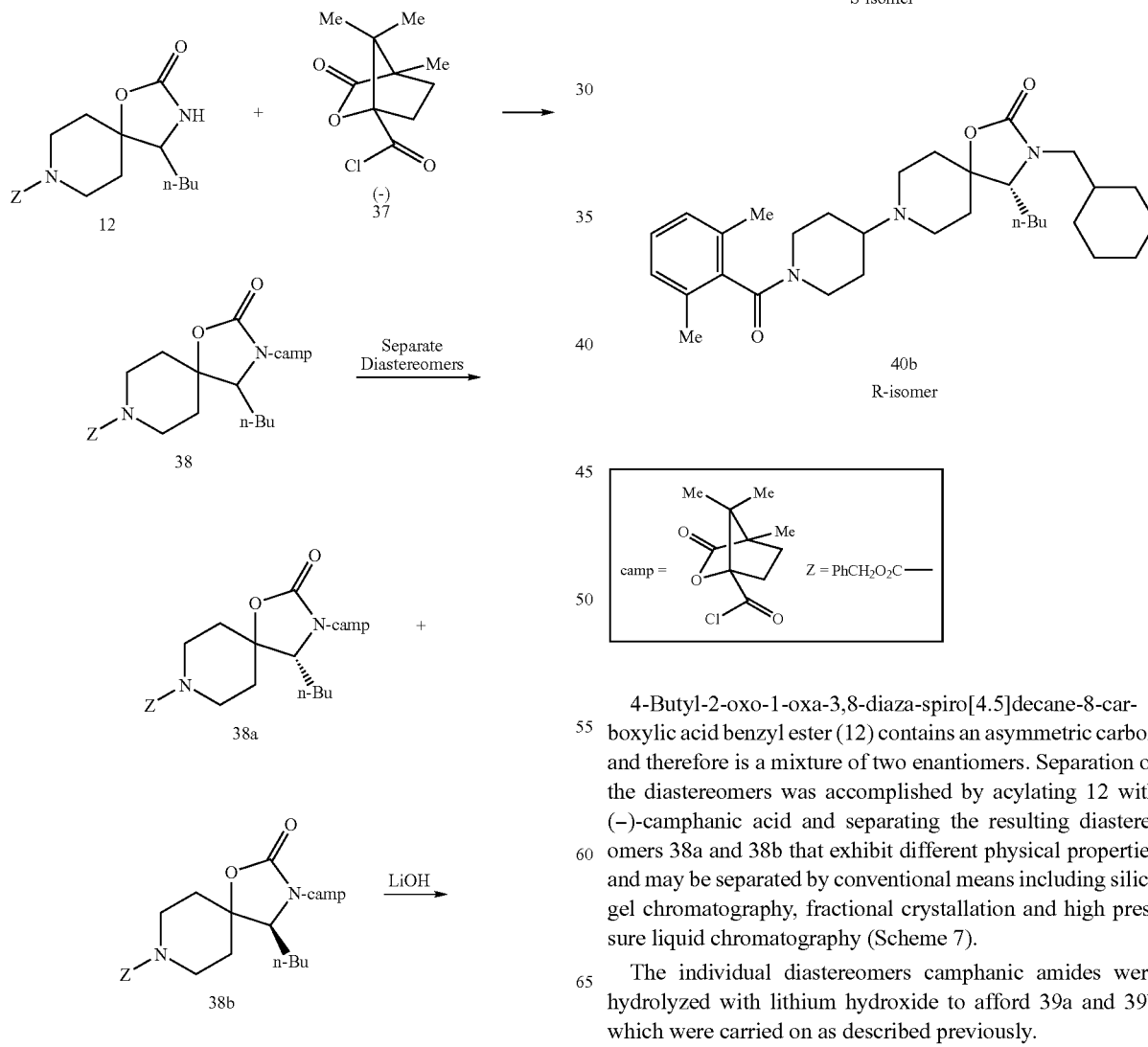

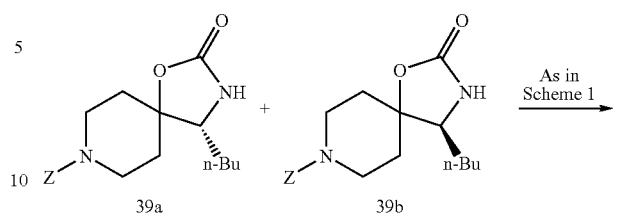

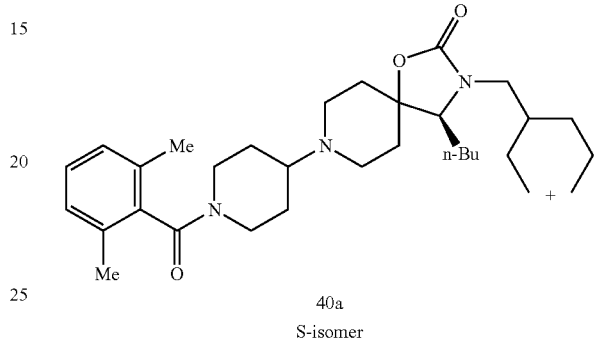

4-Butyl-2-oxo-1-oxa-3,8-diaza-spiro[4.5]decane-8-carboxylic acid benzyl ester (12) contains an asymmetric carbon and therefore is a mixture of two enantiomers. Separation of the diastereomers was accomplished by acylating 12 with (−)-camphanic acid and separating the resulting diastereomers 38a and 38b that exhibit different physical properties and may be separated by conventional means including silica gel chromatography, fractional crystallization and high pressure liquid chromatography (Scheme 7).

The individual diastereomers camphanic amides were hydrolyzed with lithium hydroxide to afford 39a and 39b which were carried on as described previously.

SCHEME 8

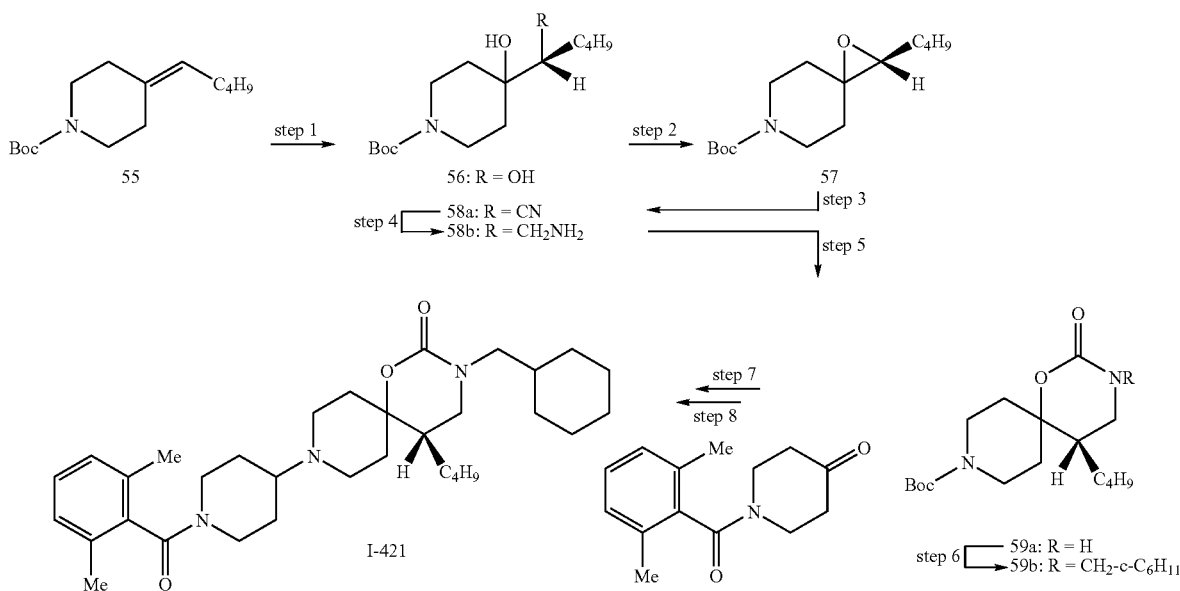

The chiral synthesis of I-421 (SCHEME 8) was achieved utilizing an asymmetric hydroxylation of 55 which was prepared by Wittig olefination of 10 (R=BOC) with pentylidene-triphenyl-$\lambda^5$-phosphane. Asymmetric dihydroxylation is carried out with AD-mix-β which is well know in the art and consists of a premix containing of $K_3Fe(CN)_6$, $K_2CO_3$, $K_2OsO_2(OH)_4$ and hydroquinidine 1,4-diphthalazinediyl diether. Asymmetric hydroxylation is well known in the art and for references see, H. C. Kolb et al. *Chem. Rev.* 1994 94:2483-2547, K. B. Sharpless et al. *J. Org. Chem.* 1992 57:2768-2771. The resulting asymmetric diol 56 was selectively mesylated on the secondary alcohol and converted to epoxide 57. Epoxide-opening mediated by $Et_3AlCN$ afforded the hydroxynitrile 58a which was reduced to amino alcohol 58b and cyclized with phosgene to yield 59a. Introduction of the cyclohexylmethyl substituents (step 6), removal of the Boc protecting group (step 7) and reductive amination with 15 (step 8) affording chiral I-421. While present evidence suggests the isomer obtained from this sequence is the (R) enantiomer, both enantiomers have been prepared and both are with the scope of the present patent.

Dosage and Administration

The compounds of the present invention may be formulated in a wide variety of oral administration dosage forms and carriers. Oral administration can be in the form of tablets, coated tablets, dragées, hard and soft gelatine capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The term "excipient" as used herein includes both one and more than one such excipient.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polyactic acid.

Suitable formulations along with pharmaceutical carriers, diluents and expcipients are described in *Remington: The Science and Practice of pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 100 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

In embodiments of the invention, the active compound or a salt can be administered in combination with another antiviral agent, such as a nucleoside reverse transcriptase inhibitor, another nonnucleoside reverse transcriptase inhibitor or HIV protease inhibitor. When the active compound or its derivative or salt are administered in combination with another antiviral agent the activity may be increased over the parent compound. When the treatment is combination therapy, such administration may be concurrent or sequential with respect to that of the nucleoside derivatives. "Concurrent administration" as used herein thus includes administration of the agents at the same time or at different times. Administration of two or more agents at the same time can be achieved by a single formulation containing two or more active ingredients or by substantially simultaneous administration of two or more dosage forms with a single active agent.

It will be understood that references herein to treatment extend to prophylaxis as well as to the treatment of existing conditions, and that the treatment of animals includes the treatment of humans as well as other animals. Furthermore, treatment of a HIV infection, as used herein, also includes treatment or prophylaxis of a disease or a condition associated with or mediated by HIV infection, or the clinical symptoms thereof.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Example 1

4-Butyl-3-cyclohexylmethyl-8-[1-(2,6-dimethyl-benzoyl)-piperidin-4-yl]-1-oxa-3,8-diaza-spiro[4.5]decan-2-one (I-1)

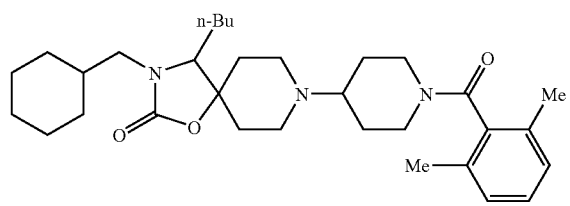

Step 1: 4-(1-Carboxy-pentyl)-4-hydroxy-piperidine-1-carboxylic acid benzyl ester

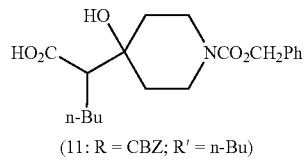

(11: R = CBZ; R' = n-Bu)

To a solution of 15 mL (124 mmol) diisopropyl amine in 90 mL anhydrous THF at −40° C. was added dropwise 45 mL (113 mmol) of n-butyl lithium (2.5 M in hexanes) The reaction mixture was warmed to 0° C. A solution of 6.7 mL (62.1 mmol) hexanoic acid in 60 mL anhydrous THF was added dropwise. The reaction mixture stirred at −20° C. for an additional 20 m. The reaction mixture was cooled to −78° C. A solution of 15 g (64.3 mmol) benzyl 4-oxo-1-piperidine-carboxylate in 60 mL anhydrous THF was added dropwise. The reaction mixture slowly warmed to room temperature over 18 h. The reaction was quenched by addition of 25 mL of water. The mixture was acidified to pH 2 with 6N HCl. The aqueous layer was thrice extracted with EtOAc. The combined organic phase was dried over magnesium sulfate and evaporated under reduced pressure. Toluene was added to the light, yellow oil and evaporated under reduced pressure to provide 21.5 g (99%) of 4-(1-carboxy-pentyl)-4-hydroxy-piperidine-1-carboxylic acid benzyl ester: ms [M]$^+$=350.

Step 2: 4-butyl-2-oxo-1-oxa-3,8-diaza-spiro[4.5]decane-8-carboxylic acid benzyl ester

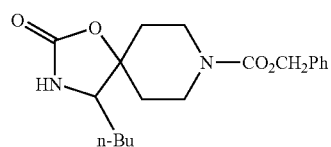

(12: R = CBZ; R' = n-Bu)

To a solution of 27 g of 4-(1-carboxy-pentyl)-4-hydroxy-piperidine-1-carboxylic acid benzyl ester (61.5 mmol) in 500 ml toluene was added sequentially 20.4 mL of TEA (68.5 mmol) and 14.8 mL of diphenyl phosphoryl azide (68.5 mmol) The reaction mixture refluxed under a nitrogen atmosphere for 18 hour.

The reaction mixture was cooled to room temperature and evaporated under reduced pressure. The residue was dissolved in ethyl acetate. The mixture was washed twice with 1 N HCl, twice with saturated sodium bicarbonate, and once with brine. The organic phase was dried over magnesium sulfate and evaporated under reduced pressure. The residue was purified by flash chromatography on silica gel (1:5 EtOAc:DCM) to provide 16.2 g (75%) of 4-butyl-2-oxo-1-oxa-3,8-diaza-spiro[4.5]decane-8-carboxylic acid benzyl ester: ms [M]$^+$=347.

Step 3: 4-butyl-3-cyclohexylmethyl-2-oxo-1-oxa-3,8-diaza-spiro[4.5]decane-8-carboxylic acid benzyl ester

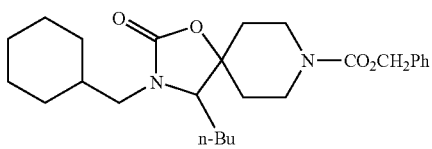

(13: R = CBZ; R' = n-Bu; R" = c-C$_5$H$_{11}$)

To a solution of 5.0 g 4-butyl-2-oxo-1-oxa-3,8-diaza-spiro[4.5]decane-8-carboxylic acid benzyl ester (14.4 mmol) in 50 mL DMF was added 994 mg of sodium hydride (21.6 mmol, 60% dispersion in mineral oil). The reaction mixture stirred for five minutes and 2.2 mL of cyclohexylmethyl bromide (15.8 mmol) was then added. The reaction mixture stirred under nitrogen for 18 h. The reaction mixture was heated to 70° C. for three h. The reaction mixture cooled to room temperature and was diluted with 500 mL EtOAc and washed twice with water, once with brine. The organics were dried over magnesium sulfate and evaporated under reduced pressure. The residue was purified by flash chromatography on silica gel utilizing a gradient elution (10% to 15% EtOAc/DCM) to provide 4.1 g (65%) of 4-butyl-3-cyclohexylmethyl-2-oxo-1-oxa-3,8-diaza-spiro[4.5]decane-8-carboxylic acid benzyl ester: ms [M]$^+$=443.

Step 4: 4-butyl-3-cyclohexylmethyl-1-oxa-3,8-diaza-spiro[4.5]decane-2-one

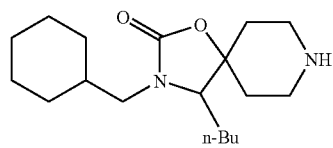

(14: R' = n-Bu; R" = c-C$_5$H$_{11}$)

Palladium on activated carbon (10 mol %; 10% by weight, dry basis, Degussa type) was suspended in a solution of 2.07 g (4.7 mmol) of the 4-butyl-3-cyclohexylmethyl-2-α-1-oxa-3,8-diaza-spiro[4.5]decane-8-carboxylic acid benzyl ester and 50 mL EtOH. The reaction mixture stirred under a hydrogen atmosphere for 18 h. The solution was filtered through a pad of CELITE® to remove the catalyst. Evaporation the EtOH under reduced pressure afforded 1.4 g (95%) of 4-butyl-3-cyclohexylmethyl-1-oxa-3,8-diaza-spiro[4.5]decan-2-one: ms [M]$^+$=309.

Step 5: 4-butyl-3-cyclohexylmethyl-8-[1-(2,6-dimethyl-benzoyl)-piperidin-4-yl]-1-oxa-3,8-diaza-spiro[4.5]decan-2-one

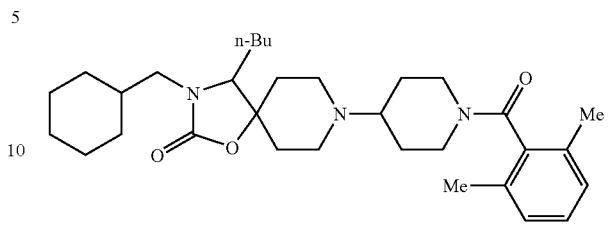

To a solution of 0.75 g (2.4 mmol) of 14 (R=n-Bu; R=c-C$_5$H$_{11}$) and 0.59 g (2.55 mmol) of 15 in 30 mL of dichloroethane was added 1.0 mL (3.4 mmol) of titanium (IV) isopropoxide. The reaction mixture was stirred at RT. After 16 h added 0.77 g (3.85 mmol) of sodium triacetoxyborohydride was added and stirred continued at RT. After 4 h added CELITE® and 15 mL 2N NaOH were added. The mixture was stirred at RT. After 0.5 h, the CELITE® was filtered and washed with dichloromethane and the organic layer separated. The organic layer was washed with brine, dried over sodium sulfate and concentrated. The residue was purified by flash chromatography and eluted with a gradient (50% ethyl acetate/hexane, ethyl acetate, 5% methyl alcohol/ethyl acetate/0.4% ammonium hydroxide) to afford 0.7 g (56%) of I-1 as a white foam.

Example 2

4-(4-Butyl-3-cyclohexylmethyl-2-oxo-1-oxa-3,8-diaza-spiro[4.5]dec-8-yl)-4-methyl-piperidine-1-carboxylic acid (2,6-dimethyl-phenyl)-amide (I-80)

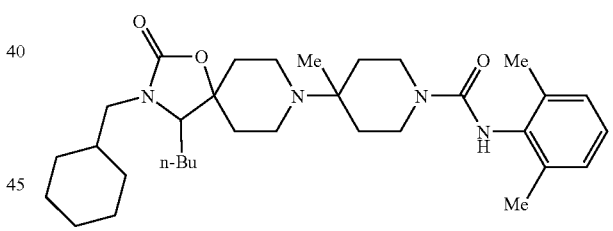

Step 1: 4-(4-Butyl)-3-cyclohexylmethyl-2-oxo-1-oxa-3,8-diaza-spiro[4,5]dec-8-yl)-4-cyano-piperidine-1-carboxylic acid tert-butyl ester (18: R=Boc; R'=n-Bu; R"=c-C$_5$H$_{11}$)

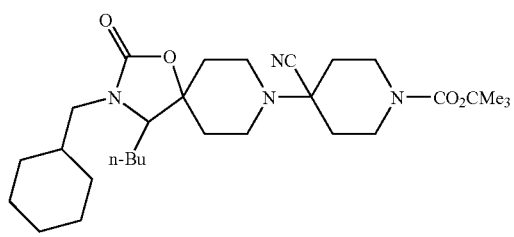

To a solution of 14 (R'=n-Bu; R"=c-C$_5$H$_{11}$; 2.46 mmol) in 60 mL of dichloromethane was added N-Boc-4-piperidone, (10: R=Boc; 515 mg; 2.58 mmol) at RT. The stirred reaction was maintained under a nitrogen atmosphere for 30 m. Ti(IV)(O-i-Pr)$_4$ (1 mL; 3.44 mmol) was added to the reaction and the mixture was stirred at RT for 12 h and then refluxed for 4 h. The reaction mixture was cooled to room temperature and diethylaluminum-cyanide (3.8 mL; 3.87 mmol) was added and stirring was continued for another 5 days. The reaction mixture was diluted with 50 mL of dichloromethane and a few drops of 1N NaOH were added until aluminum granulates could be removed by filtration through CELITE® The organic layer was removed in vacuo and the residue purified on flash chromatography, on silica gel (50% EtOAc/hexane to afford the title compound (933 mg; 78% theory).

Step 2: 4-(4-butyl-3-cyclohexylmethyl-2-oxo-1-oxa-3,8-diaza-spiro[4.5]dec-8-yl)-4-methyl-piperidine-1-carboxylix acid tert-butyl ester (19: R=Boc; R'=n-Bu; R''=c-C$_5$H$_{11}$)

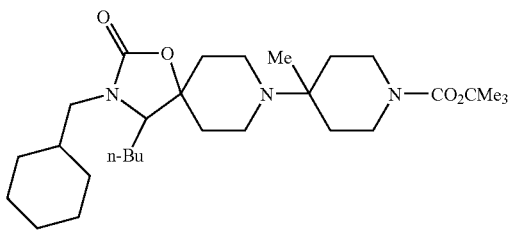

To a solution of 4-(4-butyl-(3-cyclohexylmethyl-2-oxo-1-oxa-3,8-diaza-spiro[4.5]dec-8-yl)-4-cyano-piperidine-1-carboxylic acid tert-butyl ester (18: R=Boc; R'=n-Bu; R''=c-C$_5$H$_{11}$; 700 mg; 1.35 mmol) in 25 mL of THF under nitrogen atmosphere was added with methyl-magnesium-bromide, (1.3 mL; 4.06 mmol; 3.0M solution in Et$_2$O) at RT. The reaction mixture was stirred for 24 h. The reaction was quenched by the addition of water and EtOAc (1:1; 100 mL) and filtered through CELITE®. The organic phase was separated and dried with sodium sulfate, filtered and the solvent evaporated to afford 545 mg (79%) of 19 (R=Boc; R'=n-Bu; R''=c-C$_5$H$_{11}$): ms [M]$^+$=506.

Step 3: 4-butyl-3-cyclohexyl-methyl-8-(4-methyl-piperidin-4-yl)-1-oxa-3,8-diaza-spiro[4.5]decan-2-one 19b (R=n-Bu; R''=c-C$_5$H$_{11}$)

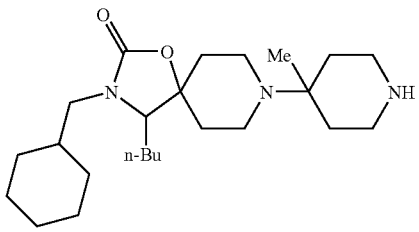

To a solution of 4-(4-butyl-3-cyclohexylmethyl-2-oxo-1-oxa-3,8-diaza-spiro[4.5]dec-8-yl)-4-methyl-piperidine-1-carboxylic acid tert-butyl ester (19a: R=n-Bu; R''=c-C$_5$H$_{11}$; 545 mg; 1.07 mmol) in 20 mL of dichloromethane was added 1 mL of TFA at room temperature and refluxed for 3 h., then stirred for 24 h. at room temperature. The dichloromethane solution was washed with 1N NaOH and water (2×50 ml) and brine (50 ml). The organic layer was separated and dried with sodium sulfate, filtered and the solvent evaporated to afford 300 mg (80% theory) of 19b (R=n-Bu; R''=c-C$_5$H$_{11}$); ms [M]$^+$=406.

Step 4: 4-(4-Butyl-3-cyclohexylmethyl-2-oxo-1-oxa-3,8-diaza-spiro[4.5]dec-8-yl)-4-methyl-piperidine-1-carboxylic acid (2,6-dimethyl-phenyl)-amide (I-80)

A mixture of 2,6-dimethylbenzoic acid (333 mg, 1.47 mmol), HOBT (225 mg, 1.66 mmol) and PS-carbodiimide (610 mg, 196 mmol) in 20 mL of 10% DMF/dichloromethane) was stirred at RT. After 16 h, a solution of 19b (400 mg, 0.98 mmol; R=n-Bu; R''=c-C$_5$H$_{11}$) in 20 mL of DCM was added. The reaction mixture was stirred at RT for 48 h. The resulting mixture was filtered through CELITE® and washed with 110% DMF/DCM. The filtrate was evaporated to dryness under reduced pressure and the crude product was purified by flash chromatography on silica gel (25% MeOH/EtOAc) and the resulting amine converted to the corresponding hydrochloride acid salt with HCl/Et$_2$O to afford I-80 (34.5 mg; 6% theory); ms [M+H]$^+$=538.

Example 3

8-(1-Benzenesulfonyl-piperidin-4-yl)-4-butyl-3-cyclohexylmethyl-1-oxa-3,8-diaza-spiro[4.5]decan-2-one (I-71)

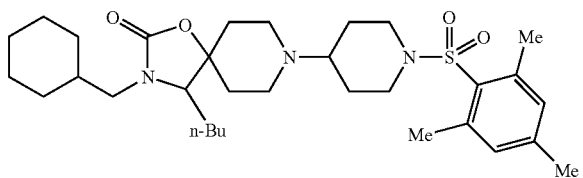

To a solution of 19b (R=n-Bu; R''=c-C$_5$H$_{11}$; 1.0 g; 2.24 mmol), TEA (0.311 mL; 0.226 g; 2.24 mmol) and 25 mL of Et$_2$O was added 1.79 g of toluenesulfonyl chloride (9.78 mmol). The reaction mixture was stirred at RT for 18 h. The solid triethylammonium chloride was filtered and the volatile solvents were evaporated in vacuo. The residue was partitioned between EtOAc and 1N NaOH. The organic layer was washed with water and brine, dried over magnesium sulfate, and evaporated to afford I-71. The crude product was purified by flash chromatography on silica gel.

Example 4

4-Butylidene-3-cyclohexylmethyl-8-[1-(2,6-dimethyl-benzoyl)-piperidin-4-yl]-1-oxa-3,8-diazaspiro[4.5]decan-2-one (I-14)

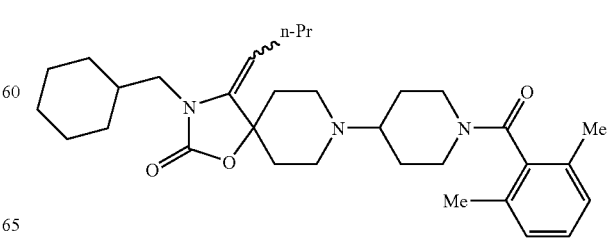

Step 1: 1-Benzyl-4-pent-1-ynyl-piperidin-4-ol

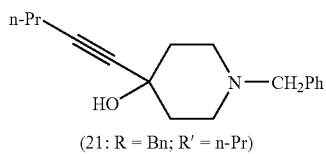

(21: R = Bn; R' = n-Pr)

To a solution of 5.47 g (80.3 mmol) of 1-pentyne in 65 mL THF at −78° C. was added 32.1 ml n-butyl lithium (80.3 mmol; 2.5M in hexanes). After the addition was complete the reaction mixture was warmed to 0° C. and a solution of 8.44 g (44.6 mmol) of 1-benzyl-4-piperidone and 40 mL of THF was added dropwise. The cooling bath was removed and the reaction mixture was stirred at ambient temperature. After 17 h, the reaction was quenched by addition of saturated ammonium chloride and diluted with EtOAc. The aqueous phase was extracted twice with EtOAc. The combined organic phases were washed with brine, dried over sodium sulfate and evaporated to afford a reddish-gold oil. The crude product was purified by flash chromatography on silica gel (EtOAc/hexane 1:1→65:35). The light gold oil was dried over sodium sulfate to afford 8.91 g (78%) of 1-benzyl-4-pentynyl-4-piperidinol: ms (ESI) [M+H]$^+$=258.

Step 2: 8-Benzyl-4-butylidene-3-cyclohexylmethyl-1-oxa-3,8-diaza-spiro[4.5]decan-2-one

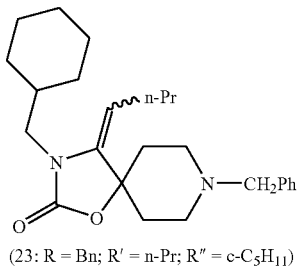

(23: R = Bn; R' = n-Pr; R" = c-C$_5$H$_{11}$)

To a solution of 21 (R=Bn; R'=n-Pr; 1.43 g (5.56 mmol) in 25 mL toluene was added 9.8 mL of potassium t-amylate (16.68 mmol; 1.7 M in toluene). The mixture was heated to 50° C. and a solution of 851 mg (6.11 mmol) of cyclohexylmethylisocyanate (*J. Med. Chem.* 1996 39:1157-1163) in 6 mL toluene was added. The reaction was heated at 70° C. for 17 h, quenched with saturated ammonium chloride and diluted with ethyl acetate. The aqueous phase was washed twice with EtOAc and the combined organic phases washed with brine, dried over sodium sulfate and evaporated to afford a yellow oil. The crude product was purified by flash chromatography on silica gel (EtOAc/hexane 25:75) to afford 190 mg (9%) of 23 (R=Bn; R'=n-Pr; R"=c-C$_5$H$_{11}$) as an unstable light yellow oil: ms (ESI) [M+H]$^+$=397.

Step 3: 4-butylidene-3-cyclohexylmethyl-8-[1-(2,6-dimethyl-benzoyl)-piperidin-4-yl]-1-oxa-3,8-diazaspiro[4.5]decan-2-one (I-14)

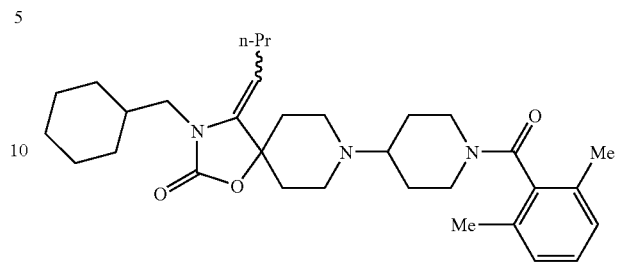

Removal of the benzyl protecting group from 23 (R=Bn; R'=n-Pr; R"=c-C$_5$H$_{11}$) was accomplished by catalytic hydrogenolysis in the presence of 20% Pd(OH)$_2$/C and EtOH at about 40 psi. The final step was carried out as described in step 5 of Example 1. The title compound (I-14) was obtained as a clear glass (3%): MS (ESI) m/z [M+H]$^+$ 522.

Example 5

3-Cyclohexylmethyl-8-[1-(2,6-dimethyl-benzoyl)-piperidin-4-yl]-4-(2-methoxy-ethyl)-1-oxa-3,8-diaza-spiro[4.5]decan-2-one (I-12)

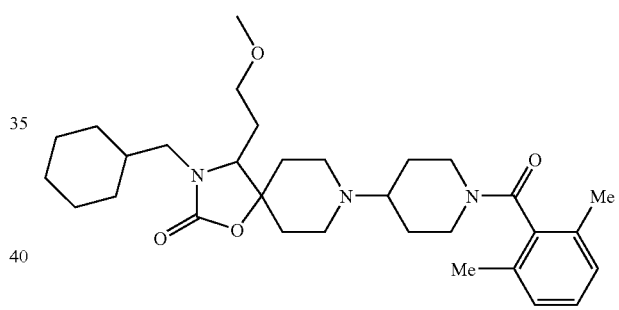

Step 1: 1-Benzyl-4-(3-methoxy-prop-1-ynyl)-piperidin-4-ol

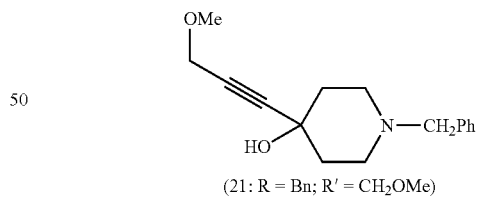

(21: R = Bn; R' = CH$_2$OMe)

To a solution of 4.67 g (66.6 mmol) of 3-methoxypropyne in 50 mL THF at −78° C. was added 26.7 mL n-butyl lithium (66.6 mmol; 2.5M in hexanes). After the addition was complete the reaction mixture was warmed to 0° C. and a solution of 7.01 g (37.0 mmol) of 1-benzyl-4-piperidone and 35 mL THF was added dropwise. The cooling bath was removed and the reaction mixture was stirred at ambient temperature. After 18 h, the reaction was quenched with saturated ammonium chloride and diluted with water and EtOAc. The aqueous phase was washed with EtOAc and the combined organic phases washed sequentially with water and brine. The EtOAc was dried over sodium sulfate, filtered and evaporated in vacuo to afford a reddish-gold oil. The crude product was purified by flash chromatography on silica gel eluting with EtOAc/hexanes (8:2). The gold oil was dried to give 8.30 g (86%) of 21 (R=Bn; R'=CH$_2$OMe): ms (ESI) [M+H]$^+$=260.

Step 2: 8-Benzyl-3-cyclohexylmethyl-4-[2-methoxy-eth-(Z)-ylidene]-1-oxa-3,8-diaza-spiro[4.5]decan-2-one

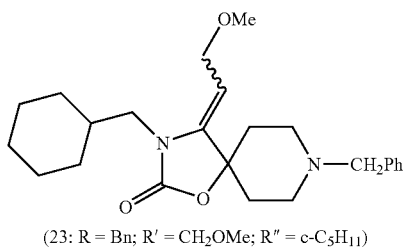

(23: R = Bn; R' = CH$_2$OMe; R'' = c-C$_5$H$_{11}$)

To a solution of 220 mg (0.85 mmol) of 21 (R=Bn; R'=CH$_2$OMe) dissolved in 10 mL toluene was added 1.2 mL of potassium t-amylate (1.88 mmol; 1.7 M in toluene). The mixture was heated to 75° C. and a solution of cyclohexylmethylisocyanate (22: R=c-C$_5$H$_{11}$; 186 mg; 1.88 mmol) in 3 mL toluene was added. The reaction was heated at 75° C. for 17 h, quenched with water and diluted with ethyl acetate. The phases were separated and the aqueous phase washed twice with EtOAc. The combined organic phases were washed with brine, dried over sodium sulfate, filtered and evaporated in vacuo to afford a gold oil. The crude product was purified by flash chromatography on silica gel and eluted with a gradient EtOAc/hexanes (1:1→7:3) to afford 100 mg (29%) of 23 (R=Bn; R'=CH$_2$OMe; R''=c-C$_5$H$_{11}$) as a light yellow oil: ms (ESI) [M+H]$^+$=399.

Step 3: 3-Cyclohexylmethyl-4-(2-methoxy-ethyl)-1-oxa-3,8-diaza-spiro[4.5]decan-2-one

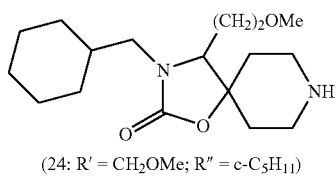

(24: R' = CH$_2$OMe; R'' = c-C$_5$H$_{11}$)

To a solution of 500 mg (1.25 mmol) of 21 (R=Bn; R'=CH$_2$OMe) in 15 mL EtOH was added 200 mg 20% Pd(OH)$_2$ on carbon and 5 drops of HClO$_4$. The mixture was pressurized to 1000 psi of H$_2$ in a steel reactor bomb and stirred at ambient temperature for 17 h. The reaction was filtered over CELITE® and the filter cake was washed with EtOH. The filtrate was evaporated in vacuo and partitioned the residue between 1M NaOH and EtOAc. The organic phase was washed sequentially with water and brine, dried over sodium sulfate and evaporated in vacuo to afford 268 mg (69% theory) of 24 (R'=CH$_2$OMe; R''=c-C$_5$H$_{11}$) as a yellow oil: ms (ESI) [M+H]$^+$=311.

Step 4: 3-Cyclohexylmethyl-8-[1-(2,6-dimethyl-benzoyl)-piperidin-4-yl]-4-(2-methoxy-ethyl)-1-oxa-3,8-diaza-spiro[4.5]decan-2-one

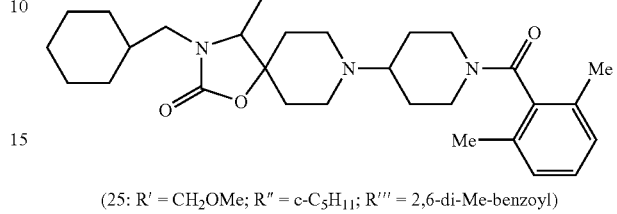

(25: R' = CH$_2$OMe; R'' = c-C$_5$H$_{11}$; R''' = 2,6-di-Me-benzoyl)

Reductive amination was carried out as described in step 5 of example 1. The crude product was purified by flash chromatography eluting with a gradient of methylene chloride/ethanol (45:2→45:4) to afford 46 mg (10% theory) of I-12 as a clear glass: ms (ESI) (M+H)$^+$=526.

Example 6

3-Cyclohexylmethyl-8-[1-(2,6-dimethyl-benzoyl)-piperidin-4-yl]-4-ethoxymethyl-1-oxa-3,8-diaza-spiro[4.5]decan-2-one (I-11)

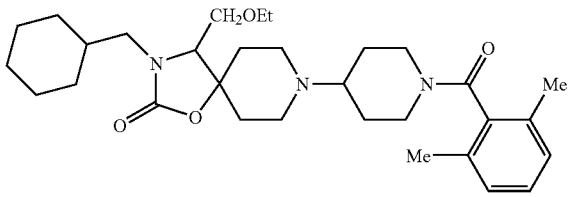

Step 1: 8-benzyl-3-cyclohexylmethyl-4-methylene-1-oxa-3,8-diazaspiro[4.5]decan-2-one

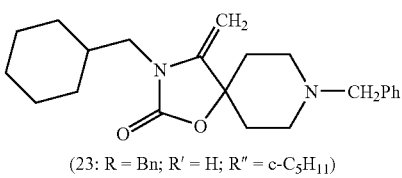

(23: R = Bn; R' = H; R'' = c-C$_5$H$_{11}$)

The title compound was prepared in 57% yield using the procedure described in step 2 of example 3 but substituting 1-benzyl-4-ethynyl-piperidin-4-ol (21: R=Bn; R'=H; J. J. DeVoss, *J. Med. Chem.* 1994 37(5):665) for 1-benzyl-4-pent-1-ynyl-piperidin-4-ol. The crude product was purified by flash chromatography eluting with EtOAc/hexane (1:1) to afford 23 (R=Bn; R'=H; R''=c-C$_5$H$_{11}$) as a yellow syrup: ms (ESI) [M+H]$^+$=355.

Step 2: 8-Benzyl-3-cyclohexylmethyl-4-hydroxymethyl-1-oxa-3,8-diaza-spiro[4.5] decan-2-one

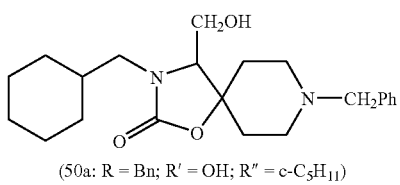

(50a: R = Bn; R' = OH; R'' = c-C$_5$H$_{11}$)

To a solution of 2.0 g (5.64 mmol) of 23 (R=Bn; R'=H; R''=c-C$_5$H$_{11}$) in 100 mL of THF was added 2.75 g (11.28 mmol) of 9-BBN and the reaction was refluxed for 2 h. The reaction was cooled to 0° C. and 30 ml 1M NaOH was added followed by slow addition of 40 mL 30% H$_2$O$_2$. The mixture was stirred at ambient temperature for 1.5 h, poured into a mixture of ice and water and quenched with 1M Na$_2$SO$_3$. The crude mixture was diluted with EtOAc and the aqueous phase was washed two times with EtOAc.

The combined organic extracts were washed twice with 1M Na$_2$SO$_3$ then with water and brine. The organic phase was dried over sodium sulfate, filtered and concentrated in vacuo to afford a yellow oil. The crude product was purified by silica gel flash chromatography eluting with EtOAc/hexanes (85:15) followed by methylene chloride/methanol (9:1) to afford 2.9 g of impure 50a (R''=c-C$_5$H$_{11}$) as a thick gold syrup: ms (ESI) (M+H)$^+$=373.

Step 3: 3-Cyclohexylmethyl-4-hydroxymethyl-1-oxa-3,8-diaza-spiro[4.5]decan-2-one

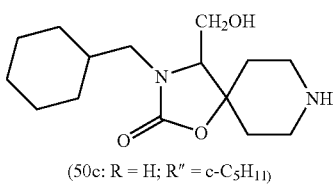

(50c: R = H; R'' = c-C$_5$H$_{11}$)

To a solution of 24a (R=Bn; R'=OH; R''=c-C$_5$H$_{11}$; 2.0 g (5.37 mmol) in 20 mL EtOH was added 200 mg 20% Pd(OH)$_2$ on carbon. The mixture was stirred under balloon pressure of H$_2$ at ambient temperature for 3.5 d. The reaction was filtered through CELITE® and the filter cake washed with EtOH. The solvent was evaporated in vacuo and residue dried to give 1.52 g (100%) of 50c (R''=c-C$_5$H$_{11}$) as a yellow syrup: ms (ESI) (M+H)$^+$=283.

Step 4: 3-cyclohexylmethyl-4-hydroxymethyl-2-oxo-1-oxa-3,8-diaza-spiro[4.5] decane-8-carboxylic acid tert-butyl ester

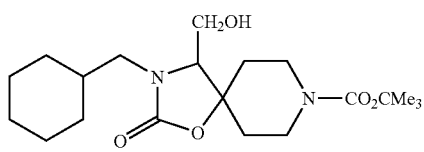

To a solution of 50c (R''=c-C$_5$H$_{11}$; 1.52 g; 5.37 mmol) in 20 mL MeOH and 10 mL 1M NaOH was added (Boc)$_2$O (1.17 g;

5.37 mmol) and the reaction was stirred at ambient temperature for 21 h. The reaction was reduced in volume and diluted with water and EtOAc. The aqueous phase was extracted aqueous two times with EtOAc. The combined organic phases were washed sequentially with water and brine, dried over sodium sulfate and concentrated in vacuo to afford a yellow oil. The crude product was purified by flash chromatography on silica gel eluting with a gradient of EtOAc/hexane (1:1→7:3) to give 650 mg (32%) of 50b (R''=c-C$_5$H$_{11}$) as a clear glass: ms (ESI) (M+H)$^+$=383.

Step 5: 3-Cyclohexylmethyl-4-ethoxymethyl-2-oxo-1-oxa-3,8-diaza-spiro[4.5] decane-8-carboxylic acid tert-butyl ester

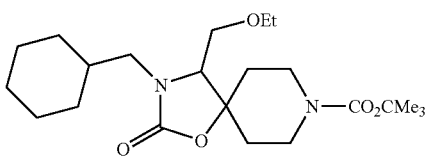

To a suspension of NaH (25 mg; 0.62 mmol; 60% NaH in mineral oil) in 5 mL THF was added a solution of 50b (R''=c-C$_5$H$_{11}$; 217 mg; 0.57 mmol) and 10 mL THF. After 15 minutes, ethyl iodide (97 mg; 0.62 mmol) was added and the reaction was stirred at ambient temperature for 2.5 d. The reaction was quenched with water and diluted with ethyl acetate. The phases were separated and the aqueous phase extracted two times with EtOAc. The combined organic phases were washed sequentially with water and brine, dried over sodium sulfate and concentrated in vacuo to afford a yellow oil. The crude product was purified by flash chromatography on silica gel eluting with EtOAc/hexane (1:1) to give 157 mg (67%) of 51c (R''=c-C$_5$H$_{11}$) as a clear glass: ms (ESI) (M+H)$^+$=411.

Step 6: 3-cyclohexylmethyl-8-[1-(2,6-dimethyl-benzoyl)-piperidin-4-yl]-4-ethoxymethyl-1-oxa-3,8-diaza-spiro[4.5] decan-2-one

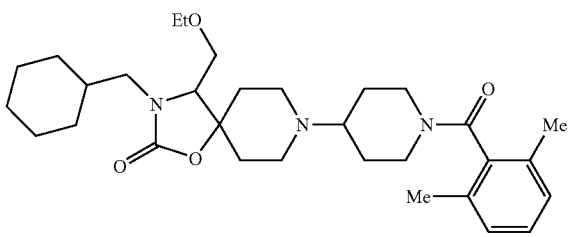

3-Cyclohexylmethyl-8-[1-(2,6-dimethyl-benzoyl)-piperidin-4-yl]-4-ethoxymethyl-1-oxa-3,8-diaza-spiro[4.5]decan-2-one (I-11) was obtained from 51c c-C$_5$H$_{11}$) utilizing the procedures in step 3 of example 2 and step 5 of example 1. The crude product was purified by flash chromatography on silica gel eluting with a gradient of methylene chloride/MeOH (90:1→90:4) to afford 189 mg (95% theory) of I-11 as a clear oil: ms (ESI) (M+H)$^+$=526.

Example 7

5-butyl-3-cyclohexylmethyl-9-(2,6-dimethyl-benzoyl)-1-oxa-3,9-diaza-spiro[5.5] undecan-2-one
(I-76)

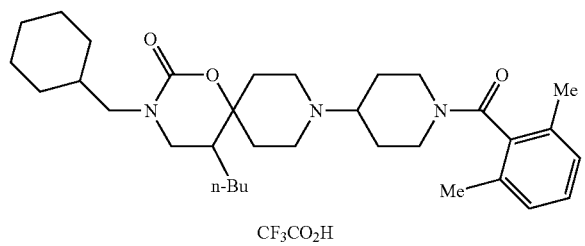

CF₃CO₂H

Step 1: 2-(1-Benzyl-4-hydroxy-piperidin-4-yl)-hexanenitrile

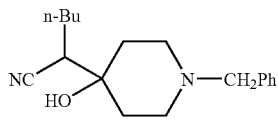

To a solution of 10 g, 12.4 mmol of hexanenitrile in 100 mL of THF at −78° C. was added of n-BuLi (41.2 mL, 103 mmol of 2.5M in hexane) dropwise over 10 m. After 4 h the reaction was poured onto a mixture of saturated NH₄Cl, extracted with EtOAc, the combined EtOAc extracts were washed with brine and the organic layer dried over sodium sulfate. After filtration the solvents were removed in vacuo and the crude residue was purified by flash chromatography on silica gel utilizing a gradient elution of (10-50% EtOAc/hexane) to afford 15.7 g of 27 (R'=n-Bu) as orange oil (53% theory).

Step 2: 9-benzyl-5-butyl-1-oxa-3,9-diaza-spiro[5.5]undecan-2-one

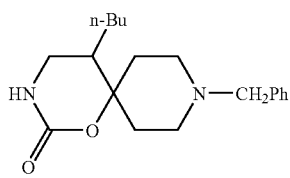

To an ice-cold solution of 10 g, 34.9 mmol 27 (R'=n-Bu) in 100 mL THF was added lithium aluminum hydride (52.4 mL; 52.4 mmol; 1.0 M LAH in THF). After 1 h the reaction was quenched by the addition of 2 mL water, 2 mL 2N NaOH and 6 mL water with stirring. The reaction was stirred for 30 m then filtered and the filtrate washed with EtOAc. The combined organic phases were washed with brine, dried over sodium sulfate and evaporated to dryness. The crude product was taken up in 60 mL of THF and carbonyldiimidazole (17 g, 104.7 mmol) was added. After stirring at for 48 h, the reaction mixture was poured onto brine, the organic layer separated, dried over sodium sulfate and concentrated to dryness. The residue was purified by flash chromatography on silica gel eluting with a gradient (50% EtOAc/hexane to 1% MeOH/EtOAc) to afford 2.3 g of pure 29 (R'=Bu) along with 9 g. of partially purified product.

Step 3: 9-Benzyl-5-butyl-3-cyclohexylmethyl-1-oxa-3,9-diaza-spiro[5.5]undecan-2-one

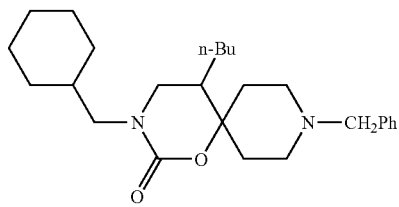

To a solution of 27 (R'=n-Bu; 1.8 g, 19 mmol) in 30 mL of NMP was added NaH (0.27 g, 6.8 mmol). The reaction was stirred at RT. After 30 minutes, cyclohexylmethyl bromide was added (1.2 mL, 8.5 mmol). The reaction mixture was heated to 80° C. for 16 h, cooled to RT and the reaction mixture was poured onto brine. The organic layer separated, dried over sodium sulfate and concentrated to dryness. The residue was purified by flash chromatography on silica eluting with a gradient (10-50% acetone/hexane) to afford 30 (R'=n-Bu; R"=c-C₅H₁₁; 1.5 g; 65% theory).

Step 4: 5-Butyl-3-cyclohexylmethyl-1-oxa-3,9-diaza-spiro[5.5]undecan-2-one

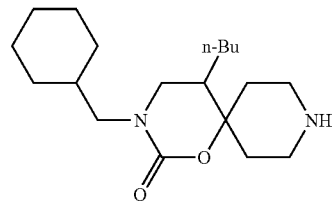

A mixture of 30 (R'=n-Bu; R"=c-C₅H₁₁; 1.5 g, 3.6 mmol), 0.24 g Pd(OH)₂ and 2 ammonium formate (3 g, 36.4 mmol) in 30 mL EtOH was heated at reflux. After 3 h, 10 mL 10% aqueous ammonium hydroxide was added and mixture was reheated to reflux. After 1 h, the reaction mixture was cooled to RT, filtered through CELITE®, washed with EtOH, concentrated to dryness and the residue purified by silica gel flash chromatography eluting with a gradient (EtOAc to 20% MeOH/EtOAc containing 0.4% NH₄OH) to afford 30 (R'=n-Bu; R"=c-C₅H₁₁; 0.92 g, 79% theory) as a clear oil.

The final product 1-76 was prepared by treating piperidine 30 (R'=n-Bu; R"=c-C₅H₁₁) as described in step 5 of Example 1.

Example 8

(I-414)

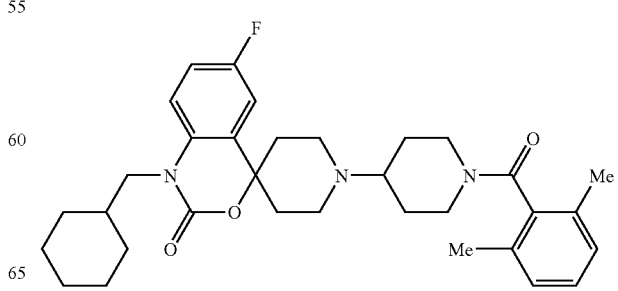

Step 1 (4-fluoro-phenyl)carbamic acid, tert-butyl ester

To a solution of 25 mL p-fluoroaniline (264 mmol) in 400 mL anhydrous THF was added 59.3 g di-tert-butyl dicarbonate (272 mmol) in three portions. The reaction mixture was maintained under a nitrogen atmosphere and heated at reflux for 3 hours. The mixture was cooled to room temperature and the solvent was evaporated under reduced pressure. The residue was dissolved in 300 mL of EtOAc. The organic phase was washed sequentially with 2N HCl and brine, dried over sodium sulfate and the solvent was evaporated in vacuo. The solid was recrystallized from boiling hexanes to provide 47.4 g (85% theory) of (4-fluoro-phenyl)carbamic acid tert-butyl ester (10): ms $M^+=212$.

Step 2: spiro[6-fluoro-4H-3,1-benzoxazine-4,4'-piperidin]-2(1H)-one-carbamic acid tert-butyl ester

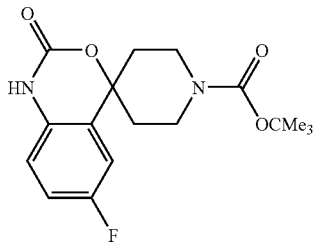

To a solution of (4-fluoro-phenyl)carbamic acid tert-butyl ester (16.0 g; 75.8 mmol) in 300 mL anhydrous THF at −78° C. was added dropwise tert-butyl lithium at a rate sufficient to maintain the internal temperature below −75° C. The reaction mixture stirred at −78° C. for an additional 30 m. The reaction mixture was warmed to −25° C. and stirred for two h. The reaction mixture was cooled back to −78° C. and a solution of 15.1 g of 4-oxo-piperidine-1-carboxylic acid ester (75.8 mmol) in 160 mL anhydrous THF was added dropwise. The reaction mixture stirred at −78° C. for four h. A solution of 1 mL potassium tert-butoxide (1.0 M in tetrahydrofuran) was added. The reaction mixture was allowed to warm to RT slowly over an 18 h period. The crude mixture was diluted with 300 mL Et$_2$O and the organic phase washed sequentially with 2N HCl, water and brine. The organic phase was dried over sodium sulfate and concentrated under in vacuo. The residue was triturated with EtOAc to provide 10.61 g (42%) of spiro[4H-3,1-benzoxazine-4,4'-piperidin]-2(1H)-one-BOC (33) as a solid: ms $M^+=337$.

Step 3: 4-cyclohexylmethyl-spiro[6-fluoro-4H-3,1-benzoxazine-4,4'-piperidin]-2(1H)-one-carbamic acid tert-butyl ester

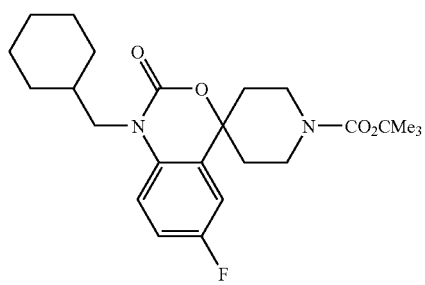

To a solution of 2.0 g of 33 (5.9 mmol) in 40 mL DMF was added 492 mg sodium hydride (10.7 mmol, 60% dispersion in mineral oil). The reaction mixture stirred for one h and 1.86 mL cyclohexylmethyl bromide (13.3 mmol) was added dropwise. The reaction mixture was heated to 70° C. for 18 h, then cooled to room temperature and diluted with 200 mL of water. The mixture was extracted thrice with EtOAc. The organics were combined, dried over sodium sulfate and concentrated under reduced pressure. The residue was purified by flash chromatography on silica gel (10% EtOAc/hexanes) to afford 1.21 g (47%) of 34 (R″=c-C$_5$H$_{11}$): ms $M^+=433$.

Step 4: 3-cyclohexylmethyl-spiro[4H-3,1-6-fluorobenzoxazine-4,4'-piperidin]-2(1H)-one

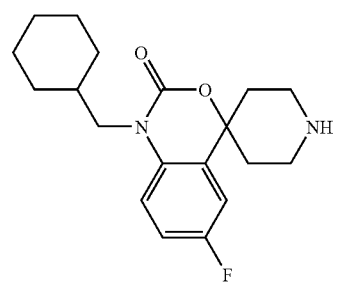

To a solution of 1.2 g of 34 (R″=c-C$_5$H$_1$; 2.8 mmol) in 10 mL dichloromethane was added 10 mL TFA. The reaction mixture stirred under a nitrogen atmosphere for 18 hours. The solvent was removed under reduced pressure to afford the trifluoroacetic acid salt of 35 (R″=c-C$_5$H$_{11}$). The trifluoroacetate salt was dissolved in 20 mL dichloromethane and 20 mL of aqueous saturated sodium bicarbonate was added. The reaction mixture stirred for 20 m after which 40 mL of dichloromethane was added. The organic layer was separated and the aqueous layer was extracted with dichloromethane. The combined organic layers were dried over sodium sulfate and concentrated under in vacuo to afford 918 mg (99%) of 35 (R″=c-C$_5$H$_{11}$): ms $M^+=333$.

Reductive amination with N-(2,6-dimethylbenzoyl)-4-piperidone to afford I-423 was carried out as described in step 5 of Example 1

Example 9

4-Butyl-8-[1-(2,6-dimethyl-benzoyl)-piperidin-4-yl]-3-(2-methoxy-ethyl)-1-oxa-3,8-diaza-spiro[4.5]decan-2-one; compound with trifluoro-acetic acid (I-81)

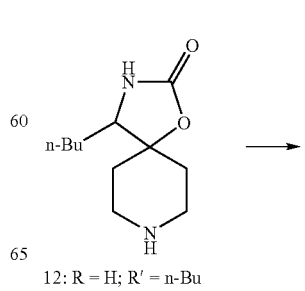

12: R = H; R′ = n-Bu

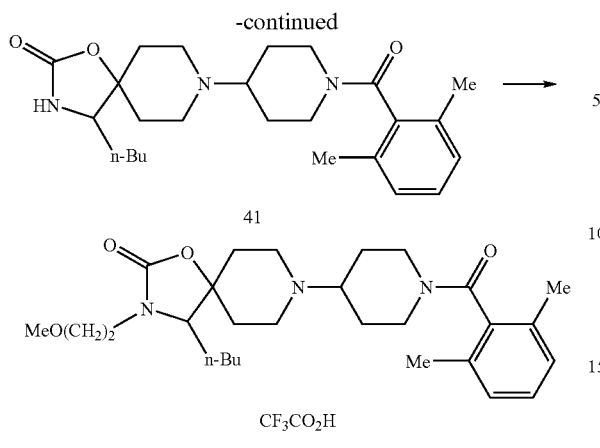

41

CF₃CO₂H

Step 1: 4-Butyl-1-oxa-3,8-diazaspiro[4.5]decane-2-one 2.0 g (5.8 mmol) of 4-butyl-2-oxo-1-oxa-3,8-diaza-spiro [4.5]decane-8-carboxylic acid benzyl ester 12 (R=CBZ; R'=n-Bu) was dissolved in 25 mL of EtOH and Pd/C (10 mol %; 10% by weight, dry basis, Degussa type) was added. The reaction mixture stirred under a hydrogen atmosphere for 18 h. The solution was filtered through a pad of CELITE® and washed twice with EtOH. Evaporation of the combined filtrate and washes under reduced pressure yielded 1.09 g (88%) of 4-butyl-1-oxa-3,8-diaza-spiro[4.5]decane-2-one 12 (R=H; R'=n-Bu): ms [M]⁺=213.

Step 2: 4-butyl-8-[1-(2,6-dimethyl-benzoyl)-piperidinyl-4-yl]-1-oxa-3,8-diazaspiro[4.5] decan-2-one To a solution of 4-butyl-1-oxa-3,8-diaza-spiro[4.5]decane-2-one (12: R=H; R'=n-Bu; 1.09 g; 5.1 mmol)) in 30 mL DCM was added 1.24 g (5.4 mmol) of 1-(2,6-dimethyl-benzoyl)-piperidin-4-one followed by 2.1 mL (7.1 mmol) of Ti(IV)(O-i-Pr)₄ The reaction mixture stirred under nitrogen for 18 h. of Sodium triacetoxyborohydride (1.6 g: 7.7 mmol) was added to the reaction mixture followed by glacial HOAc (0.365 mL; 6.4 mmol). The reaction mixture stirred for 24 h. Aqueous ammonia (20 mL; 10% aqueous solution) was added and the solution stirred for an additional 10 min. The mixture was filtered by gravity through a cartridge of ChemElute™. The organics were evaporated under reduced pressure and the residue was purified by flash chromatography on silica gel with gradient elution (2% to 10% methanol in ethyl acetate with 0.4% ammonia) to provide 1.6 g (73%) of 4-butyl-8-[1-(2,6-dimethyl-benzoyl)-piperidin-4-yl]-1-oxa-3,8-diaza-spiro[4.5]decane-2-one: ms [M]⁺=428.

Step 3: 5-butyl-3-(2-methoxyethyl)-9-[2-(2,6-dimethyl-benzoyl)-piperidin-4-yl]-1-oxa-3,9-diaza-spiro[5.4]decan-2-one To a solution of 21 mg (0.05 mmole) of 4-butyl-8-[1-(2,6-dimethyl-1-benzoyl) -piperidin-4-yl]-1-oxa-3,8-diazaspiro [4.5]decane-2-one dissolved in 1 mL of dry 1,4-dioxanes in a screw-capped test tube was added 100 mg of 10% KF on alumina and 7.1 uL (0.075 mmole) of 2-bromoethylmethyl ether. The tube was sealed and heated at 110° C. for 18 h. The reaction was filter through CELITE® and the filter bed was washed methylene chloride (3×0.5 mL). The combine filtrate and washes were concentrated under reduced pressure. The residue was purified using reverse-phase semi-preparatory HPLC on Aquisil with gradient elution (10%-90% acetonitrile/0.1% aqueous TFA buffer) which afforded 16 mg (52%) of I-81 as the trifluoroacetate salt.

Example 10

Resolution of Enantiomers

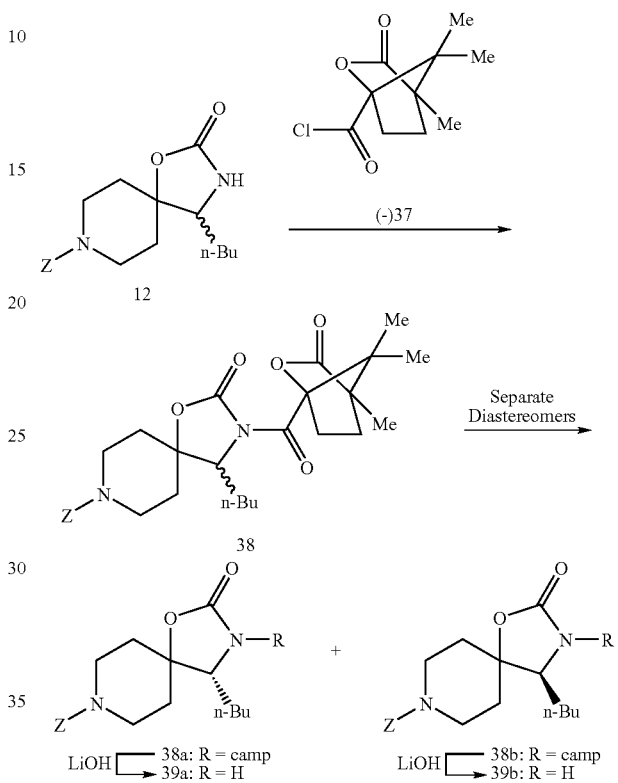

Step 1

To a solution of 600 mg (1.73 mmol) of 12 (R=Z; R'=n-Bu) in 10 mL THF at −78° C. was added n-BuLi (0.70 mL; 1.90 mmol; 2.5M in hexanes). The reaction mixture was stirred at −78° C. for 30 min followed by dropwise addition of (1S)(−)-camphanic acid chloride (412 mg; 1.90 mmol) dissolved in 3 ml THF. The reaction mixture was stirred at −78° C. for 15 min, then ambient temperature for 4 h. The reaction was quenched with saturated ammonium chloride and diluted with EtOAc and water. The phases were separated and the aqueous extracted three times with EtOAc. The combined organic extracts were washed sequentially with saturated NaHCO₃, water and brine, dried over sodium sulfate and evaporated to a gold oil. The diastereomers (38a and 38b) were separated by flash chromatography eluting with a gradient of hexane/EtOAc (8:2 to 7:3) to afford 150 mg (16%) of the more nonpolar isomer was isolated as a colorless thick oil: ms (ESI) [M+H]⁺=527. A second fraction of 210 mg (23%) of the less nonpolar isomer was isolated as a white crystalline solid: ms (ESI) [M+H]⁺=527.

Step 2

To a solution of 210 mg (0.40 mmol) of 38a or 38b from step 1 in 6 mL THF and 2 mL water at 0° C. was added LiOH monohydrate (36 mg; 0.86 mmol). After stirring at 0° C. for 2 h, the THF was stripped and the residue was diluted with saturated NaHCO₃ and ether. The phases were separated and the aqueous extracted two times with ether. The combined extracts were washed with brine, dried over sodium sulfate and evaporated to an off-white powder which was dried in vacuo to afford 135 mg (97%) of the carbamate 39: ms (ESI) [M+H]⁺=347.

The resolved oxazolinones 39a and 39b are converted to (R)- and (S)-I-1 as described in Example 1.

Example 11

Chiral synthesis of (S) 5-butyl-3-cyclohexylmethyl-9-[1-(2,6-dimethylbenzoyl)-piperidin-4-yl]-1-oxa-3,9-diazospiro[5.5]undecan-2-one (SCHEME 8)

I-421

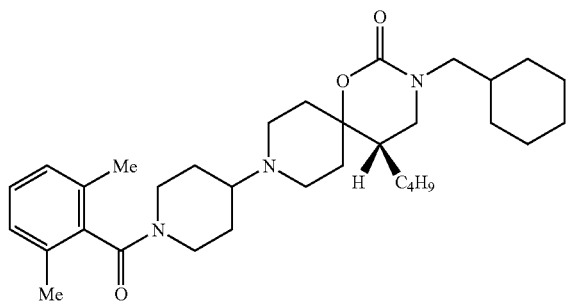

To a solution of 85.18 g (206.0 mmol) of pentyltriphenylphosphine bromide in THF (330 mL) cooled to −78° C. was added n-butyl lithium (80.8 mL, 201.9 mmol, 2.5M butyl lithium in hexanes). After 30 min, a solution of 1-BOC-4-piperidone (38.99 g, 195.7 mmol) in THF (175 mL) was added dropwise over 30 min. The cooling bath was removed and the reaction mixture was stirred at RT. After 17 h, the reaction was quenched with saturated NH₄Cl and diluted with EtOAc. Water was added until two clear phases were obtained. The aqueous phase was extracted twice with EtOAc. The combined extracts were washed sequentially with water and brine, dried (Na₂SO₄), filtered and concentrated in vacuo to afford a gold oil. The crude product was purified by SiO₂ chromatography eluting with Hex/EtOAc (85:15) to afford 18.1 g (36%) of 4-pentylidene-piperidene-1-carboxylic acid tert-butyl ester (55) as a colorless oil: MS (ESI): m/z 254 (M+H).

Step 1—

A suspension of AD-Mix-β (100.0 g, 71.43 mmol), methanesulfonamide (6.80 g, 71.43 mmol), tert-BuOH (270 mL) and water (360 mL) was stirred until a single clear phase was obtained. A solution of 55 (18.1 g, 71.43 mmol) and tert-BuOH (100 mL) was added. The resulting solution was stirred at RT for 3.5 h, cooled to 0° C. and Na₂SO₃ (107 g) was added. The reaction was stirred vigorously for 1.5 h and diluted with water and EtOAc. The phases were separated and the aqueous phase extracted aqueous two times with EtOAc. The combined organic phases were washed with brine, dried over (Na₂SO₄) and concentrated in vacuo. The crude product was purified by SiO₂ chromatography eluting with a gradient of hexane/EtOAc (1:0 to 1:1) which afforded 18.7 g (91%) of 56: MS (ESI): m/z 288 (M+H).

Step 2—

To a solution of 56 (17.2 g, 59.85 mmol) and EtOAc/DCM (860 mL, 4:1) at 0° C. was added methanesulfonyl chloride (9.3 mL, 119.7 mmol) and TEA (18.4 mL, 131.7 mmol). The cooling bath was removed and the mixture was stirred at RT for 45 min. The reaction was quenched by addition of water and diluted with EtOAc. The aqueous phase was extracted twice with EtOAc and the combined EtOAc extracts were washed sequentially with 1M HCl, water, saturated NaHCO₃, water and brine. The EtOAc solution was dried (Na₂SO₄) and concentrated in vacuo. A 2 L 3 neck flask was charged with NaH (3.59 g, 89.78 mmol, 60% NaH in mineral oil). The flask was cooled in an ice bath and MeOH (400 mL) was slowly added. The solution was stirred at 0° C. for 10 min and then a solution of the mesylate and MeOH (200 mL) were added. The reaction was stirred at 0° C. for 1.5 h, concentrated in vacuo and the residue was partitioned between water and EtOAc. The aqueous phase was extracted aqueous twice with EtOAc and the combined extracts we rewashed with brine, dried (Na₂SO₄) and concentrated in vacuo to a yellow oil. The crude material was purified by SiO₂ chromatography eluting with a hexane/EtOAc gradient (9:1 to 8:2) to afford 14.3 g (89%) of 57 as a colorless oil: MS (ESI): m/z 270 (M+H), 98% ee by chiral GC (CyclosilB, 30 m×0.25 mm; 150° C. isothermal; $R_t$=57.1 min).

Step 3—

To a solution of 57 (16.2 g, 59.85 mmol) and THF (450 mL) cooled to 0° C. was added dropwise Et₃AlCN (239 mL, 239 mmol, 1M in toluene). The cooling bath was removed and the mixture was stirred at RT for 16 h. The reaction was cooled to 0° C., quenched with 1 M NaOH and diluted with EtOAc. The aqueous phase was extracted twice with EtOAc. The combined extracts were washed with brine, dried (Na₂SO₄), filtered and the solvents concentrated in vacuo. The crude product was purified by SiO₂ chromatography eluting with a hexane/EtOAc (1:0 to 8:2) to afford 10.3 g (58%) of 58a as a viscous oil: MS (ESI) m/z 297 (M+H).

Step 4—

To a solution of 58a (10.30 g, 34.75 mmol) and MeOH (400 mL) was added CoCl₆.6H₂O (16.54 g, 69.50 mmol) followed by NaBH₄ (13.15 g, 347.50 mmol) in 2 g portions over 2 h. The black reaction mixture was stirred at RT for 3 days. The reaction was slowly acidified to pH 4 with 1M HCl, filtered through CELITE® and the filter cake washed with water. The pink filtrate was extracted with Et₂O and made basic conc. NH₄OH. The aqueous solution was extracted three times with EtOAc. The combined organic was washed with brine, dried (Na₂SO₄) and concentrated to a light yellow oil in vacuo. The oil was dried to afford 9.0 g (86%) of 58b which was used without further purification: MS (ESI) m/z 301 (M+H).

Step 5—

To a solution of 58b (9.0 g, 29.9 mmol) in THF (250 mL) was added 1,1'carbonyldiimidazole (9.7 g, 59.9 mmol) and the reaction was stirred at RT for 17 h. The solvent was concentrated in vacuo and the residue partitioned between 0.5 M HCl and EtOAc. The aqueous phase was extracted two times with EtOAc and combined extracts washed sequentially with 0.5M HCl, saturated NaHCO₃, water and brine, dried (Na₂SO₄), filtered and concentrated in vacuo. The crude material was purified by SiO₂ chromatography eluting with a DCM/MeOH gradient (1:0 to 99:1) to afford 6.75 g (69%) of 59a as a white foam: MS (ESI) m/z 327 (M+H), $[\alpha_D]^{25}$=+31.2° (MeOH).

Step 6—

Introduction of the N-cyclohexylmethyl substituent into 59a was accomplished as described in step 3 of Example 1 which afforded 59b.

Step 7—

Deprotection of 59b followed the procedure described in step 3 of Example 8. Purification by SiO₂ chromatography eluting with a CH₂Cl₂/MeOH (1:0 to 99:1) gradient afforded the deprotected piperidine in 91% yield as a white solid: MS (ESI), m/z 423 (M+H), $[\alpha_D]^{25}$=+38.1° (MeOH).

Step 8—

The title compound was obtained from the product from step 7 and 15 by the procedure described in step 5 of Example 1. 71% from the title compound of step G following the procedure described in preparation XX. Purification by SiO$_2$ chromatography eluting with a CH$_2$Cl$_2$/MeOH (1:0 to 9:1) gradient afforded I-421 as a white solid: MS (ESI): m/z 538 (M+H), [α$_D$]$^{25}$=+24.4° (MeOH), mp=78.8-80.3° C.

Example 12

Human CCR5 Receptor-Ligand Binding Assay Protocol

Human CCR5 receptor (Genebank ID: 29169292) was cloned into mammalian expression vector, pTarget (Promega). The construct was transfected into CHO-G$_{α16}$ cells by using Fugene Reagent (Roche). Clones were selected under antibiotic pressure (G418 and Hygromycin) and sorted 4 times with a fluorescence activates cell sorter and a monoclonal antibody specific for CCR5 receptor (BD Biosciences Pharmigen, Mab 2D7, Cat. No. 555993). The clone with highest expression (100,000 copies per cell) was chosen for the binding assays.

Adherent cells in 225 mL tissue culture flask (~90% confluent) were harvested using 1 mM EDTA in PBS (phosphate-buffered saline) without Ca$^{2+}$ and Mg$^{2+}$. Cells were washed twice with PBS containing no Ca$^{2+}$ and Mg$^{2+}$. CHO-G$_{α16}$-hCCR5 cells were then resuspended (1×10$^6$/ml) in ice cold binding buffer (50 mM HEPES, 1 mM CaCl$_2$, 5 mM MgCl$_2$, 0.5% BSA, 0.05% NaN$_3$, pH 7.24), pH 7.4), supplemented with freshly made 0.5% BSA and 0.05% NaN$_3$.

Eighty μl CHO-G$_{α16}$-hCCR5 (1×10$^6$/ml) cells were added to 96 well plates. All dilutions were made in binding buffer (50 mM HEPES, 1 mM CaCl$_2$, 5 mM MgCl$_2$, 0.5% BSA, 0.05% NaN$_3$, pH 7.24).

The plates were incubated on a cell shaker at RT for 2 h with a final concentration of 0.1 nM $^{125}$I RANTES or $^{125}$I MIP-1α or $^{125}$I MIP-1β. The compound dilutions were made in PBS, 1% BSA. Total reaction volume was 100 μl per well. The test compounds were added to the cells prior to the addition of radioligand.

After incubation, the cells were harvested onto GF/C filter plates using Packard cell harvester. Filters were pretreated with 0.3% PEI/0.2% BSA for 30 min. The filter plate was washed rapidly 5 times with 25 mM HEPES, 500 mM NaCl, 1 mM CaCl$_2$ and 5 mM MgCl$_2$ adjusted to pH 7.1. Plates were dried in oven (70° C.) for 20 min, added with 40 μl scintillation fluid and sealed with Packard TopSeal-A. Packard Top Count was used to measure of the radioactivity for 1 min per well.

Total binding was determined with control wells added with radioisotope and buffer and the non-specific binding was determined using an excess cold RANTES to some of the control wells. Specific binding was determined by subtracting the non-specific form total binding. Results are expressed as the percentage of specific $^{125}$I RANTES binding. IC$_{50}$ values were determined using varying concentrations of the test ligand in triplicates and the data was analyzed using GraphPad Prism (GraphPad, San Diego, Calif.).

| Compound No. | Binding IC$_{50}$ (μM) | | |
|---|---|---|---|
| | RANTES | Mip-1a | Mip-1b |
| I-1 | 0.014 | 0.018 | 0.013 |
| I-90 | 0.0051 | — | 0.0018 |
| I-159 | 0.0051 | 0.0045 | 0.0105 |
| I-212 | 0.0073 | — | — |
| I-214 | 0.0082 | — | — |
| I-415 | 0.0077 | — | <0.0015 |

Example 13

Formulations

Pharmaceutical compositions of the subject Compounds for administration via several routes were prepared as described in this Example.

| Composition for Oral Administration (A) | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration (B) | |
|---|---|
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration (C) | |
|---|---|
| Ingredient | % wt./wt. |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation (D) | |
|---|---|
| Ingredient | % wt./wt. |
| Active ingredient | 0.25 g |
| Sodium Chloride | qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

| Suppository Formulation (E) | |
|---|---|
| Ingredient | % wt./wt. |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

| Topical Formulation (F) | |
|---|---|
| Ingredients | grams |
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations (G)

Several aqueous suspensions containing from about 0.025-0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50-100 microliters of formulation per actuation. A typical dosing schedule is 2-4 sprays every 4-12 hours.

The features disclosed in the foregoing description, or the following claims, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

We claim:

1. A compound according to formula Ia or Ib,

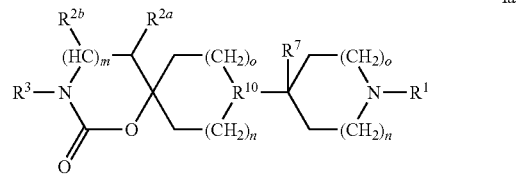

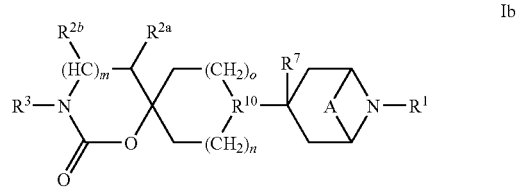

wherein:

A is $(CH_2)_q$;

$R^1$ is $C(=O)R^4$, $C(=O)X$, or $S(O)_pR^4$;

X is $NR^5R^6$ or $OR^{11}$;

$R^{2a}$ and $R^{2b}$ are (A), independently
  (i) hydrogen,
  (ii) $C_{1-10}$ alkyl,
  (iii) $C_{2-10}$ alkenyl,
  (iv) $C_{1-10}$ haloalkyl,
  (v) $C_{3-7}$ cycloalkyl,
  (vi) $C_{3-7}$ cycloalkyl-$C_{1-3}$ alkyl,
  (vii) $C_{1-10}$ heteroalkyl,
  (viii) $C_{1-10}$ alkylidene,
  (ix) $C_{1-10}$ heteroalkylidene,
  (x) aryl,
  (xi) aryl-$C_{1-3}$ alkyl,
  (xii) heteroaryl,
  (xiii) heteroaryl-$C_{1-3}$ alkyl,
  (xiv) $C_{1-10}$ alkyl wherein 2 or 3 nonadjacent carbon atoms are independently replaced with —O—, —S(O)$_p$—, —NH— or NR$^5$,
  (xv) —(CH$_2$)$_w$R$^8$ wherein w is an integer from 2 to 6, and the $C_2$-$C_6$ alkylene chain optionally contains a double bond;
  (xvi) —(CH$_2$)$_w$CH=NR$^9$ wherein w is an integer from 2 to 6; or (B), together with the carbon atoms to which they are attached, are o-phenylene optionally substituted with 1 to 3 substituents independently selected from the group consisting of $C_{1-6}$ alkyl, $C_{1-6}$ haloalkyl, $C_{1-6}$ alkoxy, $C_{1-6}$ thioalkyl, $C_{1-6}$ alkylsulfonyl, hydroxyl, halogen, $NR^{5a}R^{6a}$, cyano and nitro with the proviso that if $R^{2a}$, $R^{2b}$, together with the carbon atoms to which they are optionally substituted o-phenylene, m is 1;

$R^3$ is (i) $C_{1-10}$ alkyl,
(ii) $C_{2-10}$ alkenyl
(iii) $C_{1-10}$ heteroalkyl,
(iv) $C_{3-7}$ cycloalkyl,
(v) $C_{1-6}$ alkyl-$C_{3-7}$ cycloalkyl,
(vi) heterocycle $C_{1-6}$ alkyl,
(vii) aryl,
(viii) aryl-$C_{1-3}$ alkyl,
(ix) heteroaryl,
(x) heteroaryl $C_{1-6}$ alkyl,
(xi) $C(=O)R^{3a}$ wherein $R^{3a}$ is $C_{1-10}$ alkyl, $C_{2-10}$ alkenyl or $C_{3-7}$ cycloalkyl, or
(xii) a fragment of formula IIa-IIc;

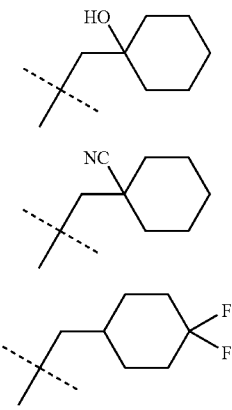

IIa

IIb

IIc $R^4$ is (i) $C_{1-10}$ alkyl,
(ii) $C_{3-7}$ cycloalkyl-$C_{1-10}$ substituted alkyl,
(iii) heterocycle,
(iv) aryl, or
(v) heteroaryl;

$R^5$ and $R^6$ are (A) when taken independently are hydrogen, $C_{1-10}$ alkyl, $C_{1-10}$ heteroalkyl, $C_{3-7}$ cycloalkyl, $C_{1-6}$ alkyl-$C_{3-7}$ cycloalkyl, heterocycle $C_{1-6}$ alkyl, aryl, aryl-$C_{1-3}$ alkyl, heteroaryl or heteroaryl $C_{1-6}$ alkyl; or, (B) $C_{3-6}$ alkylene or $[(CH_2)_2]_2O$ thereby forming a morpholine ring when taken together;

$R^{5a}$ and $R^{6a}$ are (A) hydrogen, $C_{1-6}$ alkyl or $C_{1-6}$ alkylcarbonyl when taken independently or (B) $C_{3-6}$ alkylene or $[(CH_2)_2]_2O$ when taken together;

$R^7$ is hydrogen, cyano or $C_{1-6}$ alkyl;

$R^8$ is —CN, —$NO_2$, —$CONR^{5a}R^{6a}$, $COR^9$, —$NHSO_2C_{1-6}$ alkyl;

$R^9$ is OH or $C_{1-6}$ alkoxy;

$R^{10}$ is N or $N^+$—$O^-$;

$R^{11}$ is $C_{1-10}$ alkyl, $C_{1-10}$ heteroalkyl, $C_{3-7}$ cycloalkyl, $C_{1-6}$ alkyl-$C_{3-7}$ cycloalkyl, heterocycle $C_{1-6}$ alkyl, aryl, aryl-$C_{1-3}$ alkyl, heteroaryl or heteroaryl $C_{1-6}$ alkyl;

m is 0;
n is independently 0 to 2;
o is independently 0 or 1;
p is 0 to 2;
q is 3;

wherein,
each said heteroaryl is independently selected from the group consisting of pyridyl, 1-oxy-pyridinyl, pyrimidyl, oxypyrimdinyl, pyrazinyl, pyridazinyl, pyrrolyl, thienyl, furyl, imidazolyl, pyrazolyl, oxazolyl, thiazolyl, isoxazolyl, isothiazolyl indolinyl, N-Boc-indolinyl, quinolinyl, isoquinolinyl, benzofuranyl, 4,5,6,7-tetrahydrobenzofuranyl and 1,2,3,4-tetrahydroacridinyl;

each said aryl and said heteroaryl are optionally independently substituted with 1 to 3 substituents selected from the group consisting of hydroxy, $C_{1-6}$ alkyl, $C_{1-6}$ haloalkyl, $C_{1-6}$ alkoxy, $C_{1-6}$ haloalkoxy, $C_{1-6}$ thioalkyl, aryl, aryl $C_{1-3}$ alkyl, aryloxy, heteroaryloxy, thioaryl, thioheteroaryl, aryl $C_{1-3}$ alkoxy, heteroaryl, heterocyclyl, heterocycle $C_{1-6}$ alkyl, $C_{1-6}$ alkylsulfonyl, —$NHSO_2C_{1-6}$ alkyl, $SO_2NR^{5a}R^{6a}$, $(CH_2)_u CO_2R^9$, $(CH_2)_u CONR^{5a}R^{6a}$, —$X^1C(=O)X^2$, $C_{1-10}$ alkylcarbonyl, halogen, $NR^{5a}R^{6a}$, cyano, nitro and $C_{1-10}$ alkyl wherein 2 or 3 nonadjacent carbon atoms are independently replaced with —O—, —$S(O)_p$—, —NH— or $NR^5$, wherein u is an integer from 0 to 6, $X^1$ is $NR^{5b}$ or O; $X^2$ is $NR^5R^6$ or $OR^3$ and $R^{5b}$ is H or $C_{1-6}$ alkyl;

each said heterocycle is independently selected from the group consisting of pyrrolidinyl, 1-methyl-pyrrolidinyl, piperidinyl, morpholinyl, thiomorpholinyl, tetrahydrofuranyl, dioxolanyl and pyranyl optionally substituted with 1 to 3 substituents independently selected from the group consisting of hydroxy $C_{1-6}$ alkyl, $C_{1-6}$ haloalkyl, $C_{1-6}$ alkoxy, $C_{1-6}$ thioalkyl, $C_{1-6}$ alkylsulfonyl, halogen, $NR^{5a}R^{6a}$, cyano and nitro;

pure enantiomers, partially resolved enantiomers, racemic mixtures and pharmaceutically acceptable acid addition salts thereof.

2. A compound according to claim 1 with formula Ic,

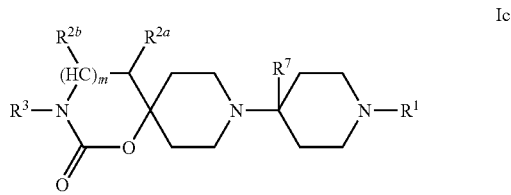

Ic $R^{2a}$ is $C_{1-10}$ alkyl, $C_{1-10}$ haloalkyl, $C_{3-7}$ cycloalkyl, $C_{3-7}$ cycloalkyl-$C_{1-3}$ alkyl, $C_{1-10}$ heteroalkyl, $C_{1-10}$ alkylidene, $C_{1-10}$ heteroalkylidene or $C_{1-10}$ alkyl wherein 2 or 3 nonadjacent carbon atoms are independently replaced with —O—, —$S(O)_p$—, —NH— or —$NR^5$—;

$R^{2b}$ is hydrogen;

$R^3$ is $C_{1-10}$ alkyl, $C_{3-7}$ cycloalkyl, $C_{1-6}$ alkyl-$C_{3-7}$ cycloalkyl, optionally substituted aryl, optionally substituted aryl-$C_{1-3}$ alkyl, optionally substituted heteroaryl, optionally substituted heteroaryl-$C_{1-3}$ alkyl;

$R^4$ is $C_{1-10}$ alkyl, optionally substituted aryl or optionally substituted heteroaryl;

$R^7$ is hydrogen, or $C_{1-6}$ alkyl;

n and o are 1; and, p is 2.

3. A compound according to claim 2 wherein $R^7$ is hydrogen or methyl.

4. A compound according to claim 3 wherein $R^1$ is $COR^4$;

$R^{2a}$ is $C_{1-10}$ alkyl, $C_{1-10}$ heteroalkyl or $C_{1-10}$ alkyl wherein 2 or 3 nonadjacent carbon atoms in the alkyl chain optionally can be independently replaced with —O—, —S(O)$_p$—, —NH— or $NR^5$;

$R^4$ is optionally substituted aryl or optionally substituted heteroaryl;

$R^{10}$ is N.

5. A compound according to claim 4 wherein $R^4$ is optionally substituted aryl.

6. A compound according to claim 4 wherein $R^4$ is optionally substituted heteroaryl.

7. A compound according to claim 6 wherein $R^4$ is optionally substituted pyridyl, optionally substituted pyrimidinyl, optionally substituted pyrazolyl, optionally substituted oxazolyl, optionally substituted isoxazolyl or optionally substituted pyrrolyl.

8. A compound according to claim 1 with the formula Id wherein

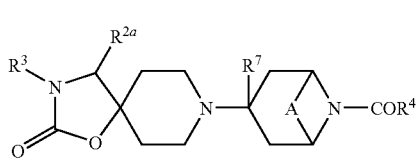

Id $R^{2a}$ is $C_{1-10}$ alkyl, $C_{1-10}$ haloalkyl, $C_{3-7}$ cycloalkyl, $C_{3-7}$ cycloalkyl-$C_{1-3}$ alkyl, $C_{1-10}$ heteroalkyl, $C_{1-10}$ alkylidene, $C_{1-10}$ heteroalkylidene or $C_{1-10}$ alkyl wherein 2 or 3 nonadjacent carbon atoms are independently replaced with —O—, —S(O)$_p$—, —NH— or $NR^5$;

$R^{2b}$ is hydrogen;

$R^4$ is optionally substituted aryl or optionally substituted heteroaryl;

$R^7$ is hydrogen or $C_{1-6}$ alkyl;

n and o are 1;

q is 3; and, p is 2.

9. A pharmaceutical composition for the comprising a compound according to either claim 1 admixed with at least one pharmaceutical acceptable carrier, diluent or excipient.

* * * * *